US009802957B2

(12) United States Patent
Zhou et al.

(10) Patent No.: US 9,802,957 B2
(45) Date of Patent: Oct. 31, 2017

(54) PROCESSES OF PREPARING A JAK1 INHIBITOR AND NEW FORMS THERETO

(71) Applicant: Incyte Corporation, Wilmington, DE (US)

(72) Inventors: Jiacheng Zhou, Newark, DE (US); Shili Chen, Newark, DE (US); Yongzhong Wu, Chadds Ford, PA (US); Zhongjiang Jia, Kennett Square, PA (US); Yingrui Dai, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 14/699,500

(22) Filed: Apr. 29, 2015

(65) Prior Publication Data

US 2015/0344497 A1    Dec. 3, 2015

Related U.S. Application Data

(60) Provisional application No. 61/986,789, filed on Apr. 30, 2014, provisional application No. 61/986,738, filed on Apr. 30, 2014.

(51) Int. Cl.
C07D 495/14 (2006.01)
C07D 309/14 (2006.01)
C07D 495/04 (2006.01)

(52) U.S. Cl.
CPC ......... *C07D 495/14* (2013.01); *C07D 309/14* (2013.01); *C07D 495/04* (2013.01)

(58) Field of Classification Search
CPC .................................................. C07D 495/14
USPC ......................................................... 546/83
See application file for complete search history.

(56) References Cited

U.S. PATENT DOCUMENTS

| | | |
|---|---|---|
| 4,753,951 A | 6/1988 | Takada et al. |
| 5,521,184 A | 5/1996 | Zimmermann |
| 6,025,366 A | 2/2000 | Walsh et al. |
| 6,518,265 B1 | 2/2003 | Kato et al. |
| 7,335,667 B2 | 2/2008 | Rodgers et al. |
| 7,598,257 B2 | 10/2009 | Rodgers et al. |
| 7,683,171 B2 | 3/2010 | Pitts et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,445,488 B2 | 5/2013 | Rodgers et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 9,181,271 B2* | 11/2015 | Li ........................ C07D 495/14 |
| 9,221,845 B2 | 12/2015 | Cao |
| 9,290,506 B2 | 3/2016 | Metcalf |
| 9,376,439 B2 | 6/2016 | Rodgers et al. |
| 9,498,467 B2 | 11/2016 | Leopold |
| 2006/0106020 A1 | 5/2006 | Rodgers et al. |
| 2006/0178393 A1 | 8/2006 | Pitts |
| 2007/0149506 A1 | 6/2007 | Arvanitis et al. |

(Continued)

FOREIGN PATENT DOCUMENTS

AU   2007338793    7/2008
CN   1323307      11/2001

(Continued)

OTHER PUBLICATIONS

26th Annual JPMorgan Healthcare Conference presentation dated Jan. 8, 2008, 28 pages.
Abe et al., "Effective Methods for Introducing Some Aryl and Heteroaryl Substituent onto 1-Azaazulene Nuclei", Heterocycles, 2005, 66: 229-240.
Abelson et al., "Alternate reference values for tear film break-up time in normal and dry eye populations, Lacrimal Gland, Tear Film, and Dry Eye Syndromes 3 Part B", Adv Exp Med Biol, 2002, 506: 1121-1125.
Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002, 506: 1079-86.

(Continued)

*Primary Examiner* — Rita Desai
(74) *Attorney, Agent, or Firm* — Fish & Richardson P.C.

(57) ABSTRACT

This invention relates to processes for preparing a JAK1 inhibitor having Formula Ia:

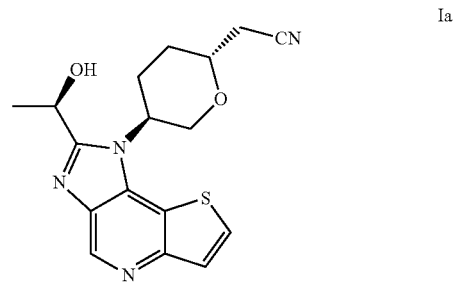

as well as new forms of the inhibitor.

9 Claims, 15 Drawing Sheets

(56) References Cited

U.S. PATENT DOCUMENTS

| | | |
|---|---|---|
| 2008/0312259 A1 | 12/2008 | Rodgers et al. |
| 2009/0197869 A1 | 8/2009 | Arvanitis et al. |
| 2009/0215766 A1 | 8/2009 | Rodgers et al. |
| 2010/0022522 A1 | 1/2010 | Rodgers et al. |
| 2010/0113416 A1 | 5/2010 | Friedman et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0288107 A1 | 11/2011 | Parikh et al. |
| 2012/0014989 A1 | 1/2012 | Rodgers |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0301464 A1 | 11/2012 | Friedman et al. |
| 2012/0329782 A1 | 12/2012 | Arvanitis et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0296299 A1 | 11/2013 | Rodgers et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2015/0065447 A1* | 3/2015 | Sandor ............... C07D 495/14 514/49 |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0164900 A1 | 6/2015 | Rodgers et al. |
| 2015/0225411 A1 | 8/2015 | Yao et al. |
| 2015/0238492 A1 | 8/2015 | Rodgers et al. |
| 2015/0246046 A1 | 9/2015 | Vaddi et al. |
| 2015/0250790 A1 | 9/2015 | Parikh et al. |
| 2015/0342952 A1 | 12/2015 | Leopold |
| 2016/0000795 A1 | 1/2016 | Scherle |
| 2016/0015695 A1 | 1/2016 | Li et al. |
| 2016/0024109 A1 | 1/2016 | Li |
| 2016/0067253 A1 | 3/2016 | Li et al. |
| 2016/0257687 A1 | 9/2016 | Zhou |
| 2016/0272648 A1 | 9/2016 | Rodgers et al. |
| 2016/0289215 A1 | 10/2016 | Li et al. |
| 2016/0346286 A1 | 12/2016 | Rodgers et al. |
| 2016/0347734 A1 | 12/2016 | Liu et al. |

FOREIGN PATENT DOCUMENTS

| | | |
|---|---|---|
| CN | 101516875 | 8/2009 |
| CN | 102131389 | 7/2011 |
| EP | 0223420 | 5/1987 |
| EP | 0587473 | 3/1994 |
| EP | 0727217 | 8/1996 |
| EP | 1104764 | 6/2001 |
| WO | WO 00/09495 | 2/2000 |
| WO | WO 00/53595 | 9/2000 |
| WO | WO 01/14402 | 3/2001 |
| WO | WO 01/64655 | 9/2001 |
| WO | WO 02/00196 | 1/2002 |
| WO | WO 02/16370 | 2/2002 |
| WO | WO 03/024967 | 3/2003 |
| WO | WO 03/037347 | 5/2003 |
| WO | WO 03/099771 | 12/2003 |
| WO | WO 2004/005281 | 1/2004 |
| WO | WO 2004/046120 | 6/2004 |
| WO | WO 2004/056786 | 7/2004 |
| WO | WO 2004/080980 | 9/2004 |
| WO | WO 2005/028444 | 3/2005 |
| WO | WO 2005/123719 | 12/2005 |
| WO | WO 2006/056399 | 6/2006 |
| WO | WO 2007/044050 | 4/2007 |
| WO | WO 2009/155156 | 12/2009 |
| WO | WO 2011/003418 | 1/2011 |
| WO | WO 2013/007765 | 1/2013 |
| WO | WO 2013/007768 | 1/2013 |
| WO | WO 2014/071031 | 5/2014 |

OTHER PUBLICATIONS

Abstract of Chilean patent application No. 3496-06 published in Official Gazette of the Republic of Chile (Jun. 1, 2007) and publication (2 pages).

Aho et al., Expression of human pim family genes is selectively up-regulated by cytokines promoting T helper type 1, but not T helper type 2, cell differentiation, Immunology, 2005, 116: 82-88.

Albach et al., "Diagnosis of keratoconjunctivitis sicca in rheumatoid arthritis. The value of various tests", Ophthalmologe, Apr. 1994; 91(2):229-34—in German (with English abstract/summary contained therein).

Anderson et al., "Biochemical characterization of GSK1070916, a potent and selective inhibitor of Aurora B and Aurora C kinases with an extremely long residence time", Biochem. J., 2009, 420(2): 259-265.

Bachmann et al., "The serine/threonine kinase Pim-1," The International Journal of Biochemistry and Cell Biology, 2005, 37: 726-730.

Banker et al., "Modern Pharmaceuticals" Third Edition, 1996, 596.

Barabino et al., "Tear film and ocular surface tests in animal models of dry eye; uses and limitations," Experimental Eye Research, 2004, 79: 613-621.

Barr et al., "Corneal scarring in the Collaborative Longitudinal Evaluation of Keratoconus (CLEK) Study: baseline prevalence and repeatability of detection", Cornea, 1999, 18(1):34-46.

Baudouin et al., "Flow cytometry in impression cytology specimens. A new method for evaluation of conjunctival Inflammation," Invest Ophthalmol Vis Sci, 1997, 38: 1458-1464.

Baytel et al., "The human Pim-2 proto-oncogene and its testicular expression," Biochimica et Biophysica Acta, 1998, 1442: 274-285.

Begley et al., "Use of the dry eye questionnaire to measure symptoms of ocular irritation in patients with aqueous tear deficient dry eye", Cornea, 2002, 21: 664-70.

Bell and Zalay, "Synthesis of Substituted 3-Amino [6, 5-b] triazinoindoles." Journal of Heterocyclic Chemistry, Oct. 1975, 12(5):1001-1004.

Berge et al., "Pharmaceutical salts", J. Pharma. Science, 1977, 66(1): 1-19.

Beyer, "Uber die Synthese von 2-Methylmercapto-1,3,4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).

Bhattacharya et al., "Polymorphism in Pharmaceutical Solids," Second Edition, 2009, 192:327-345.

Bhovi, et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, Jul.-Sep. 2004, 14: 15-18.

Bioreversible Carriers in Drug Design, ed. Edward B. Roche, American Pharmaceutical Association and Pergamon Press, 1987.

(56) References Cited

OTHER PUBLICATIONS

Blom, "Two-Pump at-Column-Dilution Configuration for Preparative Liquid Chromatography—Mass Spectrometry," J. Comb. Chem., 2002, 4: 295-301.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blume-Jensen et al, "Oncogenic kinase signaling", Nature, 2001, 411(6835):355-365.
Bock et al. "Managing drug resistance in cancer: lessons from HIV therapy." Nature, Jul. 2012, 12: 494-501.
Bolen, "Nonreceptor tyrosine protein kinases", Oncogene, 1993, 8(8):2025-31.
Bollrath et al., "130-Mediated Stat3 Activation in Enterocytes Regulates Cell Survival and Cell-Cycle Progression during Colitis-Associated Tumorigenesis," Cancer Cell, 2009, 15:91-102.
Borie et al., "Combined Use of the Jak3 Inhibitor CP-690, 550 with Mycophenolate Mofetil to Prevent Kidney Allograft Rejection in Nonhuman Primates", Transplantation, Dec. 2005, 80(12):1756-64.
Bosworth, "JAK1/JAK2 Inhibitor Ruxolitinib Is a Rising Start" Clinical Oncology, Apr. 2011, 06:04, 3 pages.
Boudny et al., "JAK/STAT signaling pathways and cancer," Neoplasm, 2002, 49:349-355.
Bourcier et al., "Expression of CD40 and CD40 ligand in the human conjunctival epithelium", Invest Ophthalmol Vis Sci, 2000, 41:120-126.
Bowman et al. "STATs in oncogenesis", Oncogene, 2000, 19:2474-2488.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998, 67:687-697.
Brignole et al., "Flow cytometric analysis of inflammatory markers in conjunctival epithelial cells of patients with dry eyes," Invest Ophthalmol Vis Sci, 2000, 41:1356-1363.
Brignole et al., "Flow cytometric analysis of inflammatory markers in KCS: 6-month treatment with topical cyclosporin A," Invest Ophthalmol Vis Sci, 2001, 42:90-95.
Brignole et al., "Flow cytometry in conjunctival impression cytology: a new tool for exploring ocular surface pathologies," Exp Eye Res, 2004, 78:473-481.
Bromberg et al., "Inflammation and Cancer: IL-6 and STAT3 Complete the Link," Cancer Cell, 2009, 15:79-80.
Bron et al., "Grading of corneal and conjunctival staining in the context of other dry eye tests", Cornea, 2003, 22(7):640-50.
Bron et al., "Methodologies to Diagnose and Monitor Dry Eye Disease: Report of the Diagnostic Methodology Subcommittee of the International Dry Eye Workshop (2007)", The Ocular Surface, Apr. 2007, 5(2): 108-152.
Burger et al., "Gp130 and ras mediated signaling in human plasma cell line IN/a-6: a cytokine-regulated tumor model for plasmacytoma", Hematol J., 2001, 2:42-53.
Burger et al., "Janus kinase inhibitor INCB20 has antiproliferative and apoptotic effects on human myeloma cells in vitro and in vivo", Mol. Cancer Ther., Jan. 2009, 8(1): 26-35.
Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, Jun. 2010, 35(6):457-465.
Candotti et al., "Structural and functional basis for JAK3-deficient severe combined immunodeficiency.", Blood, 1997, 90(10): 3996-4003.
Candotti et al., "Molecular aspects of primary immuno-deficiencies: lessons from cytokine and other signaling pathways.", J Clin Invest, May 2002, 109(10): 1261-9.
Carey and Sundberg, Advanced Organic Chemistry, Part B: Reactions and Synthesis, 4th ed., Kluwer Academic/Plenum Publishers:New York, 2001, 111-119.
Carey and Sundberg, Advanced Organic Chemistry, Part B: Reactions and Synthesis, Oxidations, 4th ed., Kluwer Academic/Plenum Publishers:New York, 2001, 747-757.
Cennak et al, "Is complete androgen insensitivity syndrome associated with alterations in the meibomian gland and ocular surface," Cornea, 2003, 22:516-521.
Cetkovic-Cvrlje et al., "Targeting JAK3 with JANEX-1 for prevention of autoimmune type 1 diabetes in NOD mice.", Clin Immunol, 2003, 106(3): 213-25.
Chalandon, "Targeting mutated protein tyrosine kinases and their signaling pathways in hematologic malignancies," Haematologica, 2005, 90(7):949-68.
Changelian et al., "Prevention of Organ Allograft Rejection by a Specific Janus Kinase 3 Inhibitor", Science, 2003, 302: 875-878.
Chauhan et al, "Autoimmunity in Dry Eye due to resistance of Th17 to Treg Suppression", J. Immunology, 2009, 182(3):1247-52.
Chemical encyclopedia publication "Soviet Encyclopedia," Moscow, 1988, 1:242-243.
Chen et al., "Stat3 Activation in Human Endometrial and Cervical Cancer", British Journal of Cancer, 2007, 96: 591-599.
Chew et al., "An instrument for quantifying meibomian lipid on the lid margin: the Meibometer", Curr Eye Res, 1993, 12:247-254.
Chew et al., "The casual level of meibomian lipids in humans", Current Eye Research, 1993, 12:255-259.
Chinese Office Action in Chinese Application No. 201380068740.2, dated Jun. 3, 2016, 17 pages (English Translation).
Cho et al, "Review of the tear break-up time and a closer look at the tear break-up time of Hong Kong Chinese", Optom Vis Sci, 1993, 70(1):30-8.
Choi Ha-Soon et al., "Design and synthesis of 7H-pyrrolo [2,3-d]pyrimidines as focal adhesion kinase inhibitors. Part 1", Bioorg. & Med. Chem. Lett., 2006, 16(8):2173-2176.
Chu-Moyer et al., "Preparation of the Four Regioisomeric 2-(Methylthio)oxazolopyridines: Useful Synthons for Elaboration to 2-(Amino substituted)oxazolopyridines", J. Org. Chem., 1995, 60(17): 5721-5725.
Cilloni et al., "Emerging drugs for chronic myeloid leukemia", Expert Opinion on Emerging Drugs, Jun. 2010, 15(2): 175-184.
Claridge et al., "Discovery of a novel and potent series of thieno[3,2-b]pyridine-based inhibitors of c-Met and VEGFR2 tyrosine kinases," Bioorganic & Medicinal Chemistry Letters, 2008, 2793-2798.
Clark et al., "Discovery and Development of Janus Kinase (JAK) inhibitors for Inflammatory Diseases," J Med Chem., 2014, A-P.
Coligan et al, Wiley Press; Methods in Molecular Biology: vol. 225, Inflammation Protocols., Winyard, P.G. and Willoughby, D.A., Humana Press (2003).
Communication dated Jan. 22, 2009 for European Appln. No. 06839328.9 (5 pgs.).
Conklyn et al., "The JAK3 inhibitor CP-0690550 selectively reduces NK and CD8+ cell numbers in cynomolgus monkey blood following chronic oral dosing," Journal of Leukocyte Biology, Dec. 2004, 76: 1248-1255.
Costa Rican Office Action in CR Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (1988).
Daniels et al., "Imatinib mesylate inhibits the profibrogenic activity of TGF-? and prevents bleomycinmediated lung fibrosis," J. Clin. Invest, Nov. 2004, 114(9):1308-1316.

(56) References Cited

OTHER PUBLICATIONS

Danjo et al., "Observation of precorneal tear film in patients with Sjogren's syndrome", Acta Ophthalmol Scand, 1995, 73:501-505.
De Paiva et al, "IL-17 disrupts corneal bather following desiccating stress," Mucosal Immunol., 2009, 2(3):243-53.
De Vos et al., "JAK2 tyrosine kinase inhibitor tylphostin AG490 downregulates the mitogen-activated protein kinase (MAPK) and signal transducer and activator of transcription (STAT) pathways and induces apoptosis in myeloma cells.", Br J Haematol, 2000, 109(4): 823-8.
Deng Jun et al, "Rh-catalyzed asymmetric hydrogenation of gamma-phthalimido-substituted esters: an efficient enantioselective synthesis of beta-aryl-gamma-amino acids", Org. Lett., 2007, 9(23):4825-4827.
Deuse et al., "Novel Immunosuppression: R348, a JAK3- and Syk-Inhibitor Attenuates Acute Cardiac Allograft Rejection," Transplantation, 2008, 85(6): 885-892.
Doane, "An instrument for in vivo tear film interferometry", Optom Vis Sci, 1989, 66: 383-8.
Doleschall et al., "Thermal and Acid Catalysed Degradations of 3-alkylthio-6,7-dihydro[1.2.4]triazino[1,6-c]quinazolin-5-ium-l-olates," Tetrahedron, 1974, 30:3997-4012.
Dorwald, "Side Reactions in Organic Synthesis: A Guide to Successful Synthesis Design," Wiley-VCH, 2005, Chapter 1, 32 pages.
Dudley et al. "A VEGF/JAK2/STATS axis may partially mediate endothelial cell tolerance to hypoxia", Biochem. J., 2005, 390(Pt 2):427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl et al., "Therapeutic applications of viscous and injectable poly(ortho esters)," Adv. Drug. Deliv. Rev., 2001, 53:45-73.
Eliason et al., "Staining of the conjunctiva and conjunctival tear film," Br J Ophthalmol, 1990, 74:519-22.
Expert Scientific Group on Phase One Clinical Trials Final Report, Nov. 30, 2006, pp. C1, C35-C38.
Saettone and Salminen, "Ocular inserts for topical delivery", Advanced Drug Delivery Reviews, 1995, 16:95-106.
Farrell et al., "A classification for dry eyes following comparison of tear thinning time with Schirmer tear test," Acta Ophthalmol (Copenh), 1992, 70(3):357-60.
Farrell et al., "A clinical procedure to predict the value of temporary occlusion therapy in keratoconjunctivitis sicca," Ophthal Physiol Opt, 2003, 23:1-8.
Farris, "Tear osmolarity-13 a new gold standard?" Adv Exp Med Biol, 1994, 350:495-503.
Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Flex et al., "Somatically acquired JAK1 mutations in adult acute lymphoblastic leukemia", J. Exp Med., 2008, 205:751-8.
Fonesca et al., "Interleukin-6 as a key player in systemic inflammation and joint destruction", Autoimmunity Reviews, 2009, 8:538-42.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Fridman et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman et al., "Preclinical evaluation of local JAK1 and JAK2 inhibition in cutaneous inflammation", Journal of Investigative Dermatology, Sep. 2011, 131(9): 1838-1844.
Fridman et al., "Efficacy and Tolerability of Novel JAK Inhibitors in Animal Models of Rheumatoid Arthritis" poster presented at the ACR/ARHP (American College of Rheumatology / Association of Rheumatology Health Professionals) Scientific Meeting 2007, Boston, MA. Nov. 10, 2007. Abstract 1771, poster 285 (1 page).
Fridman et al., "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman et al., "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov 8-10, 2007. Poster 0009 (1 page).
Fujihara et al., "Evaluation of human conjunctival epithelium by a combination of brush cytology and flow cytometry: an approach to the quantitative technique", Diagn Cytopathol, 1997, 17:456-60.
Fujii et al., "Aberrant expression of serine/threonine kinase Pim-3 in hepatocellular carcinoma development and its role in the proliferation of human hepatoma cell lines" International Journal of Cancer, 2005, 114: 209-218.
Fukagawa et al., "Histological evaluation of brush cytology of rabbit conjunctiva", Nippon Ganka Gakkai Zasshi, 1993, 97:1173-8 (contains English abstract within the article).
Gaertner, "Cyclization of 1-Alkylamino-3-halo-2-alkanols to 1-Alkyl-3-azetidinols," J. Org. Chem., 1967, 32: 2972-76.
Gaestel et al., "Targeting innate immunity protein kinase signalling in inflammation," Nat Rev Drug Discov., Jun. 2009, 8(6):480-99.
Ghelardi et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother., 2004, 48:3396-3401.
Gilchrist et al., "5H-2-Pyrindines from 2-Bromocyclopentene-1-carboxaldehyde," Tetrahedron, Jan. 1, 1995, 9119-9126.
Glasson et al., "Differences in clinical parameters and tear film of tolerant and intolerant contact lens wearers," Invest Ophthalmol Vis Sci, 2003, 44:5116-5124.
Glattfeld, "Improvements in the Preparation of DL-Threonic and DL-Erythronic Acids", J. Am. Chem. Soc., 1940, 62:974-977.
Gobbels et al., "Tear secretion in dry eyes as assessed by objective fluorophotometry.," Ger J Ophthalmol, 1992, 1:350-353.
Golding et al., "X-ray and scanning electron microscopic analysis of the structural composition of tear ferns", Cornea, Jan. 1994, 13(1):58-66.
Gomtsyan et al, "Design, synthesis, and structure-activity relationship of 6-alkynylpyrimidines as potent adenosine kinase inhibitors," J. Med. Chem., 2002, 45(17):3639-3648.
Gooseman et al., "The intramolecular b-fluorine . . . ammonium interaction in 4- and 8-membered rings", Chem. Commun, 2006, 30:3190-3192.
Gorre et al., "Clinical Resistance to STI-571 Cancer Therapy Caused by BCR-ABL Gene Mutation or Amplification." Science, 2001, 293:876-880.
Gotlieb, Alice, Presentation at the 2008 American Academy of Dermatology, 66th Annual Meeting, San Antonio, TX. Feb. 1, 2008, symposium-303 (12 pp.).
Goto et al., "Color mapping of tear lipid layer thickness distribution from the image analysis in DR-1 tear lipid layer interference images," ARVO abstract, 2004, 2 pages.
Goto et al., "Computer-synthesis of an interference color chart of human tear lipid layer by a colorimetric approach," Invest Ophthalmol Vis Sci, 2003, 44:4693-7.
Goto et al., "Differentiation of lipid tear deficiency dry eye by kinetic analysis of tear interference images,",Arch Ophthalmol, 2003, 121:173-80.

(56) References Cited

OTHER PUBLICATIONS

Goto et al., "Evaluation of the tear film stability after laser in situ keratomileusis using the tear film stability analysis system," Am J Ophthalmol, Jan. 2004, 137(1):116-20.
Goto et al., "Tear Film Stability Analysis System: Introducing a new application for videokeratography", Cornea, Nov. 2004, 23(8):S65-S70.
Goto et al., "Kinetic analysis of tear interference images in aqueous tear deficiency dry eye before and after punctal occlusion," Invest Ophthalmol Vis Sci, 2003, 44:1897-905.
Gottlieb, "Psoriasis: Emerging Therapeutic Strategies," Nat Rev Drug Disc., Jan. 2005, 4:19-34.
Grabbe et al., "Immunoregulatory mechanisms involved in elicitation of allergic-contact hypersensitivity," Immunol Today, Jan. 1998, 19(1):37-44 (only 1 page provide and marked "best available copy").
Green and Wuts, P.G.M.. Protective Groups in Organic Synthesis, 3rd. Ed., Wiley & Sons, Inc., New York (1999).
Gregory et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Guillon, "Tear film photography and contact lens wear", J Br Contact Lens Assoc, 1982;5:84-7.
Gura, "Systems for Identifying New Drugs Are Often Faulty," Science, Nov. 1997, 278(5340): 1041-1042.
Guschin et al, "A major role for the protein tyrosine kinase JAK1 in the JAK/STAT signal transduction pathway in response to interleukin-6", Embo J 14:1421-1429 (1995).
Hamze ' et al., "Synthesis of Various 3-Substituted 1,2,4-Oxadiazole-Containing Chiral β3 - and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Helal et al., "Stereoselective Synthesis of cis-1,3-Disubstituted Cyclobutyl Kinase Inhibitors," Organic Letters, (2004), 6(11), pp. 1853-1856.
Hickenbottom "Reactions of organic compounds," State Scientific-Technical Publishing Association, Chemical Literature Section, Moscow, 1939, pp. 360-362.
Higuchi et al., "Pro-drugs as Novel Delivery Systems," vol. 14 of the A.C.S. Symposium Series (1975).
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
International Search Report and Written Opinion in International Application No. PCT/US2013/067794, mailed Dec. 17, 2013, 14 pages.
International Search Report and Written Opinion in International Application No. PCT/US2015/028224, dated Jul. 21, 2015, 9 pages.
Iranpoor, "A Rapid and Facile Conversion of Primary Amides and Aldoximes to Nitriles and Ketoximes to Amides with Triphenylphosphine and N-Chlorosuccinimide," G Syn., 2002, Commun 32:2535-41.

Ishizaki et al., "Pharmacological Properties of Y-27632, a Specific Inhibitor of Rho-Associated Kinases", Molecular Pharmacology, 2000, 57, 976-983.
Itagaki et al, "Expedient Synthesis of Potent Cannabinoid Receptor Agonist (−)-CP55,940", Organic Letters, 2005, 7(19): 4181-4183.
James et al., "A unique clonal JAK2 mutation leading to constitutive signalling causes polycythaemia vera", Nature, 434 (7037):1144-8 (2005).
Janes et al., "Effective and selective targeting of leukemia cells using a TORC1/2 kinase inhibitor.", Nature Medicine (2010) LNKD-PUBMED.20072130, vol. 16, No. 2, pp. 205-213 XP002673719.
Jee et al., "Overview: animal models of osteopenia and osteoporosis", J Musculoskel. Neuron, Interact., 1(3):193-207 (2001).
Jester et al., "In vivo biomicroscopy and photography of meibomian glands in a rabbit model of meibomian gland dysfunction", Invest Ophthalmol Vis Sci, 1982;22:660-7.
Johnson et al., "The effect of instilled fluorescein solution volume on the values and repeatability of TBUT measurements", Cornea, 2005;24:811-7.
Kaercher, "Ocular symptoms and signs in patients with ectodermal dysplasia syddromes", Graefe's Arch Clin Exp Ophthalmol, 2004;495-500.
Kamb, "What's wrong with our cancer models?," Nature Reviews, Feb. 2005, 161-165.
Kaushansky, "Lineage-Specific Hematopoietic Growth Factors," NEJM, 2006, 354:2034-45.
Kawamura et al., "Molecular cloning of L-JAK, a Janus family protein-tyrosine kinase expressed in natural killer cells and activated leukocytes," Proc Natl Acad Sci USA, 1994, 91(14): 6374-8.
Kharas et al., "ABL Oncogenes and Phosphoinositide 3-Kinase: Mechanism of Activation and Downstream Effectors," Cancer Res., Mar. 2005, 65(6):2047-2053.
Kim et al., "Zinc-Modified Cyanoborohydride as a Selective Reducing Agent," J. Org. Chem., 1985, 50: 1927-1932.
King-Smith et al., "Three interferometric methods for measuring the thickness of layers of the tear film," Optom Vis Sci, 1999, 76:19-32.
Kiss, "Recent developments on JAK2 inhibitors: A patent review", Expert Opinion on Therapeutic Patents, Apr. 2010, 20(4):471-495.
Kojima et al., "A new noninvasive tear stability analysis system for the assessment of dry eyes", Invest Ophthalmol Vis Sci, 2004, 45(5):1369-74.
Kola, "Can the pharmaceutical industry reduce attrition rates?" Nature Reviews Drug Discovery, 2004, 3:711-715.
Komuro et al., "Assessment of meibomian gland function by a newly developed laser meibometer", Adv Exp Med Biol, 2002, 506:517-520.
Korb et al., "The effect of two novel lubricant eye drops on tear film lipid layer thickness in subjects with city eye symptoms", Optom Vis Sci, 2005, 82: 594-601.
Korb et al., "Increase in tear film lipid layer thickness following treatment of meibomian gland dysfunction", Adv Exp Med Biol, 1994, 350:293-8.
Korolev et al., "Pd-EDTA as an efficient catalyst for Suzuki-Miyaura reactions in water", Tet. Lett., 2005, 46: 5751-5754.
Kortylewski et al., "Regulation of the IL-23 and IL-12 balance by Stat3 signaling in the tumor microenvironment", Cancer Cell, 2009, 15:114-123.
Kontzias et al., "Jakinibs: a new class of kinase inhibitors in cancer and autoimmune disease," Curr.299. Opin. Pharm., 2012, 12: 464-470.
Kruh et al., "The complete coding sequence of arg defines the Abelson subfamily of cytoplasmic tyrosine kinases.", Proc. Natl. Acad. Sci., Aug. 1990, 87:5802-5806.
Kubinyi, "QSAR: Hansch Analysis and Related Approaches," Methods and Principles in Medicinal Chemistry, Manhold, R. ed. Weinheim, NY, 1993, 42 pages.
Kudelacz et al. "The JAK-3 inhibitor CP-690550 is a potent anti-inflammatory agent in a murine model of pulmonary eosinophilia", European Journal of Pharmacology, 2008, 582: 154-161.

(56) References Cited

OTHER PUBLICATIONS

Kumar, "Kinase drug discovery approaches in chronic myeloproliferative disorders", Oncogene, Jun. 2009, 28(24): 2305-23.
Kuo et al., "Pd-EDTA as an efficient catalyst for Suzuki-Miyaura reactions in water", Chem Commun, 2007, 301-3.
Kuppens et al., "Basal tear turnover and topical timolol in glaucoma patients and healthy controls by Fluorophotometry", Invest Ophthalmol Vis Sci, 1992, 33:3442-3448.
Lai et al., "Mechanistic Study on the Inactivation of General Acyl-CoA Dehydrogenase by a Metabolite of Hypoglycin A," J. Am. Chem. Soc., 1991, 113: 7388-7397.
Lam et al, "Tear Cytokine Profiles in Dysfunctional Tear Syndrome", Am J Ophthalmol., 2009, 147(2) : 198-205.
Larock, "Comprehensive Organic Transformations", Wiley-VCH, 2nd Ed. (1999) pp. 1949-50, 1958-59, 1976, and 1983-1985.
Leaf, Clifton, Health Administrator vol. XVII, 2005, 1:172-183.
Lemp "Report of National Eye Institute/Industry Workshop on clinical trials in dry eyes," CLAO J, 1995, 21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (Jul. 5, 2010) (4 pages).
Levine et al., "Activating mutation in the tyrosine kinase JAK2 in polycythemia vera, essential thrombocythemia, and myeloid metaplasia with myelofibrosis", Cancer Cell, 2005, 7:387-397.
Levitzki, "Tyrosine kinases as targets for cancer therapy", Eur. J. Cancer, 2002, 38(suppl. 5):S11-S18.
Levy et al. "INCB018424 A Selective Janus Kinase 1/2 Inhibitor" Presentation at the 50th American Society of Hematology Annual Meeting (ASH), Dec. 8, 2008, 27 pages.
Li et al., "The synthesis and the antitumor activity of 5,7-disubstituted pyrazolo [1,5-a] pyrimidines," Chinese J Med Chem., Feb. 28, 2007, 17(1):18-22.
Li et al., "Pim-3, a proto-oncogene with serine/threonine kinase activity, is aberrantly expressed in human pancreatic cancer and phosphorylates Bad-mediated apoptosis in human pancreatic cell lines," Cancer Research, 2006, 66(13): 6741-7.
Lima and Barreiro, "Bioisosterism: a useful strategy for molecular modification and drug design," Curr Med Chem., 2005, 12(1):23-49.
Lin, "Constitutive Activation of JAK3/STAT3 in Colon Carcinoma Tumors and Cell Lines," Am J Pathol., 2005, 167(4):969-80.
Lin et al., "Enantioselective synthesis of Janus kinase inhibitor INCB018424 via an organocatalytic aza-Michael reaction," Organic Letters, 2009, 11(9): 1999-2002.
Ling et al., "Knockdown of STAT3 Expression by RNA Interference Inhibits the Induction of Breast Tumors in Immunocompetent Mice," Cancer Res, Apr. 2005 65:2532.
Liu et al., "Combined Inhibition of Janus Kinase 1/2 for the Treatment of JAK2V617F-Driven Neoplasms: Selective Effects on Mutant Cells and Improvements in Measures of Disease Severity," Clin Cancer Res, 2009, 15(22):6891-6900.
Lucet et al., "The structural basis of Janus kinas 2 inhibition by a potent and specific pan-Janus inhibitor," kinase Blood, 2006, 107(1):176-183.
Macchi et al., "Mutations of Jak-3 gene in patients with autosomal severe combined immune deficiency (SCID)", Nature, 1995, 377:65-8.
Madden et al., "Comparative study of two non-invasive tear film stability techniques", Curr Eye Res, 1994, 13(4):263-9.
Madhusudan et al., "Tyrosine kinase inhibitors in cancer therapy," Clin Biochem., 2004, 37(7):618-35.
Maffioli et al., "Mild and Reversible Dehydration of Primary Amides with PdCl2 in Aqueous Acetonitrile", Organic Letters, 2005, 7(23): 5237-39.
Main et al, "High throughput synthesis of diverse 2,5-disubstituted indoles using titanium carbenoids bearing boronate functionality", Tetrahedron, 2007, 64(5):901-914.
Mainstone et al., "Tear meniscus measurement in the diagnosis of dry eye", Curr Eye Res, 1996, 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Mandal, "Cancer Classification," 2014. Available from: <http://www.news-medical.net/health/Cancer-Classification.aspx, 6 pages.
Manjula et al., "Rapid Method of Converting Primary Amides to Nitriles and Nitriles to Primary Amides by ZnC12 using Microwaves under Different Reaction Conditions", Syn. Commun, 2007, 37:1545-50.
Manning et al., "The Protein Kinase Complement of the Human Genome," Science, 2002, 298(5600):1912-16 and 1933-34.
Mao et al., "Advances in research of tyrosine kinases inhibitor of vascular endothelial growth factor receptor," Chinese J New Drugs, Dec. 31, 2008, 17(7):544-550.
March, Jerry, Advanced Organic Chemistry: Reactions, Mechanisms, and Structure, 3rd ed., John Wiley & Sons:New York, pp. 845-855 (1985).
Marquardt et al., "Modification of tear film break-up time test for increased reliability" in Holly ed. The Preocular Tear Film in Health, Disease and Contact Lens Wear. Lubbock, Texas: Dry Eye Institute, 1986:57-63.
Maruyama et al., "Effect of environmental conditions on tear dynamics in soft contact lens wearers," Invest Ophthalmol Vis Sci, 2004, 45(8):2563-8.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996, 103:664-669.
Mathers et al., "Video imaging of the meibomian gland", Arch Ophthalmol, 1994, 112:448-9.
Mathers, "Evaporation from the ocular surface", Exp Eye Res, 2004, 78:389-394.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/my-asthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
McNamara et al., "Fluorometry in contact lens research: The next step," Optom Vis Sci, 1998, 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986, 64(4):441-4.
Mesa et al. "INCB018424, A Selective JAK 1/2 Inhibitor, Significantly Improves the Compromised Nutritional Status and Frank

(56) References Cited

OTHER PUBLICATIONS

Cachexia in Patients with Myelofibrosis (MF)" Poster #1760 at the American Society of Hematology Annual Meeting (ASH), Dec. 6, 2008 (19 pages).
Mesa et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, Nov. 2011, 117(21):4869-4877.
Mesa et al., "Emerging drugs for the therapy of primary and post essential thrombocythemia, post polycythemia vera myelofibrosis", Expert Opinion on Emerging Drugs England, 2009, 14(3): 471-479.
Methods in Molecular Biology: vol. 225, Inflammation Protocols., Winyard, P.G. and Willoughby, D.A., Humana Press, 2003.
Meydan et al., "Inhibition of acute lymphoblastic leukaemia by a Jak-2 inhibitor", Nature, Feb. 1996, 379(6566):645-8.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi et al., "Human Tyrosine Kinase 2 Deficiency Reveals Its Requisite Roles in Multiple Cytokine Signals Involved in Innate and Acquired Immunity", Immunity, 2006, 25:745-55.
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol., Sep. 2010, 85(3):192-9 Epub Jun. 2, 2010.
Mishima et al., "Determination of tear volume and tear flow", Invest Ophthalmol, 1966, 5:264-276.
Mishima, "Some physiological aspects of the precorneal tear film", Arch Ophthalmol, 1965, 73:233-241.
Mitsunobu, "The Use of Diethyl Azodicarboxylate and Triphenylphosphine in Synthesis and Transformation of Natural Products." Synthesis, 1981, (1): 1-28.
Miyata, et al., "Stereospecific nucleophilic addition reactions to olefins.", J. Org. Chem., 1991, 56:6556-6564.
Miyaura et al., "Palladium-Catalyzed Cross-Coupling Reactions of Organoboron Compounds," Chem. Rev., 1995, 95: 2457-2483.
Miyoshi et al., "Interleukin-8 concentrations in conjunctival epithelium brush cytology samples correlate with neutrophil, eosinophil infiltration, and corneal damage", Cornea, 2001, 20:743-7.
Moreland et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty et al., "The synthesis and SAR of 2-amino-pyrrolo[2,3-d]pyrimidines: A new class of Aurora-A kinase inhibitors", Bioorganic and Medicinal Chemistry Letters, 2006, 16(22), 5778-5783.
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan et al, "JAK mutations in high-risk childhood acute lymphoblastic leukemia", Proc Natl Acad Sci USA, 2009, 106:9414-8.
Naka, "The paradigm of IL-6: from basic science to medicine", Arthritis Res., 2002, 4 Suppl 3:S233-42.
Nakagawara, "Trk receptor tyrosine kinases: A bridge between cancer and neural development." Cancer Letters, 2001, 169:107-114.
Nally et al., "Ocular discomfort and tear film break-up time in dry eye patients: A correlation," Invest Ophthalmol Vis Sci, 2000, 41:4:1436 (Poster Presentation).
Naqvi et al., "A potential role of ruxolitinib in leukemia", Expert Opinion on Investigational Drugs, Aug. 2011, 20(8): 1159-1166.

National Cancer Institute, "FDA Approval for Ruxolitinib Phosphate", http://www.cancer.gov/cancertopics/druginfo/fda-ruxolitinibphosphate posted Nov. 18, 2011 (3 pages).
Naus et al., "6-(Het)aryl-7-Deazapurine Ribonucleosides as Novel Potent Cytostatic Agents", J. Med. Chem., 2010, 53(1):460-470.
Neidle Cancer Drug Design and Discovery, (Elsevier/Academic Press, 2008) 427-431.
Nelson et al., "Tear film osmolality determination: an evaluation of potential errors in measurement," Curr Eye Res, 1986, 5(9):677-81.
Neubauer et al., "Jak2 Deficiency Defines an Essential Developmental Checkpoint in Definitive Hematopoiesis", Cell, 1998, 93(3): 397-409.
Nicholoff et al., "Recent Insights into the immunopathogenesis of psoriasis provide new therapeutic opportunities", J. Clin. Invest, 2004, 113: 1664-1675.
Nichols et al., "The lack of association between signs and symptoms in patients with dry eye disease", Cornea, 2004, 23(8):762-770.
Nichols et al., "The repeatability of clinical measurements of dry eye", Cornea, 2004, 23(3):272-85.
Nishio et al., "Tyrosine kinase-dependent modulation by interferon-$\alpha$ of the ATP-sensitive K+ current in rabbit ventricular myocytes", FEBS Letters, 1999, 445: 87-91.
Nitta et al., "Peptide-Titanium Complex as Catalyst for Asymmetric Addition of Hydrogen Cyanide to Aldehyde", J. Am. Chem. Soc., 1992, 114: 7969-75.
Norman, "Selective JAK1 inhibitor and selective Tyk2 inhibitor patents," Expert Opinion, Informa Healthcare. 2012, available at: <http://informahealthcare.com/dol/pdfplus/10.1517/13543776.2012.723693>.
Norn, "Quantitative tear ferning. Clinical investigations", Acta Ophthalmol (Copenh), 1994, 72(3):369-72.
Notice of Allowance and Fee(s) Due dated Sep. 21, 2007 in connection with U.S. Appl. No. 11/313,394 (6 pages).
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702 (9 pages).
Office Action (Non-final) dated Dec. 3, 2007 in connection with U.S. Appl. No. 11/524,641 (13 pages).
Office Action (Non-final) dated Feb. 25, 2009 for U.S. Appl. No. 12/137,892 (13 pgs.)
Office Action (Final) dated Feb. 7, 2008 for U.S. Appl. No. 11/115,702 (5 pages).
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.)
Office Action (Non-final) dated Apr. 20, 2007 in connection with U.S. Appl. No. 11/313,394 (16 pages).
Office Action in U.S. Appl. No. 14/186,338, mailed May 5, 2014, 18 pages.
Office Action received for European Application No. 06 839 328.9 (Jan. 22, 2009) (5 pages).
Office Action received for Japanese Application No. 2008-545733 dated Oct. 11, 2011 (5 pages).
Office Action received for New Zealand Application No. 569015 dated Feb. 24, 2010 (2 pages).
Office Action received for Singapore Application No. 2008-04386-1 (Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012 (3 pages).
Office Action, China, Patent Application No. 201080033308.6 dated Aug. 2, 2013, 10 pages.
Office Action, Eurasian Patent Office, prepared Feb. 5, 2010.
Office Action, European Patent Office, Application No. 06 839 328.9 mailed Oct. 21, 2010.
Office Action, European Patent Office, mailed Nov. 6, 2009, Application 06839328.9.
Office Action, Mexico, Patent Appl. No. MX/a/2008/007635 as received from foreign associate dated Jun. 15, 2010 (1 page).

(56) References Cited

OTHER PUBLICATIONS

Office Action, Mexico, Patent Appl. No. MX/a/2008/007635 as received from foreign associate dated Nov. 13, 2009 (4 pages).
Office Action/Examination Report received for Pakistan Application No. 211/2009 dated Jan. 18, 2010 (1 page).
Oguz et al., "The height and radius of the tear meniscus and methods for examining these parameters", Cornea, 2000, 19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008 1 page letter from Foreign Associate enclosing the translation (5 pages) of the Opposition.
Ortmann et al., "Janus kinases and signal transducers and activators of transcription: their roles in cytokine signaling, development and immunoregulation," Arthritis Res, 2000, 2(1): 16-32.
Ostojic et al., "Ruxolitinib for the treatment of myelofibrosis," Drugs of Today, Nov. 2011, 47(11): 817-827.
Ousler et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer et al., "Multiple roles of ephrins in morphogenesis, neuronal networking, and brain function," Genes & Dev., 2003, 17:1429-1450.
Pardanani, "JAK2 inhibitor therapy in myeloproliferative disorders: rationale, preclinical studies and ongoing clinical trials JAK2 inhibitor therapy in MPD," Leukemia, Jan. 2008, 22: 23-30.
Parganas et al., "Jak2 is Essential for Signaling through a Variety of Cytokine Receptors," Cell, 1998, 93(3): 385-95.
Park et al., "Homogeneous Proximity Tyrosine Kinase Assays: Scintillation Proximity Assay versus Homogeneous Time-Resolved Fluorescence", Analytical Biochemistry, 1999, 269: 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani et al., "Bioisosterism: A Rational Approach in Drug Design", Chem. Rev., 1996, 96: 3147-3176.
Patrick, "An Introduction to medicinal chemistry" *Oxford University Press Inc.*, New York, 1995 (31 pages) (cited in Opposition from India dated Nov. 12, 2012.
Pearce et al., "Spatial location studies on the chemical composition of human tear ferns", Ophthalmic Physiol Opt, 2000, 20(4):306-13.
Pearce et al., "An improved fluorophotometric method for tear turnover assessment", Optom Vis Sci, 2001, 78(1):30-36.
Pensyl et al., "The repeatability of tear mucus ferning grading", Optom Vis Sci, 1998, 75(8):600-4.
Perris et al., "JAK-STAT signaling in asthma." J Clin Invest, 2002, 109(10): 1279-83.
Peters et al., "Functional Significance of Tie2 Signaling in the Adult Vasculature", 2004, © The Endocrine Society (21 pages).
Pflugfelder et al., "Evaluation of subjective assessments and objective diagnostic tests for diagnosing tear-film disorders known to cause ocular irritation," Cornea, 1998, 17(1):38-56.
Pillonel "Evaluation of phenylaminopyrimidines as antifungal protein kinase inhibitors," Pest Management Science, Wiley & Sons, Jun. 2005, 61: 1069-1076.
Pirard et al., "Classification of Kinase Inhibitors Using BCUT Descriptors", J. Chem. Inf. Comput. Sci., 2000, 40: 1431-1440.

Pisella et al., "Flow cytometric analysis of conjunctival epithelium in ocular rosacea and keratoconjunctivitis sicca," Ophthalmology, 2000, 107:1841-1849.
Pisella et al., "Conjunctival proinflammatory and proapoptotic effects of latanoprost, preserved timolol and unpreserved timolol: an ex vivo and in vitro study." Invest Ophthalmol Vis Sci, 2004, 45:1360-1368.
Portnaya et. al., "Azomethine dyes. IV. Indoaniline dyes derived from heterocyclic N-substituted 1-hydroxy-2-naphthamide," Ts Vses Nauchn Issled Kinofotoinst, 1960, Issue 40, 106-8 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Prezent et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quesada et al, "One-pot conversion of activated alcohols into 1,1-dibromoalkenes and terminal alkynes using tandem oxidation processes with manganese dioxide", Tetrahedron, 2006, 62: 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, "Preformulation", Remington's Pharmaceutical Sciences, 17th ed., Mack Publishing Company, Easton, Pa., 1985, Chapter 76, 1409-1423.
Ren et al., "Compounds and Compositions as Protein Kinase Inhibitors," U.S. Appl. No. 60/578,491, filed Jun. 10, 2004 (56 pages).
Response and Amendment dated Aug. 25, 2009 to non-final Office Action for U.S. Appl. No. 12/137,892 (34 pgs.)
Response and Amendment in Reply to Action of Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Roberts et al., "Trends in the Risks and Benefits to Patients With Cancer Participating in Phase 1 Clinical Trials," JAMA, 2004, 292(17):2130-2140.
Robin et al., "In vivo transillumination biomicroscopy and photography of meibomian gland dysfunction," Ophthalmology, 1985, 92:1423-6.
Rodig et al., "Disruption of the Jakl gene demonstrates obligatory and nonredundant roles of the Jaks in cytokine-induced biologic responses." Cell, 1998, 93(3): 373-83.
Rolando et al., "Tear mucus crystallization in children with cystic fibrosis", Ophthalmologica, 1988, 197(4):202-6.
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbock (Texas, USA), Dry Eye Institute, 1986, 203-210.
Rolando et al., "The effect of hyperosmolarity on tear mucus ferning", Fortschr Ophthalmol, 1986, 83:644-646.
Rolando et al., "The Ocular Surface and Tear Film and Their Dysfunction in Dry Eye Disease," Survey of Ophthalmology, Mar. 2001, 45(Supplement 2): S203-S210.

(56) References Cited

OTHER PUBLICATIONS

Rolando, "Tear mucus ferning test in normal and keratoconjunctivitis sicca eyes," Chibret Int J Ophthalmol, 1984, 2(4):32-41.
Roudebush et al., "Pharmacologic manipulation of a four day marine delayed type hyper sensitivity model", Agents Actions, 1993, 38(1-2):116-21.
Rousvoal et al. "Janus kinase 3 inhibition with CP-690,550 prevents allograft vasculopathy", Transpl Int., 2006, 19(12):1014-21.
Saemann et al., "Prevention of CD40-triggered dendritic cell maturation and induction of T-cell hyporeactivity by targeting of Janus kinase 3," Am J Transplant 2003, 3(11): 1341-9.
Saettone et al., "Ocular inserts for topical delivery," Advanced Drug Delivery Reviews, 1995, 16: 95-106.
Samanta et al., "Janus kinase 2: a critical target in chronic myelogenous leukemia," Cancer Res., Jul. 2006, 66(13):6468-72.
Sawada et al, "Increased Lipophilicity and Subsequent Cell Partitioning Decrease Passive Transcellular Diffusion of Novel, Highly Lipophilic Antioxidants", The Journal of Pharmacology and Experimental Therapeutics, 1999, 288(3):1317-1326, p. 1321, compound 26.
Schindler et al., "Hormones and Signaling: Cytokines and STAT Signaling," Adv Pharmacol., 2000, 47:113-74.
Schrader et al., "Animal Models of Dry Eye," Developmental Ophthalmology, 2008, 41: 298-312.
Scott et al., "Jaks, STATs, Cytokines, and Sepsis." Clin Diagn Lab Immunol, 2002, 9(6): 1153-9.
Search Report in TW Application No. 100117866, dated Dec. 2014, 1 page.
Seefeld et al, "Discovery of 5-pyrrolopyridinyl-2-thiophenecarboxamides as potent AKT kinase," Bioorganic & Medicinal Chemistry Letters, 2009, 19(8):2244-2248.
Seela et al., "Synthesis of Pyrrolo[2,3-d]pyrimidine 2', 3'-Dideoxyribenucleosides Related to 2 ',3 '-Dideoxyadenosine and 2',3'-Dideoxgtuanosine and Inhibitor), Activity of 5'-Triphosphates on HIV-1 reverse Transcriptase", Helvetica Chimica Acta, 1991, 74(3), 554-64.
Seki, "STAT3 and MAPK in human lung cancer tissues and suppression of oncogenic growth by JAB and dominant negative STAT3", Int J Oncol., 2004, 24(4):931-4.
Seto et al., "Enhanced Th2 cell-mediated allergic inflammation in Tyk2-deficient mice." J Immunol, 2003, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, Aug. 2002, 2:117-125.
Shi et al., "The pharmacokinetics, pharmacodynamics, and safety of orally dosed INCB018424 phosphate in healthy volunteers", Journal of Clinical Pharmacology, Dec. 2011, 51(12): 1644-1654.
Shimazaki et al., "Meibomian gland dysfunction in patients with Sjogren syndrome", Ophthalmology, 1998, 105(8):1485-8.
Smith et al, "Basic pathogenic mechanisms operating in experimental model acute anterior uveitis," Immunology and Cell Biology, 1998, 76: 497-512.
Smolen et al, "Effect of interleukin-6 receptor inhibition with tocilizumab in patients with rheumatoid arthritis (Option study): a double-blind, placebo-controlled, randomized trial", Lancet, 2008, 371:987.
Sriram et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodegeneration", J. Biol. Chem., 2004, 279(19):19936-47.
Staerk et. al., "JAK1 and Tyk2 activation by the homologous polycythemia vera JAK2 V617F mutation: cross-talk with IGF1 receptor", J Biol Chem., 2005, 280:41893-41899.
State Intellectual Property Office, PR China, Office Action, dated Sep. 3, 2010 Pat. Appl. No. 200680052750.7 (8 pages).

Stirewalt et al., "Predictors of relapse and overall survival in Philadelphia chromosome-positive acute lymphoblastic leukemia after transplantation", Biol Blood Marrow Transplant., Mar. 2003, 9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Sullivan et al., "4th International Conference on the Lacrimal Gland, Tear Film & Ocular Surface and Dry Eye Syndromes, Nov. 20, 2004" (2 pages).
Takahashi et al., "Solvent-Free Reaction Using Phosphonium Salts: Chlorination of Hydroxyheteroaromatics and dehydration of Primary Amides", Heterocycles, 2006, 68: 1973-1979.
Takano et al., "Inflammatory cells in brush cytology samples correlate with the severity of corneal lesions in atopic keratoconjunctivitis", Br J Ophthalmol, 2004, 88:1504-5.
Takemoto et al., "Proliferation of adult T cell leukemia/lymphoma cells is associated with the constitutive activation of JAK/STAT proteins." Proc Natl Acad Sci USA, 1997, 94(25): 13897-902.
Tan et al, "Racemization processes at a quaternary carbon center in the context of the asymmetric Michael reaction", Tetrahedron Lett., 2001, 42(30):5021-5023.
Tang et al., "Knowledge-based design of 7-azaindoles as selective B-Raf inhibitors", Bioorganic & Medicinal Chemistry Letters, 2008, 18(16):4610-4614.
Tasian et al., "Understanding the biology of CRLF2-overexpressing acute lymphoblastic leukemia", Critical Reviews in Oncogenesis, 2011, 16(1): 13-24.
Tefferi et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, "Primary myelofibrosis: 2012 update on diagnosis, risk stratification, and management" American Journal of Hematology, Dec. 2011, 86(12): 1017-1026.
Tefferi et al., "Serious adverse events during ruxolitinib treatment discontinuation in patients with myelofibrosis", Mayo Clinic Proceedings, Dec. 2011, 86(12): 1188-1191.
Thompson et al., "Photochemical Preparation of a Pyridone Containing Tetracycle: A Jak Protein Kinase Inhibitor", Bioorganic & Medicinal Chemistry Letters, 2002, 12: 1219-1223.
Tiffany et al., Meniscectomy using the Tearscope-plus (ARVO abstract). Invest Ophthalmol Vis Sci, 2001,42: s37 (1 page).
Tiffany, "Refractive index of meibomian and other lipids", Curr Eye Res, 1986, 5:887-9.
Ting et al., "The Synthesis of substituted bipiperidine amide compounds as CCR3 antagonists", Bioorg. Med. Chem. Lett., 2005, 15(5): 1375-1378.
Toyonaga, "Blockade of constitutively activated Janus kinase/signal transducer and activator of transcription-3 pathway inhibits growth of human pancreatic cancer", Cancer Lett., 2003, 201(1):107-16.
Tsubota et al., "Brush cytology for the evaluation of dry-eye", Nippon Ganka Gakkai Zasshi, 1990, 94:224-30 (English Abstract).
Tsubota et al., "Conjunctival brush cytology", Acta Cytol, 1990, 34(2):233-5.
Tsubota et al., "Detection by brush cytology of mast cells and eosinophils in allergic and vernal conjunctivitis," Cornea, 1991, 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem., 1985, 50:760-763.
Vaillant et al., "Turbidity of pulpy fruit juice: A key factor for predicting cross-flow microfiltration performance," J Membrane Sci., 2008, 325:404-412.
van Best et al., "Measurement of basal tear turnover using a standardized protocol", Graefe's Arch Olin Exp Ophthalmol, 1995, 233:1-7.

(56) References Cited

OTHER PUBLICATIONS van Bijsterveld, "Diagnostic tests in the sicca syndrome", Arch Ophthalmol, 1969, 82:10-14.
Vannucchi et al., "The mTOR Inhibitor, RAD001, Inhibits the Growth of Cells From Patients with Myeloproliferative Neoplasms", Blood: ASH Annual Meeting Abstracts, 51st Annual Meeting of the American Society of Hematology, 2009, 114(22), 2 pages.
Vannucchi et al., "Inhibitors of PI3K/Akt and/or mTOR Inhibit the Growth of Cells of Myeloproliferative Neoplasms and Synergize with JAK2 Inhibitor and Interferon", Blood, 2011, 118(21): 1638-1639, XP008150742ASH Annual Meeting Abstract 3835 American Society of Hematology.
Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, 114(22), 2 pages.
Vasilevsky et al., "Ethyl Vinyl Ether—an Agent for Protection of the Pyrazole NH-Fragment. A Convenient Method for the Preparation of N-Unsubstituted 6Alkynylpyrazoles", Heterocycles, 2003, 60(4):879-886.
Verma et al., "Jak family of kinases in cancer", Cancer and Metastasis Reviews, 2003, 22(4): 423-434, DOI: 10.1023/A:1023805715476.
Verstovsek, "Therapeutic Potential of JAK2 Inhibitors", Hematology Am Soc Hematol Educ Program, 2009:636-42.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424,"50th ASH Annual Meeting and Exposition, Abstract No. 2802 (2008).
Vitali et al. "The European Community Study Group on diagnostic criteria for Sjogren's syndrome. Sensitivity and specificity of tests for ocular and oral involvement in Sjogren's syndrome," Ann Rheum Dis, 1994, 53(10): 637-47.
Wagh et al., "Polymers used in ocular dosage form and drug delivery systems", Asian J. Pharm., Jan. 2008, 12-17.
WebMD. "Diabetes Health Center." Available at: < http://diabetes.webmd.com/guide/diabetestreatment_care >. 3 pages, retrieved from the Internet May 28, 2013.

Webster's New World Medical Dictionary, Sjogren's syndrome, 2003, Wiley Publishing, printed fro http://www.credoreference.com/entry/webstenned/sjogren_s_syndrome, 2 pages.
Weiss et al., "Evaluation of a Series of Naphthamides as Potent, Orally Active Vascular Endothelial Growth Factor Receptor-2 Tyrosine Kinase Inhibitors", J. Med Chem., 2008, 51:1668-1680.
Welch et al., "An approach to a more standardized method of evaluating tear film break-up time", Invest Ophthalmol Vis Sci, 2003, 2485/B324 (abstract only—2 pages).
White et al., "Human basic tear fluid osmolality. I. Importance of sample collection strategy", Acta Ophthalmol (Copenh), Aug. 1993, 71(4):524-9.
Williams and Ibrahim, "Carbodiimide Chemistry: Recent Advances", Chem. Rev., 1981, 81:589-636.
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wolf et al., "Burger's Medicinal Chemistry and Drug Discovery", 5th Ed. Part I, 1995, 975-977.
Wu et al., One-Pot Two-Step Microwave-Assisted Reaction in Construction 4,5-Disubstituted Pyrazolopyrimidines Organic Letters, 2003, 5(20): 3587-3590.
Wuts and Greene, Protective Groups in Organic Synthesis, 4th ed., John Wiley & Sons: New Jersey, 2007.
Yamaoka et al., "Janus kinase (JAK) inhibitors in rheumatoid arthritis", Current Rheumatology Reviews, Nov. 2011, 7(4): 306-312.
Yang et al., "Constitutive NF-KB activation confers interleukin 6 (IL6) independence and resistance to dexamethasone and Janus kinase inhibitor INCB018424 in murine plasmacytoma cells", Journal of Biological Chemistry, Aug. 2011, 286(32):27988-27997.
Yao et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 2008, 58(11):3485-3497.
Yao, et al., "Glucocorticoid Excess in Mice Results in Early Activation of Osteoclastogenesis and Adipogenesis and Prolonged Suppression of Osteogenesis", Arthritis and Rheumatism, 2008, 58(6), 1674-1686.
Yokoi et al., "A newly developed video-meibography system featuring a newly designed probe", Jpn J Ophthalmol, 2007, 51: 53-6.
Yokoi et al., "Assessment of meibomian gland function in dry eye using meibometry", Arch Ophthalmol, 1999, 117:723-9.
Yokoi et al., "Correlation of tear lipid layer interference patterns with the diagnosis and severity of dry eye", Am J Ophthalmol, 1996, 122:818-24.
Yokoi et al., "Non-invasive methods of assessing the tear film", Exp Eye Res, 2004, 78:399-407.
Yu et al., "Constitutive activation of the Janus kinase-STAT pathway in T lymphoma overexpressing the Lck protein tyrosine kinase," J Immunol., 1997, 159(11):5206-10.
Zheng et al., "Discovery of INCB108201PF-4178903, a potent, selective, and orally bioavailable dual CCR2 and CCR5 antagonist", Bioorganic & Medicinal Chemistry Letters, 2011, 21: 1442-45.
Zoppellaro et al., "A Multifunctional High-Spin Biradical Pyrazolylbipyridine-bisnitronylnitroxide", Org. Lett., 2004, 6(26):4929-4932.
Zou et al., "Signaling Pathways Activated by Oncogenic Forms of Abl Tyrosine Kinase." Journal of Biological Chemistry, 1999, 274(26):18141-18144.

* cited by examiner

PROCESSES OF PREPARING A JAK1 INHIBITOR AND NEW FORMS THERETO

This application claims the benefit of priority of Ser. No. 61/986,738, filed Apr. 30, 2014, and Ser. No. 61/986,789, filed Apr. 30, 2014, each of which is incorporated herein by reference in its entirety.

TECHNICAL FIELD

This invention relates to processes for preparing a JAK1 inhibitor, as well as new forms of the inhibitor.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1−/− mice are runted at birth, fail to nurse, and die perinatally (Rodig, S. J., M. A. Meraz, et al. (1998) *Cell* 93(3): 373-83). Jak2−/− mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol.* 2000; 47:113-74).

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY

The present invention provides process of preparing a compound of Formula Ia:

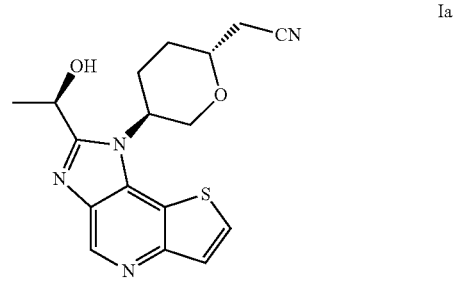 [SMILES: C[C@@H](O)c1nc2cnc3ccsc3c2n1[C@H]1CC[C@H](CC#N)OC1]

Ia comprising reacting a compound of Formula Ib:

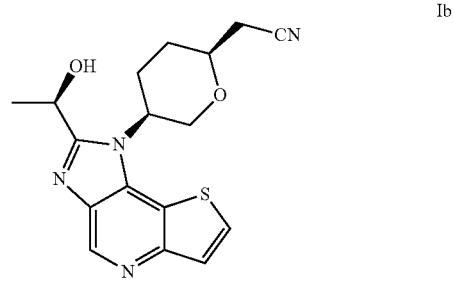 [SMILES: C[C@@H](O)c1nc2cnc3ccsc3c2n1[C@H]1CC[C@@H](CC#N)OC1]

Ib with a strong base in the presence of a first solvent component.

The present application provides an anhydrous form of 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile.

The present application also provides a monohydrate form of 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile.

The present application further provides various intermediates useful in the synthesis of the compound of Formula Ia.

DETAILED DESCRIPTION

The present invention provides, inter alia, processes and intermediates for making 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile, which is a compound Formula Ia:

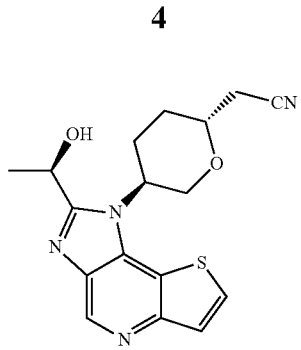

as well as new forms of the compound of Formula Ia. The compound of Formula Ia includes anhydrous and hydrated forms of the compound. For example, the present application provides a new anhydrous form and a new monohydrate form of the compound of Formula Ia. The monohydrate form has Formula II:

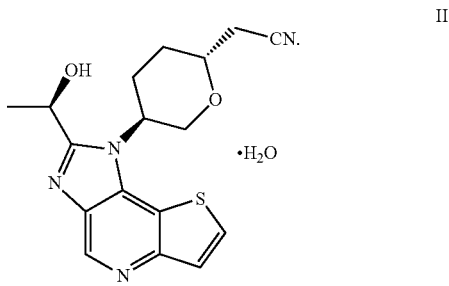

The present application provides an anhydrous form of 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile.

In some embodiments, the anhydrous form is substantially isolated. In some embodiments, the anhydrous form is crystalline.

Figure 1:
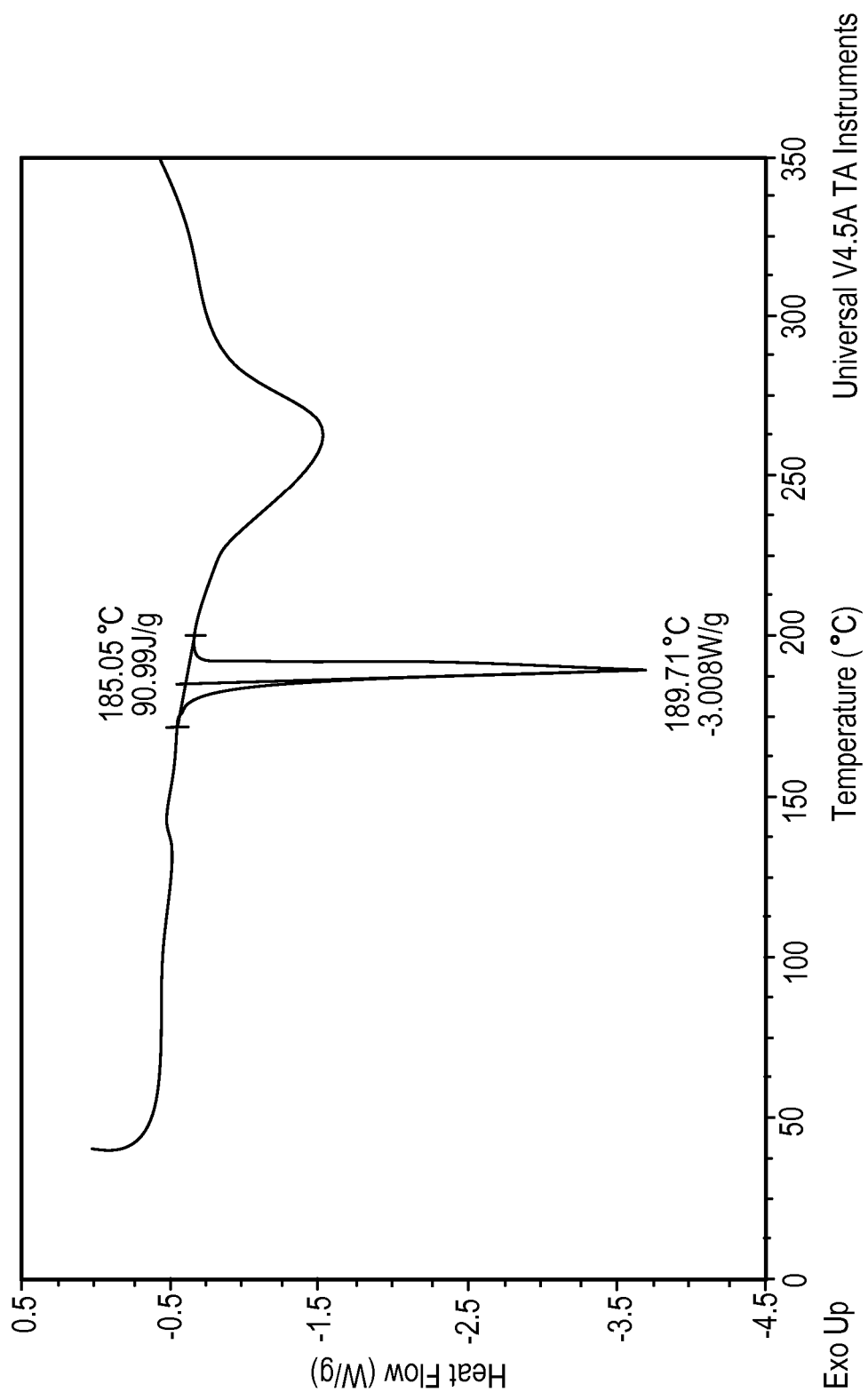
FIG. 1 shows a DSC thermogram characteristic of the compound of Example 9.

In some embodiments, the anhydrous form is characterized by a differential scanning cal thermogram having an endothermic peak having an onset at about 185° C. In some embodiments, the anhydrous form is characterized by a differential scanning calorimetry (DSC) thermogram having an endothermic peak at about 190° C. In some embodiments, the anhydrous form has a DSC thermogram substantially as shown in FIG. 1.

Figure 2:
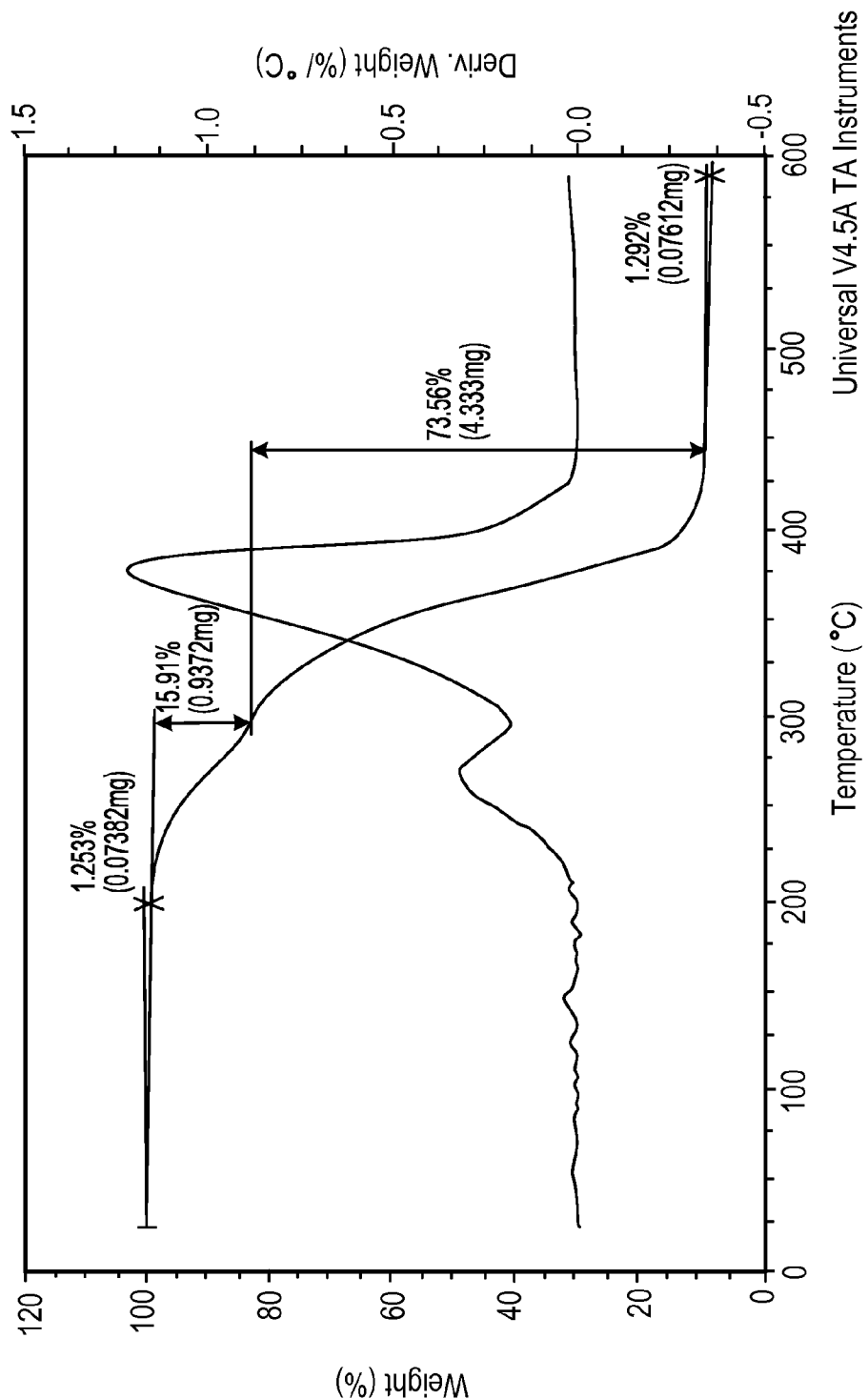
FIG. 2 shows a TGA thermogram characteristic of the compound of Example 9.

In some embodiments, the anhydrous form is characterized by a thermogravimetric analysis (TGA) thermogram having a weight loss of about 1.25% up to 200° C. In some embodiments, the anhydrous form has a TGA thermogram substantially as shown in FIG. 2.

In some embodiments, the anhydrous form has at least one XRPD peak, in terms of 2-theta, selected from about 8.8°, about 10.5°, about 16.3°, about 17.5°, about 19.1°, about 21.2°, about 24.0°, and about 26.4°. In some embodiments, the anhydrous form has at least two XRPD peaks, in terms of 2-theta, selected from about 8.8°, about 10.5°, about 16.3°, about 17.5°, about 19.1°, about 21.2°, about 24.0°, and about 26.4°. In some embodiments, the anhydrous form has at least three XRPD peaks, in terms of 2-theta, selected from about 8.8°, about 10.5°, about 16.3°, about 17.5°, about 19.1°, about 21.2°, about 24.0°, and about 26.4°. In some embodiments, the anhydrous form has at least four XRPD peaks, in terms of 2-theta, selected from about 8.8°, about 10.5°, about 16.3°, about 17.5°, about 19.1°, about 21.2°, about 24.0°, and about 26.4°. In some embodiments, the anhydrous form has at least four XRPD peaks, in terms of 2-theta, selected from about 8.8°, about 16.3°, about 19.1°, about 24.0°, and about 26.4°.

Figure 3:
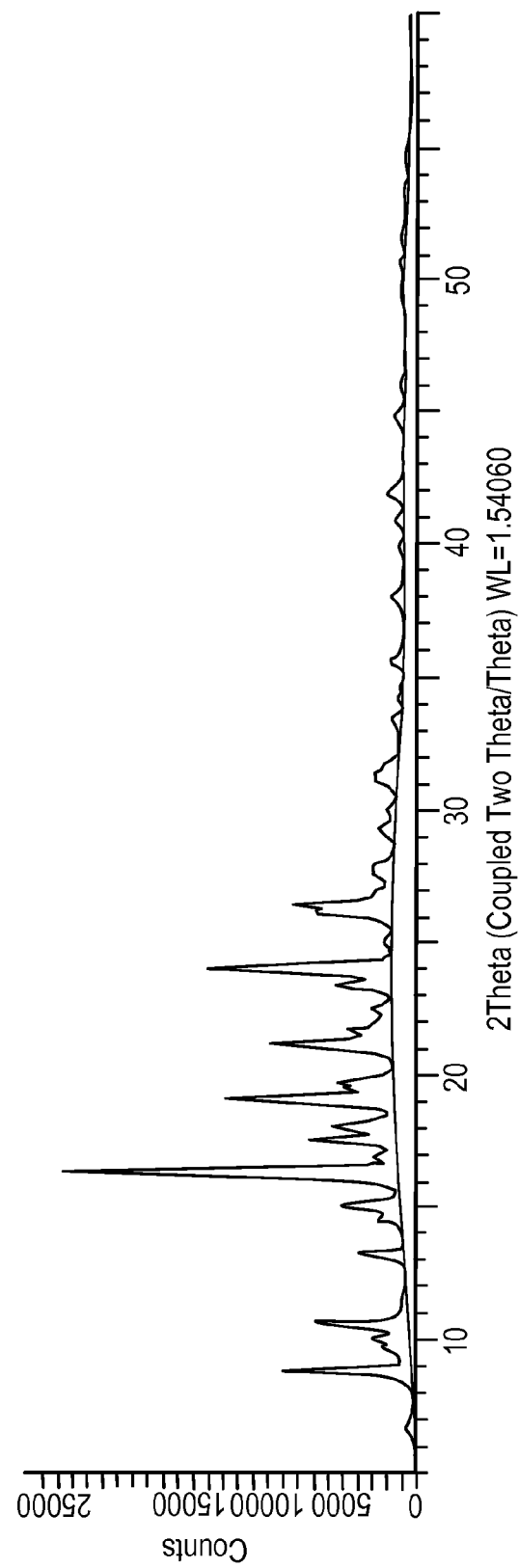
FIG. 3 shows an XRPD pattern characteristic of the compound of Example 9.
Figure 7:
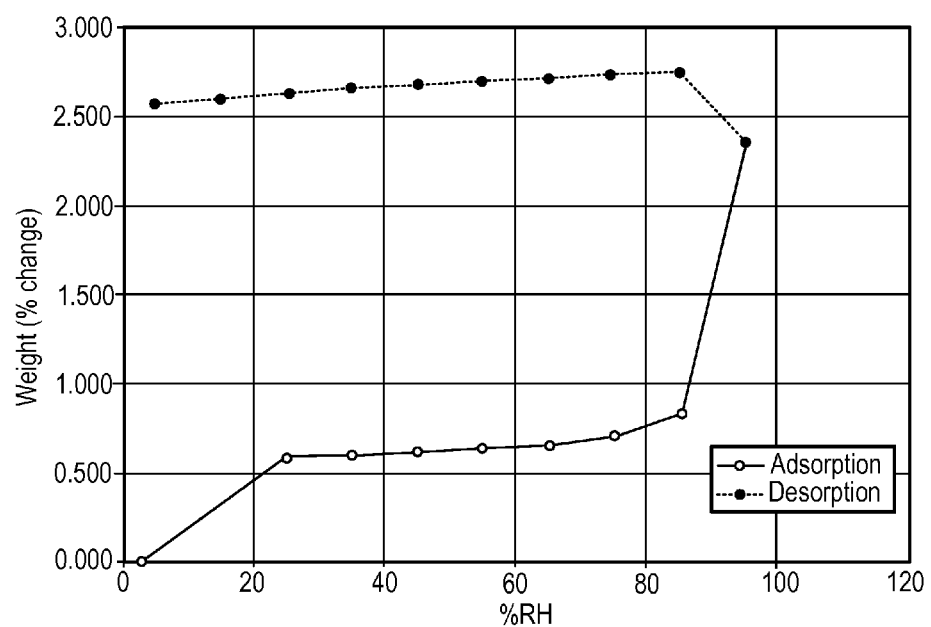
FIG. 7 shows a Vapor Sorption/Desorption Isotherm (1$^{st}$ cycle) characteristic of the compound of Example 9.
Figure 8:
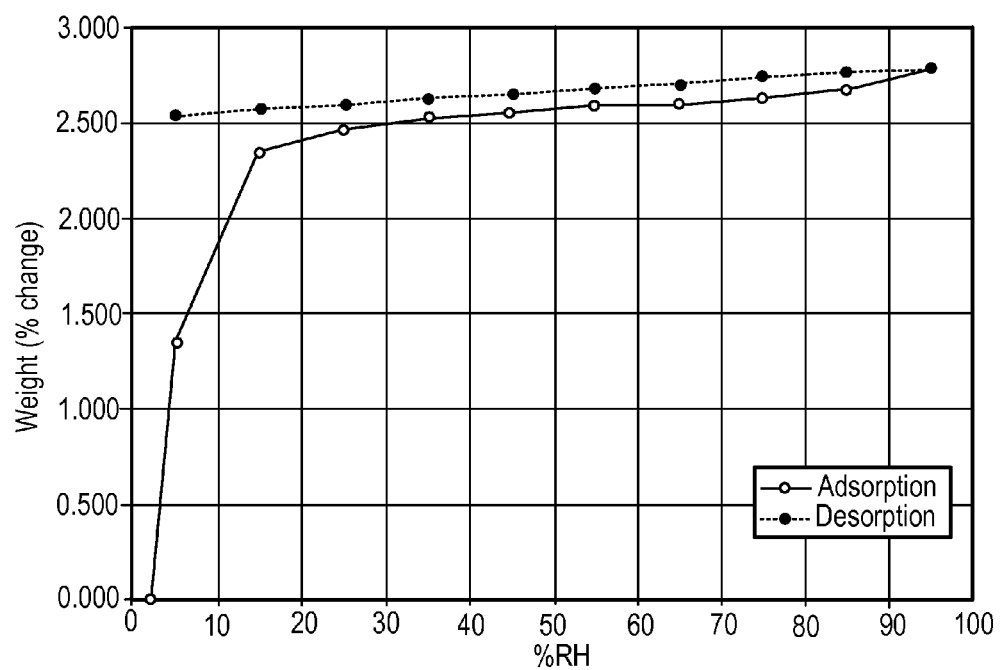
FIG. 8 shows a Vapor Sorption/Desorption Isotherm (4$^{th}$ cycle) characteristic of the compound of Example 9.

In some embodiments, the anhydrous form has an XRPD pattern substantially as shown in FIG. 3. In some embodiments, the anhydrous form has a Vapor Sorption/Desorption Isotherm substantially as shown in FIG. 7. In some embodiments, the anhydrous form has a Vapor Sorption/Desorption Isotherm substantially as shown in FIG. 8.

The present application also provides a monohydrate form of 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile monohydrate, which is a compound of Formula II:

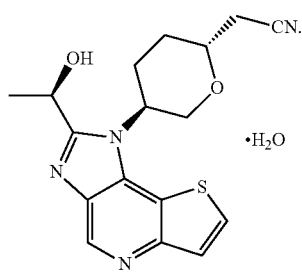

II

In some embodiments, the monohydrate form has a water content of about 5%. In some embodiments, the monohydrate form is substantially isolated. In some embodiments, the monohydrate form is crystalline.

In some embodiments, the monohydrate form is characterized by a DSC thermogram having an endothermic peak having an onset at about 69° C. In some embodiments, the monohydrate form is characterized by a DSC thermogram having an endothermic peak at about 106° C.

Figure 4:
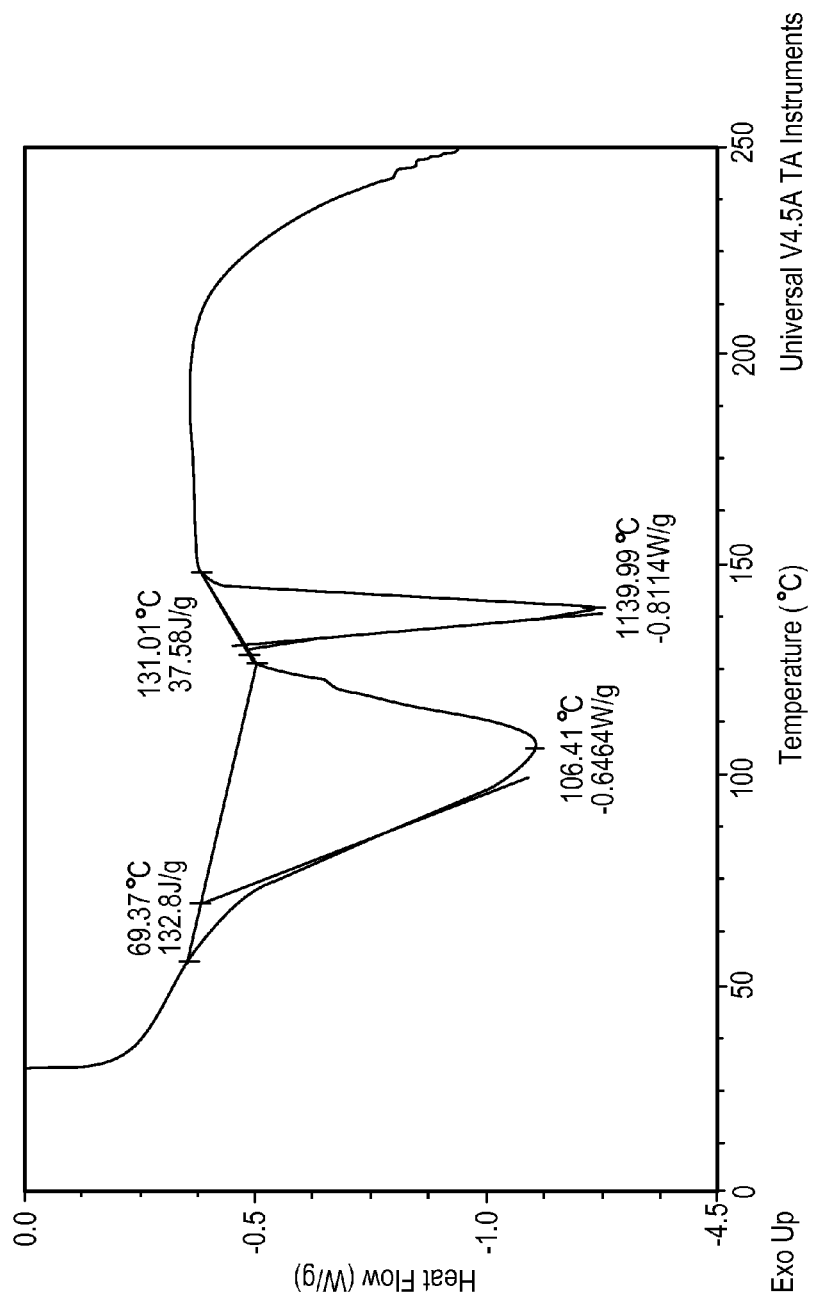
FIG. 4 shows a DSC thermogram characteristic of the compound of Example 10.

In some embodiments, the monohydrate form is characterized by a DSC thermogram having an endothermic peak having an onset at about 131° C. In some embodiments, the monohydrate form is characterized by a DSC thermogram having an endothermic peak at about 140° C. In some embodiments, the monohydrate form has a DSC thermogram substantially as shown in FIG. 4.

Figure 5:
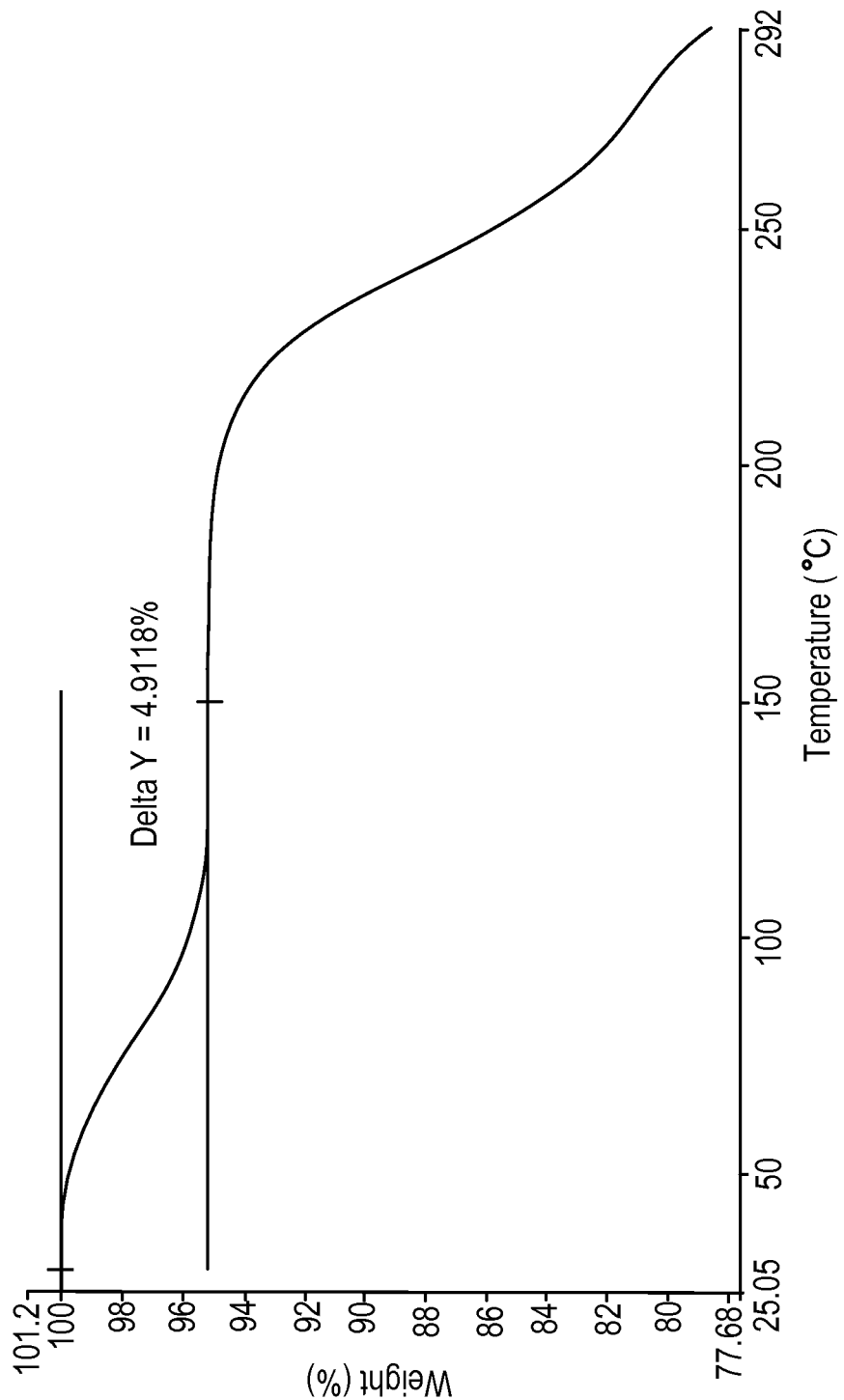
FIG. 5 shows a TGA thermogram characteristic of the compound of Example 10.

In some embodiments, the monohydrate form is characterized by a TGA thermogram having a weight loss of about 5% up to about 150° C. In some embodiments, the monohydrate form has a TGA thermogram substantially as shown in FIG. 5.

Figure 6:
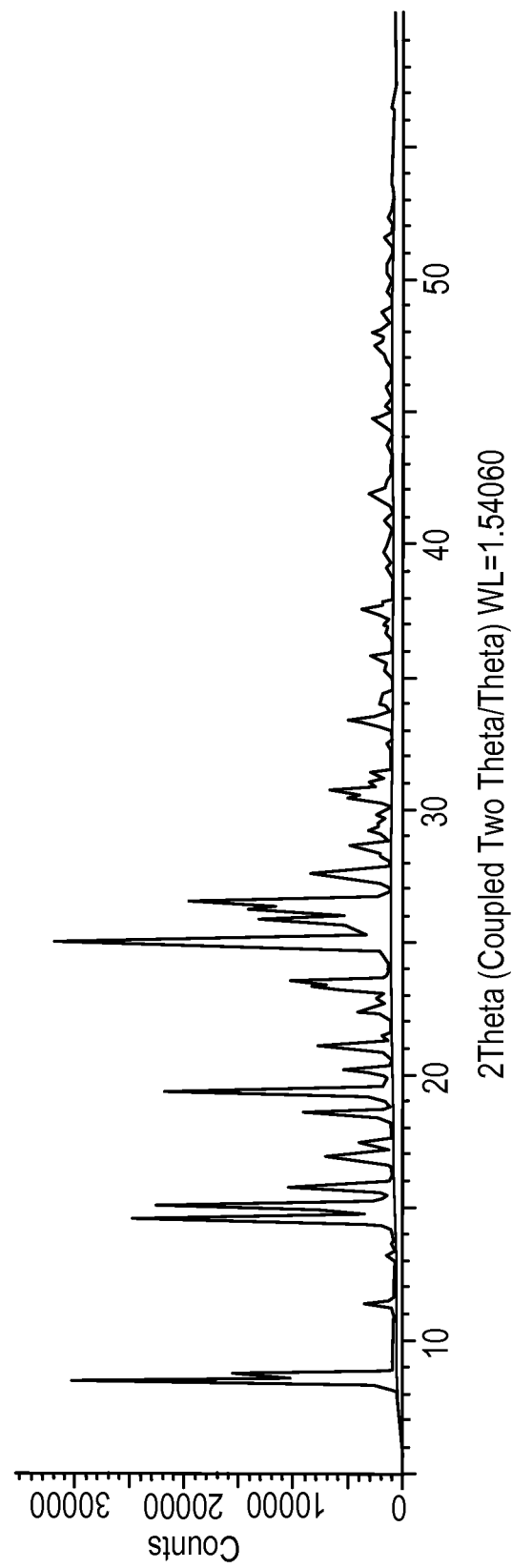
FIG. 6 shows an XRPD pattern characteristic of the compound of Example 10.

In some embodiments, the monohydrate form has at least one XRPD peak, in terms of 2-theta, selected from about 8.5°, about 8.7°, about 14.6°, about 15.1°, about 19.4°, about 25.1°, and about 26.5°. In some embodiments, the monohydrate form has at least two XRPD peaks, in terms of 2-theta, selected from about 8.5°, about 8.7°, about 14.6°, about 15.1°, about 19.4°, about 25.1°, and about 26.5°. In some embodiments, the monohydrate form has at least three XRPD peaks, in terms of 2-theta, selected from about 8.5°, about 8.7°, about 14.6°, about 15.1°, about 19.4°, about 25.1°, and about 26.5°. In some embodiments, the monohydrate form has at least four XRPD peaks, in terms of 2-theta, selected from about 8.5°, about 8.7°, about 14.6°, about 15.1°, about 19.4°, about 25.1°, and about 26.5°. In some embodiments, the monohydrate form has an XRPD pattern substantially as shown in FIG. 6.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

The present application further provides a process of forming the anhydrous form of 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile, comprising:

(i) adding n-heptane to a first mixture comprising a compound of Formula II:

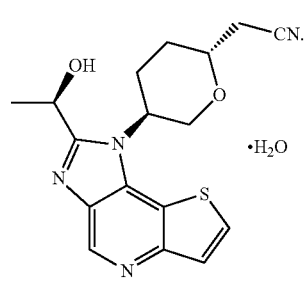

II and a first solvent component, wherein the first solvent component comprises ethyl acetate.

In some embodiments, the first solvent component further comprises methanol.

In some embodiments, the process further comprises before (i):

(ii) dissolving the compound of Formula II in methanol to form a second mixture comprising the compound of Formula Ia and a second solvent component comprising methanol;

(iii) polish filtering the second mixture; and (iv) adding ethyl acetate to the second mixture to form the first mixture.

In some embodiments, the process further comprises heating the first mixture to a temperature from about 60° C. to about 75° C.

In some embodiments, the process further comprises removing at least a portion of the ethyl acetate and methanol to form the first mixture via distillation.

The present application further provides a process of preparing a compound of Formula Ia:

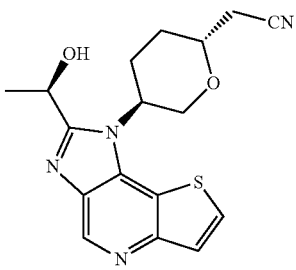

comprising reacting a compound of Formula Ib:

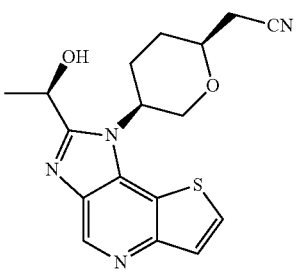

with a strong base in the presence of a first solvent component.

In some embodiments, the strong base is an alkoxide base.

In some embodiments, the strong base is an alkali metal $C_{1-6}$ alkoxide.

In some embodiments, the strong base is potassium tert-butoxide.

In some embodiments, the first solvent component comprises isopropyl alcohol.

In some embodiments, the first solvent component comprises isopropyl alcohol and tetrahydrofuran.

In some embodiments, the reacting of the composition with the strong base is conducted at a temperature of about room temperature.

In some embodiments, wherein about 0.05 to about 0.15 equivalents of strong base is used based on 1 equivalent of the compound of Formula Ib.

In some embodiments, the compound of Formula Ib is present in a composition comprising the compound of Formula Ib and the compound of Formula Ia prior to said reacting of said compound of Formula Ib with said strong base.

In some embodiments, the strong base that is reacted with a compound of Formula Ib is referred to as a first strong base.

In some embodiments, the compound of Formula Ia is prepared as a compound of Formula II:

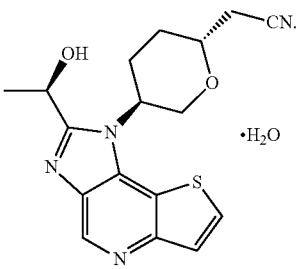

In some embodiments, the composition comprising a compound of Formula Ia and a compound of Formula Ib is prepared by a process comprising reacting a composition comprising a compound of Formula IIIa and a compound of Formula IIIb:

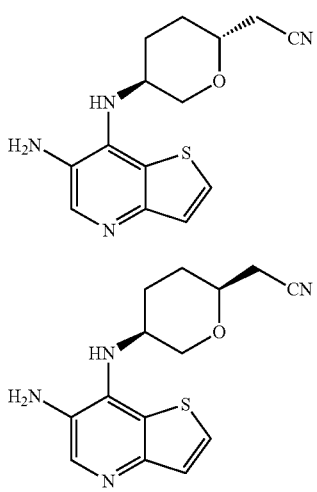

with a compound of Formula IV:

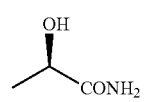

in the presence of a $C_{1-6}$ alkyloxonium reagent and a second solvent component.

In some embodiments, before reacting, the compound of Formula IV is reacted with said $C_{1-6}$ alkyloxonium reagent in the second solvent component.

In some embodiments, the reacting step is referred to as the reacting of a composition comprising a compound of Formula IIIa and a compound of Formula IIIb.

In some embodiments, the $C_{1-6}$ alkyloxonium reagent is triethyloxonium tetrafluoroborate.

In some embodiments, the second solvent component comprises ethanol.

In some embodiments, the second solvent component comprises tetrahydrofuran.

In some embodiments, the second solvent component comprises ethanol and tetrahydrofuran.

In some embodiments, the reacting of the composition of the compound of Formula IIIa and the compound of Formula IIIb with the compound of Formula IV is conducted at a temperature at reflux.

In some embodiments, about 2 to about 4 equivalents of the compound of Formula IV is used based on 1 equivalent of the combined amount of the compound of Formula IIIa and the compound of Formula IIIb.

In some embodiments, about 2 to about 4 equivalents of the alkyloxonium reagent is used based on 1 equivalent of the combined amount of the compound of Formula IIIa and the compound of Formula IIIb.

In some embodiments, the composition comprising a compound of Formula IIIa and a compound of Formula IIIb is prepared by a process comprising reacting a composition comprising a compound of Formula Va and a compound of Formula Vb:

Va

Vb with hydrogen gas in the presence of a hydrogenation catalyst and a third solvent component.

In some embodiments, the hydrogenation catalyst is palladium on carbon.

In some embodiments, the third solvent component comprises 2,2,2-trifluoroethanol.

In some embodiments, the reacting is run at a temperature from about 20° C. to about 35° C.

In some embodiments, the reacting step is referred to as the reacting of a composition comprising a compound of Formula Va and a compound of Formula Vb.

In some embodiments, about 5 to about 15 weight % of the hydrogenation catalyst is used based on total mass of the compound of Formula Va and the compound of Formula Vb.

In some embodiments, the composition comprising a compound of Formula Va and a compound of Formula Vb is prepared by a process comprising reacting a compound of Formula VI:

VI or a salt thereof, with a compound of Formula VII:

VII in the presence of an tertiary amine base and a fourth solvent component, wherein:

X is a halo group.

In some embodiments, the compound of Formula VI, or salt thereof, is a salt of Formula VIa:

VIa

In some embodiments, X is chloro.

In some embodiments, the tertiary amine base is N-ethyl-N-isopropylpropan-2-amine.

In some embodiments, the tertiary amine base that is present in the reaction of the compound of Formula VI is referred to as a first tertiary amine base.

In some embodiments, the fourth solvent component comprises N,N-dimethylformamide.

In some embodiments, the reacting is run at a temperature from about 65° C. to about 75° C.

In some embodiments, the reacting step is referred to as the reacting of a compound of Formula VI.

In some embodiments, the compound of Formula VI, or salt thereof, is a salt of Formula VIa:

VIa the fourth solvent component comprises N,N-dimethylformamide;

the tertiary amine base is N-ethyl-N-isopropylpropan-2-amine; and

X is chloro.

The present application further provides a process of preparing a compound of Formula VI, comprising reacting a compound of Formula VIII:

VIII under deprotection conditions to form the compound of Formula VI, or a salt thereof;

wherein $P^1$ is an amine protecting group.

In some embodiments, $P^1$ is t-butoxycarbonyl.

In some embodiments, the deprotection conditions involve reacting the compound of Formula VIII with a strong acid.

In some embodiments, the strong acid is HCl.

In some embodiments, the strong acid that is reacted with a compound of Formula VIII is referred to as a first strong acid.

In some embodiments, the reacting is run at a temperature from about 0° C. to about 40° C.

In some embodiments, the reacting step is referred to as the reacting of a compound of Formula VIII.

In some embodiments, the compound of Formula VIII is prepared by a process comprising reacting a compound of Formula IX:

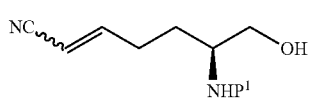

in the presence of a strong base and a fifth solvent component, wherein ∿∿ indicates a cis- or trans-bond; and $P^1$ is an amine protecting group. In some embodiments, the $P^1$ is t-butoxycarbonyl.

In some embodiments, the strong base is a $C_{1-6}$ alkoxide base.

In some embodiments, the alkoxide base is an alkali metal $C_{1-6}$ alkoxide.

In some embodiments, the alkoxide base is sodium methoxide.

In some embodiments, the strong base is present in a catalytic amount.

In some embodiments, the catalytic amount comprises about 0.010 to about 0.020 equivalents of the strong base based on 1 equivalent of the compound of Formula IX.

In some embodiments, the strong base that is present in the reaction of the compound of Formula IX is referred to as a second strong base.

In some embodiments, the fifth solvent component comprises tetrahydrofuran.

In some embodiments, the reacting is run at a temperature from about 0° C. to 5° C.

In some embodiments, the reacting step is referred to as the reacting of a compound of Formula IX.

In some embodiments, the compound of Formula IX is prepared by a process comprising reacting a compound of Formula X:

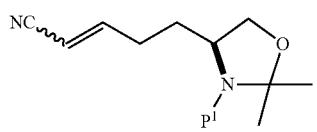

in the presence of a strong acid and a sixth solvent component, wherein ∿∿ indicates a cis- or trans-bond; and $P^1$ is an amine protecting group. In some embodiments, $P^1$ is t-butoxycarbonyl.

In some embodiments, the strong acid is p-toluenesulfonic acid.

In some embodiments, the strong acid is present in a catalytic amount.

In some embodiments, the catalytic amount comprises about 0.005 to about 0.015 equivalents of the strong acid based on 1 equivalent of the compound of Formula X.

In some embodiments, the strong acid that is present in the reaction of the compound of Formula X is referred to as a second strong acid.

In some embodiments, the sixth solvent component comprises methanol.

In some embodiments, the reacting of the compound of Formula X in the presence of the strong acid is run at a temperature of about room temperature.

In some embodiments, the compound of Formula X is prepared by a process comprising:

(i) reacting a compound of Formula XII:

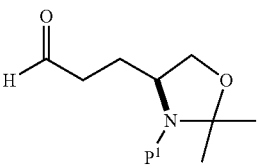

with a Wittig reagent in the presence of a seventh solvent component, wherein said Wittig reagent is prepared by a process comprising reacting a compound of Formula XXI:

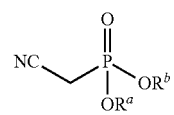

in the presence of a strong base, wherein $R^a$ and $R^b$ are each independently $C_{1-6}$ alkyl; and $P^1$ is an amine protecting group. In some embodiments, $P^1$ is t-butoxycarbonyl.

In some embodiments, before (i), the compound of Formula XXI is reacted with the strong base in said second solvent component.

In some embodiments, $R^a$ and $R^b$ are each ethyl.

In some embodiments, the strong base is potassium tert-butoxide.

In some embodiments, the strong base that is present in the reaction of the compound of Formula XXI is referred to as a base.

In some embodiments, the seventh solvent component comprises tetrahydrofuran.

In some embodiments, the reacting is run at a temperature at about 0° C. to about 5° C.

In some embodiments, the reacting step is referred to as the reacting of a compound of Formula XII.

In some embodiments, about 1.0 to about 2.0 equivalents of the compound of Formula XXI is used based on 1 equivalent of the compound of Formula XII.

In some embodiments, the compound of Formula XII is prepared by a process comprising oxidizing a compound of Formula XIII:

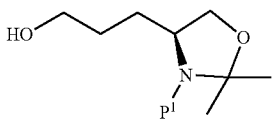

XIII wherein P¹ is an amine protecting group. In some embodiments, P¹ is t-butoxycarbonyl.

In some embodiments, the oxidizing comprises adding a first oxidizing agent to the compound of Formula XIII to form a first mixture.

In some embodiments, the first oxidizing agent is 2,2,6,6-tetramethyl-1-piperidinyloxy free radical (TEMPO).

In some embodiments, the adding of said first oxidizing agent is conducted in the presence of tetra-N-butylammonium chloride.

In some embodiments, the adding of said first oxidizing agent is run at a temperature of about room temperature.

In some embodiments, the oxidizing further comprises adding a base and a second oxidizing agent to said first mixture.

In some embodiments, the second oxidizing agent is an N-halosuccinimide compound.

In some embodiments, the second oxidizing agent is N-chlorosuccinimide.

In some embodiments, the compound of Formula XIII is prepared by a process comprising reacting a compound of Formula XV:

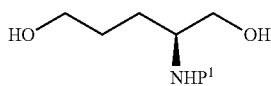

XV with a compound of Formula XIV:

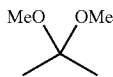

XIV in the presence of boron trifluoride diethyl etherate and an eighth solvent component, wherein P¹ is an amine protecting group. In some embodiments, P¹ is t-butoxycarbonyl.

In some embodiments, the eighth solvent component comprises acetone.

In some embodiments, the reacting is run at a temperature of about room temperature.

In some embodiments, the compound of Formula XV is prepared by a process comprising reacting a compound of Formula XVI:

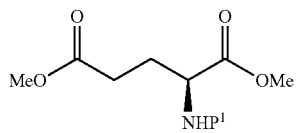

XVI in the presence of a reducing agent and a ninth solvent component, wherein P¹ is an amine protecting group. In some embodiments, P¹ is t-butoxycarbonyl.

In some embodiments, the reducing agent is lithium borohydride.

In some embodiments, the reducing agent that is present in the reaction of the compound of Formula XVI is referred to as a first reducing agent.

In some embodiments, the ninth solvent component comprises tetrahydrofuran.

In some embodiments, the reacting is run at a temperature from about 0° C. to about 40° C.

In some embodiments, the reacting step is referred to as the reacting of a compound of Formula XVI.

In some embodiments, the compound of Formula VIII is prepared by a process comprising reacting a compound of Formula XVII:

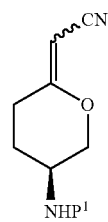

XVII with hydrogen gas in the presence of a hydrogenation catalyst and a tenth solvent component;
wherein P¹ is an amine protecting group.

The ∼ group in Formula XVII indicates that the CN group can be E or Z relative to the oxygen of the pyran ring. In some embodiments, P¹ is t-butoxycarbonyl.

In some embodiments, the hydrogenation catalyst is palladium on carbon.

In some embodiments, about 5 to about 15 weight % of the hydrogenation catalyst is used based on total mass of the compound of Formula XVII.

In some embodiments, the tenth solvent component comprises methanol.

In some embodiments, the compound of Formula XVII is prepared by
(i) reacting a compound of Formula XVIII:

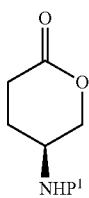

XVIII with a Wittig reagent in the presence of an eleventh solvent component, wherein said Wittig reagent is prepared by a process comprising reacting a compound of Formula XXII:

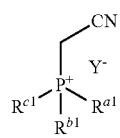

XXII with a strong base, wherein:

$R^{a1}$, $R^{b1}$, and $R^{c1}$ are each independently $C_{1-6}$ alkyl;

$Y^-$ is a halide ion; and $P^1$ is an amine protecting group.

In some embodiments, $P^1$ is t-butoxycarbonyl.

In some embodiments, $Y^-$ is $Cl^-$.

In some embodiments, $R^{a1}$, $R^{b1}$, and $R^{c1}$ are each methyl.

In some embodiments, $R^{a1}$, $R^{b1}$, and $R^{c1}$ are each n-butyl.

In some embodiments, the strong base is potassium tert-butoxide.

In some embodiments, the strong base is lithium hexamethyldisilazide.

In some embodiments, the strong base that is reacted with a compound of Formula XXII is referred to as a fourth strong base.

In some embodiments, the eleventh solvent component comprises tetrahydrofuran.

In some embodiments, the eleventh solvent component comprises N,N-dimethylacetamide.

In some embodiments, the eleventh solvent component comprises tetrahydrofuran and N,N-dimethylacetamide.

In some embodiments, the compound of Formula XVIII is formed by a process comprising reacting a compound of Formula XIX:

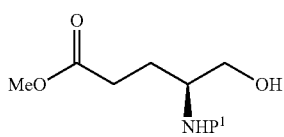

XIX in the presence of a weak organic acid and a twelfth solvent component, wherein $P^1$ is an amine protecting group. In some embodiments, $P^1$ is t-butoxycarbonyl.

In some embodiments, the weak organic acid is acetic acid.

In some embodiments, the twelfth solvent component comprises toluene.

In some embodiments, the reacting is run at a temperature at reflux.

In some embodiments, the reacting step is referred to as the reacting of a compound of Formula XIX.

In some embodiments, the compound of Formula XIX is formed by a process comprising:

(i) reacting a compound of Formula XX:

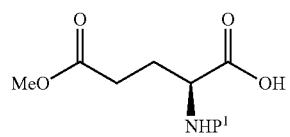

XX with a compound of Formula XXIII:

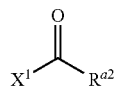

XXIII in the presence of an amine base and an thirteenth solvent component to form a compound of Formula XXIV:

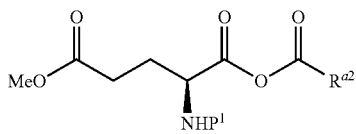

XXIV wherein $R^{2a}$ is $C_{1-4}$ alkoxy;

$X^1$ is halo; and $P^1$ is an amine protecting group.

In some embodiments, $P^1$ is t-butoxycarbonyl.

In some embodiments, the compound of Formula XXIII is ethyl chloroformate.

In some embodiments, the amine base is N-methylmorpholine.

In some embodiments, the amine base that is present in the reaction of the compound of Formula XX is referred to as a second tertiary amine base.

In some embodiments, the thirteenth solvent component comprises tetrahydrofuran.

In some embodiments, the reacting is run at a temperature at about 0° C.

In some embodiments, the reacting step is referred to as the reacting of a compound of Formula XX.

In some embodiments, the process further comprises reducing said compound of Formula XXIV with a reducing agent.

In some embodiments, the reducing agent is sodium borohydride.

In some embodiments, the reducing agent is dissolved in a fourteenth solvent component.

In some embodiments, the reducing agent that is present in the reducing of the compound of Formula XXIV is referred to as a second reducing agent.

In some embodiments, the fourteenth solvent component comprises diglyme.

In some embodiments, the reducing is run at a temperature from about 70° C. to about 80° C.

In some embodiments, the reducing step is referred to as the reducing of a compound of Formula XXIV.

In some embodiments, the composition comprising a compound of Formula Ia and a compound of Formula Ib is prepared by a process comprising reacting a composition comprising a compound of Formula IIIa and a compound of Formula IIIb:

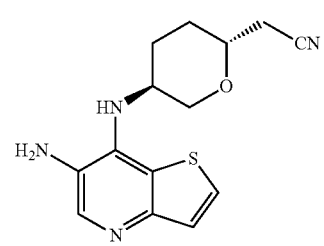

IIIa

-continued

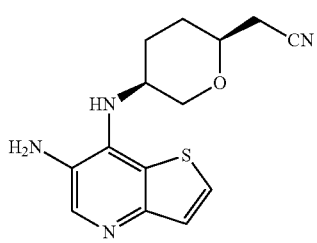

with (R)-4-methoxy-2,2,5-trimethyl-2,5-dihydrooxazole:

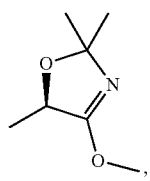

or a salt thereof.

In some embodiments, the reacting a composition comprising a compound of Formula IIIa and a compound of Formula IIIb is performed at a temperature from about 60° C. to about 70° C.

In some embodiments, the reacting a composition comprising a compound of Formula IIIa and a compound of Formula IIIb is performed in the presence of a fifteenth solvent component.

In some embodiments, the fifteenth solvent component comprises methanol.

In some embodiments, the (R)-4-methoxy-2,2,5-trimethyl-2,5-dihydrooxazole is prepared by reacting (R)-2,2,5-trimethyloxazolidin-4-one:

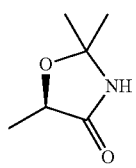

with trimethyloxonium tetrafluoroborate.

In some embodiments, about 1 equivalent of trimethyloxonium tetrafluoroborate is used based on 1 equivalent of (R)-2,2,5-trimethyloxazolidin-4-one.

In some embodiments, the reacting of (R)-2,2,5-trimethyloxazolidin-4-one is performed at about room temperature.

In some embodiments, the reacting of (R)-2,2,5-trimethyloxazolidin-4-one is performed in the presence of a sixteenth solvent component.

In some embodiments, the sixteenth solvent component comprises anhydrous dichloromethane.

In some embodiments, the steps of reacting (R)-2,2,5-trimethyloxazolidin-4-one with trimethyloxonium tetrafluoroborate to form (R)-4-methoxy-2,2,5-trimethyl-2,5-dihydrooxazole and reacting (R)-4-methoxy-2,2,5-trimethyl-2,5-dihydrooxazole with a composition comprising a compound of Formula IIIa and a compound of Formula IIIb are conducted in the same pot without isolation of (R)-4-methoxy-2,2,5-trimethyl-2,5-dihydrooxazole.

In some embodiments, the composition comprising a compound of Formula Ia and a compound of Formula Ib is prepared by a process comprising reacting a composition comprising a compound of Formula IIIa and a compound of Formula IIIb:

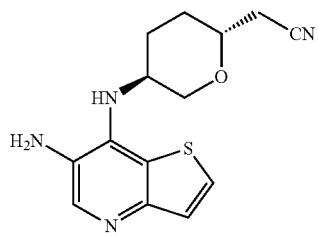

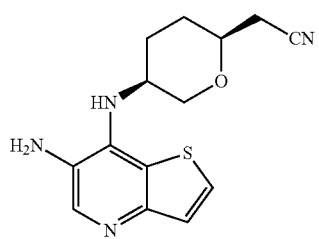

with (R)-ethyl 2-hydroxypropanimidate:

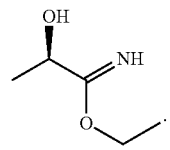

In some embodiments, the reacting a composition comprising a compound of Formula IIIa and a compound of Formula IIIb is performed at a temperature from about 75° C. to about 85° C.

In some embodiments, the composition comprising a compound of Formula IIIa and a compound of Formula IIIb further comprises a seventeenth solvent component.

In some embodiments, the seventeenth solvent component comprises ethanol.

In some embodiments, prior to the reacting a composition comprising a compound of Formula IIIa and a compound of Formula IIIb, the (R)-ethyl 2-hydroxypropanimidate is dissolved in a eighteenth solvent component.

In some embodiments, the eighteenth solvent component comprises tetrahydrofuran.

In some embodiments, prior to the reacting the composition comprising a compound of Formula IIIa and a compound of Formula IIIb, the composition comprising a compound of Formula IIIa, a compound of Formula IIIb, and the seventeenth solvent component is heated at a temperature from about 75° C. to about 85° C.

In some embodiments, the (R)-ethyl 2-hydroxypropanimidate is prepared by reacting (R)-1-cyanoethyl acetate:

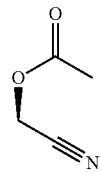

with ethanol in the presence of a strong acid.

In some embodiments, the strong acid used in the reaction of (R)-1-cyanoethyl acetate with ethanol is hydrogen chloride.

In some embodiments, about 2.9 to about 3.1 equivalents of ethanol is used based on 1 equivalent of (R)-ethyl 2-hydroxypropanimidate.

In some embodiments, the (R)-1-cyanoethyl acetate and ethanol are combined to form an ethanol mixture.

In some embodiments, the strong acid is added to the ethanol mixture to form a further mixture.

In some embodiments, the strong acid is added at a temperature from about −45° C. to about −35° C.

In some embodiments, adding the strong acid to the ethanol mixture to form a further mixture further comprises heating the further mixture to room temperature.

In some embodiments, the (R)-1-cyanoethyl acetate is formed by reacting (R)-1-amino-1-oxopropan-2-yl acetate:

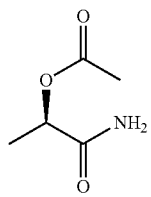

with cyanuric chloride.

In some embodiments, about 0.4 to about 0.5 equivalents of cyanuric chloride is used based on 1 equivalent of (R)-1-amino-1-oxopropan-2-yl acetate.

In some embodiments, prior to the reacting of (R)-1-amino-1-oxopropan-2-yl acetate, the (R)-1-amino-1-oxopropan-2-yl acetate is mixed with a nineteenth solvent component.

In some embodiments, the nineteenth solvent component comprises N,N-dimethylformamide.

In some embodiments, prior to the reacting of (R)-1-amino-1-oxopropan-2-yl acetate, the cyanuric chloride is dissolved in a twentieth solvent component.

In some embodiments, the twentieth solvent component comprises 2-methoxy-2-methylpropane.

In some embodiments, the reacting of (R)-1-amino-1-oxopropan-2-yl acetate is performed at about room temperature.

In some embodiments, the (R)-1-amino-1-oxopropan-2-yl acetate is prepared by protecting (R)-2-hydroxypropanamide:

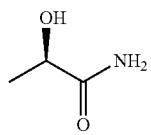

with acetyl chloride in the presence of an third tertiary amine base.

In some embodiments, the third tertiary amine base is 4-methylmorpholine.

In some embodiments, about 1 to about 1.1 equivalents of acetyl chloride is used based on 1 equivalent of (R)-2-hydroxypropanamide.

In some embodiments, the protecting is performed in the presence of a twenty-first solvent component.

In some embodiments, the twenty-first solvent component comprises tetrahydrofuran.

The present application further provides intermediates useful in the preparation of the compound of Formula Ia.

Accordingly, the present application provides a compound of Formula VIII:

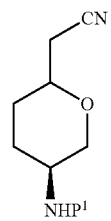

VIII wherein $P^1$ is an amine protecting group.

In some embodiments, $P^1$ is t-butoxycarbonyl.

The present application also provides a salt of Formula VIa:

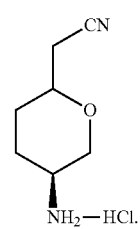

VIa

The present application further provides a compound of Formula Va:

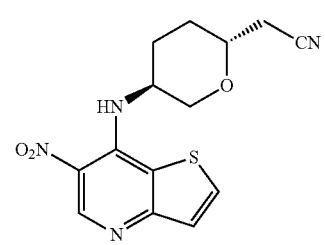

Va or salt thereof.

The present application further provides a compound of Formula Vb:

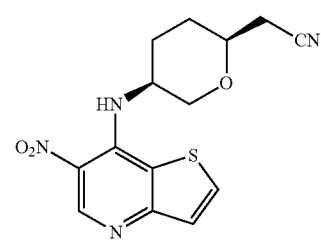

Vb or salt thereof.

The present application further provides a compound of Formula IIIa:

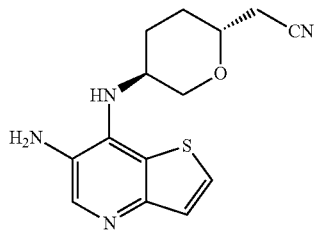

IIIa or salt thereof.

The present application further provides a compound of Formula IIIb:

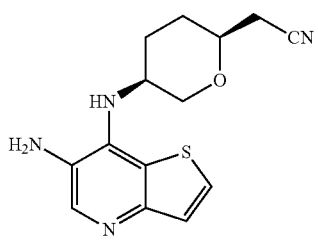

IIIb or salt thereof.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used here, the term "Wittig reagent" refers to a ylide formed by the reaction of a phosphonate compound of formula $P(=O)(C_{1-6}$ alkoxy$)_2(C_{1-6}$ alkyl-CN), wherein the alkoxy and alkyl groups each have 1 to 6 carbons, in the presence of a strong base (e.g., potassium tert-butoxide). In some embodiments, the term "Wittig reagent" refers a ylide formed by the reaction of a phosphonium salt (e.g., cyanomethyl (trimethyl)phosphonium chloride or tributyl(cyanomethyl)phosphonium chloride) in the presence of a strong base (e.g., potassium tert-butoxide).

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, 1 to 4 or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like.

As used herein, the term "$C_{1-6}$ alkoxy", employed alone or in combination with other terms, refers to a group of formula —O-alkyl, wherein the alkyl group has 1 to 6 carbons. Example alkoxy groups include methoxy, ethoxy, propoxy (e.g., n-propoxy and isopropoxy), butoxy (e.g., n-butoxy, tert-butoxy), and the like.

As used herein, the term "$C_{1-6}$ alkyloxonium reagent" refers to a reagent having a cation of group of formula ($C_{1-6}$ alkyl$)_3O^+$, wherein the $C_{1-6}$ alkyl group refers to a linear or branched alkyl group having 1 to 6 carbons. Example $C_{1-6}$ alkyloxonium reagents include trimethyloxonium tetrafluoroborate, triethyloxonium tetrafluoroborate (Meerwein's reagent), triethyloxonium hexafluorophosphate, triethyloxonium hexachloroantimonate, and the like. Counter ions include, but are not limited to tetrafluoroborate, hexafluorophosphate, and hexachloroantimonate.

As used herein, the term "amino" refers to a group of formula —NH$_2$.

As used herein, the term "amine base" refers to a mono-substituted amine group (i.e., primary amine base), di-substituted amine group (i.e., secondary amine base), or a tri-substituted amine group (i.e., tertiary amine base). Example mono-substituted amine bases include methyl amine, ethyl amine, propyl amine, butyl amine, and the like. Example di-substituted amine bases include dimethylamine, diethylamine, dipropylamine, dibutylamine, pyrrolidine, piperidine, azepane, morpholine, and the like. In some embodiments, the tertiary amine has the formula N(R')$_3$, wherein each R' is independently $C_{1-6}$ alkyl, 3-10 member cycloalkyl, 4-10 membered heterocycloalkyl, 1-10 membered heteroaryl, and 5-10 membered aryl, wherein said 3-10 member cycloalkyl, 4-10 membered heterocycloalkyl, 1-10 membered heteroaryl, and 5-10 membered aryl are optionally substituted by 1, 2, 3, 4, 5, or 6 $C_{1-6}$ alkyl groups. Example tertiary amine bases include trimethylamine, triethylamine, tripropylamine, triisopropylamine, tributylamine, tri-tert-butylamine, N,N-dimethylethanamine, N-ethyl-N-methylpropan-2-amine, N-ethyl-N-isopropylpropan-2-amine, N-methylmorpholine, and the like. In some embodiments, the term "tertiary amine base" refers to a group of formula N(R)$_3$, wherein each R is independently a linear or branched $C_{1-6}$ alkyl group.

As used herein, the term "cycloalkyl", employed alone or in combination with other terms, refers to a non-aromatic cyclic hydrocarbon moiety, which may optionally contain one or more alkenylene groups as part of the ring structure. In some embodiments, cycloalkyl is a 3-10 membered cycloalkyl, which is monocyclic or bicyclic. In some embodiments, cycloalkyl is a 3-6 or 3-7 monocyclic cycloalkyl. Examplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "aryl", employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is a 5-10 membered heteroaryl, which is monocyclic or bicyclic, comprising 1 to 9 carbon atoms and 1, 2, 3, or 4 heteroatom ring members independently selected from nitrogen, sulfur and oxygen. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like.

As used herein, the term "heterocycloalkyl", employed alone or in combination with other terms, refers to nonaromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or polycyclic (e.g., having 2, 3 or 4 fused, spirocyclic, or bridged rings) ring systems. In some embodiments, heterocycloalkyl is 5-10 membered heterocycloalkyl, which is monocyclic or bicyclic, comprising 2 to 9 carbon atoms and 1, 2, 3, or 4 heteroatom ring members independently selected from nitrogen, sulfur, and oxygen. Examples of heterocycloalkyl groups include 1,2,3,4-tetrahydro-quinoline, azetidine, azepane, pyrrolidine, piperidine, piperazine, morpholine, thiomorpholine, pyran, and a 2-oxo-1,3-oxazolidine ring.

As used herein, the term "alkali metal" includes lithium, sodium, and potassium.

As used herein, "halo" or "halogen", employed alone or in combination with other terms, includes fluoro, chloro, bromo, and iodo.

Example "N-halosuccinimide compound" include, but are not limited to, N-chlorosuccinimide, N-bromosuccinimide, and N-iodosuccinimide.

As used herein, the term "alkoxide base" refers to a base having a group of formula $(C_{1-6}$ alkyl$)O^-$, wherein the $C_{1-6}$ alkyl refers to a linear or branched alkyl group having 1 to 6 carbons. Example alkoxide bases include, but are not limited to, methoxide, ethoxide, propoxide, isopropoxide, n-butoxide, iso-butoxide, tert-butoxide, and the like.

As used herein, the term "alkali metal alkoxide" refers to a group of formula $M(O-C_{1-6}$ alkyl$)$, wherein M refers to an alkali metal (e.g., lithium, sodium, or potassium) and $C_{1-6}$ alkyl refers to a linear or branched alkyl group having 1 to 6 carbons. Example alkali metal alkoxides include, but are not limited to, sodium methoxide, sodium ethoxide, sodium isopropoxide, sodium tert-butoxide, lithium methoxide, lithium ethoxide, potassium methoxide, potassium ethoxide, potassium tert-butoxide, and the like.

As used herein the term, "hydrogenation catalyst" refers to a metal (e.g., palladium, nickel, or rhodium) catalyst suitable to catalyze a hydrogenation reaction (i.e., reaction of a compound with hydrogen gas). Example hydrogenation catalysts include, but are not limited to, palladium on carbon, Lindlar's catalyst (palladium deposited on calcium carbonate or barium sulfate), Wilkinson's catalyst, HRuCl (PPh$_3$)$_3$, RhCl(PPh$_3$)$_3$, [Rh(COD)Cl]$_2$, [Ir(COD) (PMePh$_2$)$_2$]$^+$, [Rh(1,5-cyclooctadiene)(PPh$_3$)$_2$]$^+$, PtO$_2$ (Adam's catalyst), palladium on carbon, palladium black, Lindlar's catalyst (palladium deposited on calcium carbonate or barium sulfate and treated with lead), and the like. In some embodiments, the hydrogenation catalyst is one found in Nishimura, Heterogeneous Catalytic Hydrogenation for Organic Synthesis, Edition 1, Wiley (Apr. 17, 2001) or Chaloner, Homogeneous Hydrogenation, Edition 1, Springer Netherlands (Dec. 6, 2010), each of which is incorporated herein by reference in its entirety.

Appropriate $P^1$ protecting groups include, but are not limited to the protecting groups for amines delineated in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. Example amine protecting groups include, but are not limited to, benzyloxycarbonyl (Cbz), 2,2,2-trichloroethoxycarbonyl (Troc), 2-(trimethylsilyl)ethoxycarbonyl (Teoc), 2-(4-trifluoromethylphenylsulfonyl)ethoxycarbonyl (Tsc), t-butoxycarbonyl (BOC), 1-adamantyloxycarbonyl (Adoc), 2-adamantylcarbonyl (2-Adoc), 2,4-dimethylpent-3-yloxycarbonyl (Doc), cyclohexyloxycarbonyl (Hoc), 1,1-dimethyl-2,2,2-trichloroethoxycarbonyl (TcBOC), vinyl, 2-chloroethyl, 2-phenylsulfonylethyl, allyl, benzyl, 2-nitrobenzyl, 4-nitrobenzyl, diphenyl-4-pyridylmethyl, N',N'-dimethylhydrazinyl, methoxymethyl, t-butoxymethyl (Bum), benzyloxymethyl (BOM), or 2-tetrahydropyranyl (THP), tri($C_{1-4}$ alkyl)silyl (e.g., tri(isopropyl)silyl), 1,1-diethoxymethyl, or N-pivaloyloxymethyl (POM).

Example oxidizing agents include Dess-Martin periodinane, 2,2,6,6-tetramethyl-1-piperidinyloxy free radical (TEMPO), N-halosuccinimide (e.g., N-bromosuccinimide, N-chlorosuccinimide, N-iodosuccinimide), and the like.

Example reducing agents include alkali metal borohydrides (e.g., lithium borohydride, sodium borohydride, potassium borohydride, etc.), alkali metal aluminum hydrides (e.g., lithium aluminum hydride, sodium aluminum hydride), hydrogen gas (e.g., H$_2$/Pd on carbon), and the like.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Some example strong bases include, but are not limited to, hydroxide, alkoxides, metal amides, metal hydrides, metal dialkylamides and arylamines, wherein; alkoxides include lithium, sodium and potassium salts of methyl, ethyl and t butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, i-propyl, n-butyl, t-butyl, trimethylsilyl and cyclohexyl substituted amides.

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected. In some embodiments, reactions can be carried out in the absence of solvent, such as when at least one of the reagents is a liquid or gas.

A "solvent component" may be one solvent or a mixture of two or more solvents.

As used herein, "second", "third," "fourth", etc. as a prefix to the phrase "solvent component" is used to differentiate the solvent component from other solvent components used in earlier or later steps of the process and does not indicate that multiple solvents must be present.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloro ethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether (diglyme), diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

The reactions of the processes described herein can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to affect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, i-propyl, n-butyl, t-butyl, trimethylsilyl and cyclohexyl substituted amides.

Upon carrying out preparation of compounds according to the processes described herein, the usual isolation and purification operations such as concentration, filtration, extraction, solid-phase extraction, recrystallization, chromatography, and the like may be used, to isolate the desired products.

The expression, "room temperature," as used herein, is understood in the art, and refer generally to a temperature (e.g. a reaction temperature) that is about the temperature of the room in which the reaction is carried out, for example, a temperature from about 20° C. to about 30° C.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures).

Preparation of the compounds described herein can involve the protection and deprotection of various chemical groups (e.g, protection and deprotection of amine groups). The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety. Adjustments to the protecting groups and formation and cleavage methods described herein may be adjusted as necessary in light of the various substituents.

As used herein, the term "deprotection conditions" refers to conditions suitable to cleave an amine protecting group. In some embodiments, deprotection conditions may include cleavage of a protecting group in the presence of a strong acid, in the presence of a strong base, in the presence of a reducing agent, or in the presence of an oxidizing agent. Deprotection of an amine protecting group can be accomplished by methods known in the art for the removal of particular protecting groups for amines, such as those in Wuts and Greene, Protective Groups in Organic Synthesis, 4th ed., John Wiley & Sons: New Jersey, pages 696-887 (and, in particular, pages 872-887) (2007), which is incorporated herein by reference in its entirety. In some embodiments, the treating comprises reacting the protected compound under acidic conditions (e.g., hydrochloric acid or trifluoroacetic acid). In some embodiments, the temperature is about room temperature, at a temperature from about 15° C. to about 40° C., or at a temperature from about 15° C. to about 30° C.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. In some embodiments, the compounds described herein include the N-oxide forms.

Methods

The compound of Formula Ia, 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile, is a selective inhibitor of JAK1. The compound of Formula Ia inhibits JAK1 preferentially over JAK2 (e.g., have a JAK1/JAK2 IC$_{50}$ ratio >10).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106: 9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

JAK inhibitors are useful in treating various JAK-associated diseases or disorders. Examples of JAK-associated diseases include diseases involving the immune system including, for example, organ transplant rejection (e.g., allograft rejection and graft versus host disease). Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated diseases include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chrondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

Further examples of JAK-associated diseases or conditions include those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides. Other examples of JAK-associated diseases or conditions include pulmonary arterial hypertension.

Other examples of JAK-associated diseases or conditions include inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/Post-ET MF)). In some embodiments, the myeloproliferative disorder is post-essential thrombocythemia myelofibrosis (Post-ET MF). In some embodiments, the myeloproliferative disorder is post polycythemia vera myelofibrosis (Post-PV MF).

JAK-associated diseases further include myelodysplastic syndrome (MDS).

As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br J Haematol* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114:937-951; Swerdlow, et al., *WHO Classification of Tumours of Haematopoietic and Lymphoid Tissues.* 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues.* (ed. 4th edition): Lyon, France: IARC Press; 2008: 88-103).

TABLE 1

2008 WHO Classification for De Novo Myelodysplastic Syndrome

| Subtype | Blood | Bone Marrow |
|---|---|---|
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × 10$^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × 10$^9$/L monocytes | Unilineage or multilineage dysplasia, No Auer rods, 5% to 9% blasts |
| Refractory anemia with excess blasts-2 (RAEB-2) | Cytopenia(s), ≥5% to 19% blasts, <1 × 10$^9$/L monocytes | Unilineage or multilineage dysplasia, ±Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del(5q) | Anemia, platelets normal or increased | Unilineage erythroid. Isolated del(5q), <5% blasts |

In some embodiments, the present application provides a method of treating a myelodysplastic syndrome (MDS) in patient in need thereof, comprising administering to said patient a compound of Formula Ia, or a pharmaceutically acceptable salt thereof, wherein said MDS is selected from refractory cytopenia with unilineage dysplasia (RCUD), refractory anemia with ring sideroblasts (RARS), refractory cytopenia with multilineage dysplasia, refractory anemia with excess blasts-1 (RAEB-1), refractory anemia with excess blasts-2 (RAEB-2), myelodysplastic syndrome, unclassified (MDS-U), and MDS associated with isolated del(5q).

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

Other examples of JAK-associated diseases or conditions include ameliorating the dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

Further JAK-associated diseases include ischemia reperfusion injuries or a disease or condition related to an inflammatory ischemic event such as stroke or cardiac arrest, endotoxin-driven disease state (e.g., complications after bypass surgery or chronic endotoxin states contributing to chronic cardiac failure), anorexia, cachexia, fatigue such as that resulting from or associated with cancer, restenosis, sclerodermitis, fibrosis, conditions associated with hypoxia or astrogliosis such as, for example, diabetic retinopathy, cancer, or neurodegeneration, and other inflammatory diseases such as systemic inflammatory response syndrome (SIRS) and septic shock.

Other JAK-associated diseases include gout and increased prostate size due to, e.g., benign prostatic hypertrophy or benign prostatic hyperplasia, as well as bone resorption diseases such as osteoporosis or osteoarthritis, bone resorption diseases associated with: hormonal imbalance and/or hormonal therapy, autoimmune disease (e.g. osseous sarcoidosis), or cancer (e.g. myeloma).

Further JAK-associated diseases include a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface*, 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

Further JAK-associated diseases include conjunctivitis, uveitis (including chronic uveitis), chorioditis, retinitis, cyclitis, scleritis, episcleritis, or iritis. Other JAK-associated diseases include respiratory dysfunction or failure associated wth viral infection, such as influenza and SARS.

Combination Therapies

One or more additional pharmaceutical agents such as, for example, chemotherapeutics, anti-inflammatory agents, steroids, immunosuppressants, as well as PI3Kδ, mTor, Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, the additional pharmaceutical agent is selected from IMiDs, an anti-IL-6 agent, an anti-TNF-α agent, a hypomethylating agent, and a biologic response modifier (BRM).

Generally, a BRM is a substance made from living organisms to treat disease, which may occur naturally in the body or may be made in the laboratory. Examples of BRMs include IL-2, interferon, various types of colony-stimulating factors (CSF, GM-CSF, G-CSF), monoclonal antibodies such as abciximab, etanercept, infliximab, rituximab, trasturzumab, and high dose ascorbate.

In some embodiments, the anti-TNF-α agent is infliximab, and etanercept.

In some embodiments, the hypomethylating agent is a DNA methyltransferase inhibitor. In some embodiments, the DNA methyltransferase inhibitor is selected from 5 azacytidine and decitabine.

Generally, IMiDs are as immunomodulatory agents. In some embodiments, the IMiD is selected from thalidomide, lenalidomide, pomalidomide, CC-11006, and CC-10015.

In some embodiments, the additional pharmaceutical agent is selected from anti-thymocyte globulin, recombinant human granulocyte colony-stimulating factor (G CSF), granulocyte-monocyte CSF (GM-CSF), a erythropoiesis-stimulating agent (ESA), and cyclosporine.

In some embodiments, the additional pharmaceutical agent is an additional JAK inhibitor. In some embodiments, the additional JAK inhibitor is tofacitinib or ruxolitinib.

In some embodiments, one or more of the compounds of the invention can be used in combination with one or more other kinase inhibitors including imatinib, particularly for treating patients resistant to imatinib or other kinase inhibitors.

In some embodiments, a suitable chemotherapeutical agent can be selected from antimetabolite agents, topoisomerase 1 inhibitors, platinum analogs, taxanes, anthracyclines, and EGFR inhibitors, and combinations thereof.

In some embodiments, antimetabolite agents include capecitabine, gemcitabine, and fluorouracil (5-FU).

In some embodiments, taxanes include paclitaxel, Abraxane® (paclitaxel protein-bound particles for injectable suspension), and Taxotere® (docetaxel).

In some embodiments, platinum analogs include oxaliplatin, cisplatin, and carboplatin.

In some embodiments, topoisomerase 1 inhibitors include irinotecan and topotecan.

In some embodiments, anthracyclines include doxorubicin or liposomal formulations of doxorubicin.

In some embodiments, the chemotherapeutic is FOLFIRINOX (5-FU, lecovorin, irinotecan and oxaliplatin). In some embodiments, the chemotherapeutic agent is gemcitabine and Abraxane® (paclitaxel protein-bound particles for injectable suspension).

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline). In some embodiments, the additional therapeutic agent binds to FKBP 12.

In some embodiments, the additional therapeutic agent is an alkylating agent or DNA cross-linking agent; an antimetabolite/demethylating agent (e.g., 5-flurouracil, capecitabine or azacitidine); an anti-hormone therapy (e.g., hormone receptor antagonists, SERMs, or aromotase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier. In some embodiments, the composition comprises at least one compound described herein, or a pharmaceutically acceptable salt thereof, and at least one component selected from microcrystalline cellulose, lactose monohydrate, hydroxypropyl methylcellulose, and polyethylene oxide. In some embodiments, the composition comprises at least one compound described herein, or a pharmaceutically acceptable salt thereof, and microcrystalline cellulose, lactose monohydrate, and hydroxypropyl methylcellulose. In some embodiments, the composition comprises at least one compound described herein, or a pharmaceutically acceptable salt thereof, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel KOOLV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is a topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxpropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic compositon comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro JAK labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Synthesis

The compound of Formula Ia can be synthesized according to the embodiments above and as further illustrated by Schemes I-III below. In Scheme I, the nucleophilic coupling of (i) and (ii) in the presence of an amine base (e.g., N,N-diisopropylethylamine) affords the isomeric mixture of compounds (iii-a) and (iii-b). Subsequent reduction of the nitro group under hydrogenation conditions (e.g., in the presence of hydrogen gas and a hydrogen catalyst (e.g. palladium on carbon)) affords the isomeric mixture of compounds (iv-a) and (iv-b). Coupling of (iv-a) and (iv-b) with (R)-(+)-lactamide in the presence of an alkyloxonium reagent (e.g., triethyloxonium tetrafluoroborate) and subsequent cyclization affords the a mixture of the fused-tricyclic compounds of Formula Ia and Formula Ib. Subsequent reaction under reverse racemization conditions (e.g. in the presence of a strong base (e.g. potassium tert-butoxide)) yields a single isomer of the compound of Formula Ia, 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile, which may be optionally hydrated to form the monohydrate compound of Formula II.

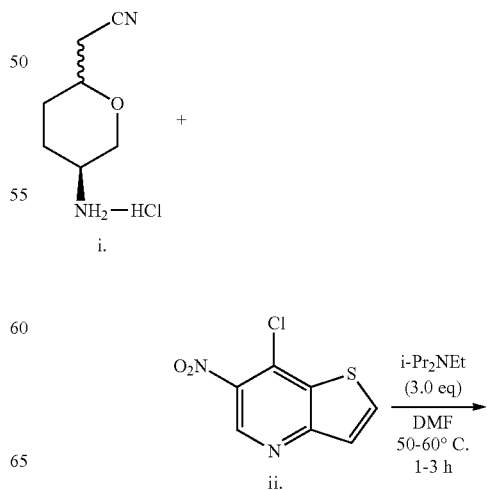

Scheme I

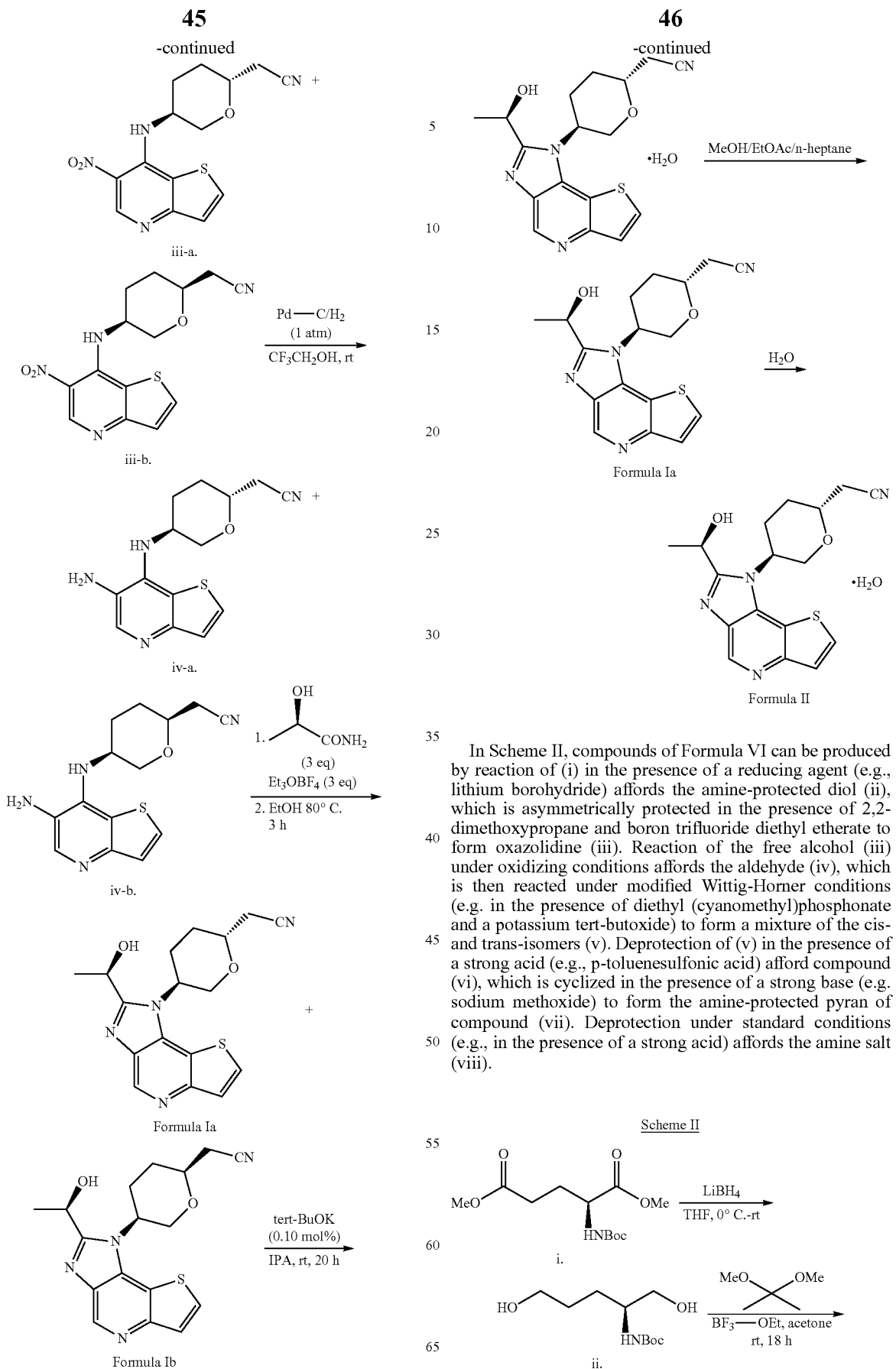

In Scheme II, compounds of Formula VI can be produced by reaction of (i) in the presence of a reducing agent (e.g., lithium borohydride) affords the amine-protected diol (ii), which is asymmetrically protected in the presence of 2,2-dimethoxypropane and boron trifluoride diethyl etherate to form oxazolidine (iii). Reaction of the free alcohol (iii) under oxidizing conditions affords the aldehyde (iv), which is then reacted under modified Wittig-Horner conditions (e.g. in the presence of diethyl (cyanomethyl)phosphonate and a potassium tert-butoxide) to form a mixture of the cis- and trans-isomers (v). Deprotection of (v) in the presence of a strong acid (e.g., p-toluenesulfonic acid) afford compound (vi), which is cyclized in the presence of a strong base (e.g. sodium methoxide) to form the amine-protected pyran of compound (vii). Deprotection under standard conditions (e.g., in the presence of a strong acid) affords the amine salt (viii).

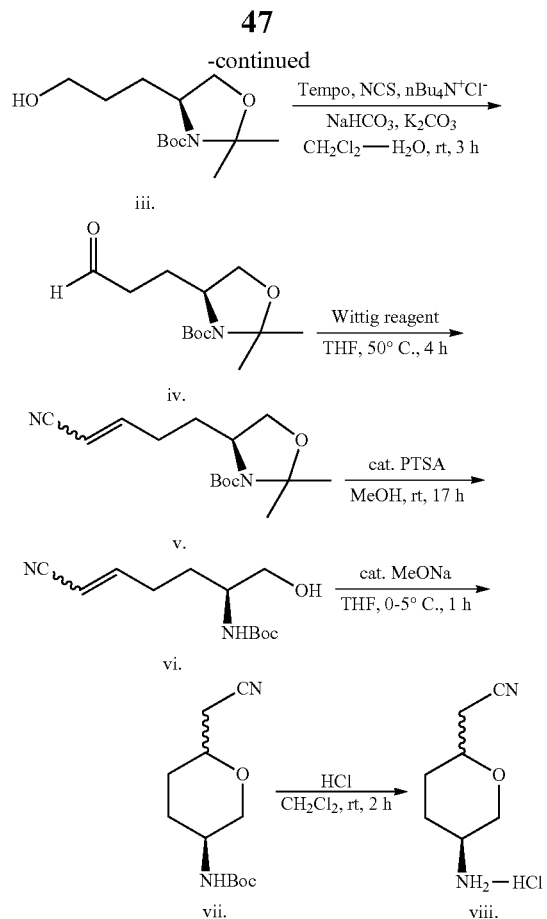

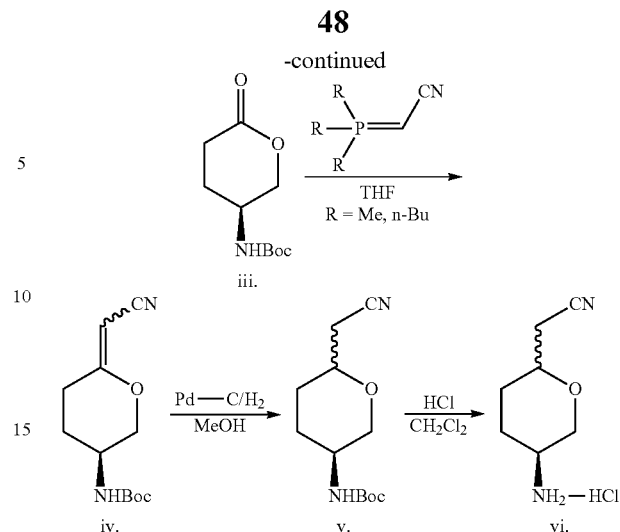

In Scheme III, compounds of Formula VI can be produced. Accordingly, asymmetric carbonyl reduction of carboxylic acid (i) affords the hydroxy-ester compound (ii), which is subsequently cyclized in the presence of a weak organic acid (e.g. acetic acid) to form amino-lactone (iii). Reaction of (iii) under modified Wittig conditions (e.g., in the presence of cyanomethyl (trimethyl)phosphonium chloride and potassium tert-butoxide, or alternatively in the presence of tributyl(cyanomethyl)phosphonium chloride and potassium tert-butoxide) afford the mixture of cis- and trans-isomers of (iv). Reduction of the alkene (iv) in the presence of a hydrogen gas and a hydrogenation catalyst (e.g., palladium on carbon) affords the mixture of R- and S-isomers of (v). Deprotection of the amine under standard conditions (e.g., in the presence of a strong acid) affords amine salt (vi).

Intermediate (R)-4-methoxy-2,2,5-trimethyl-2,5-dihydrooxazole can be prepared, for example, according to the process shown in Scheme IV. For example, reaction of (R)-2-hydroxypropanamide (i) with 2,2-dimethoxypropane (ii) in the presence of a boron-trihalogen etherate (e.g., BF₃OEt₂) affords (R)-2,2,5-trimethyloxazolidin-4-one (iii). Reaction of compound (iii) with a methylating agent (e.g., Me₃O⁺BF₄⁻) and subsequent reaction in the presence of a base (e.g., sodium carbonate) affords (R)-4-methoxy-2,2,5-trimethyl-2,5-dihydrooxazole (v).

Scheme IV

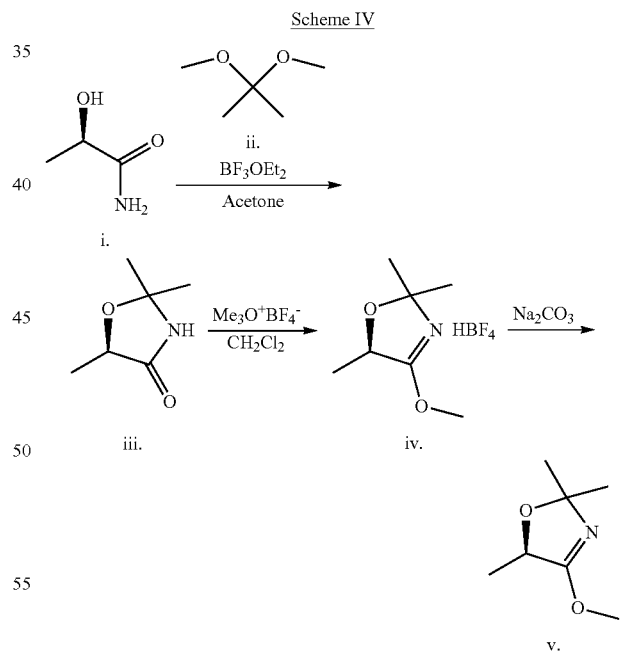

Scheme III

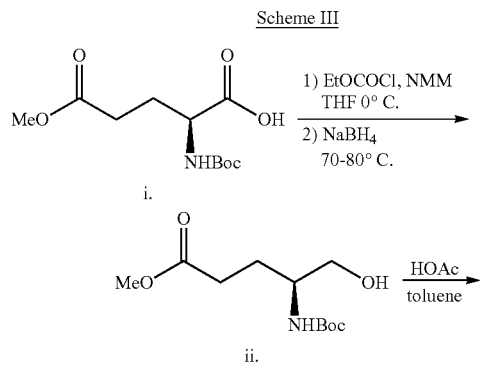

A mixture of the compounds of Formulae Ia and Ib can also be prepared, for example, according to the process shown in Scheme V. (R)-2,2,5-trimethyloxazolidin-4-one (i) is first reacted with a methylating agent (e.g., Me₃O⁺BF₄⁻) to form (R)-4-methoxy-2,2,5-trimethyl-2,5-dihydrooxazole (ii), which is subsequently reacted with a mixture of 2-((2R, 5S)-5-(6-aminothieno[3,2-b]pyridin-7-ylamino)tetrahydro-2H-pyran-2-yl)acetonitrile and 2-((2S,5S)-5-(6-aminothieno

[3,2-b]pyridin-7-ylamino)tetrahydro-2H-pyran-2-yl) acetonitrile (iii) to afford a mixture of the compounds of Formulae Ia and Ib (iv).

Scheme V

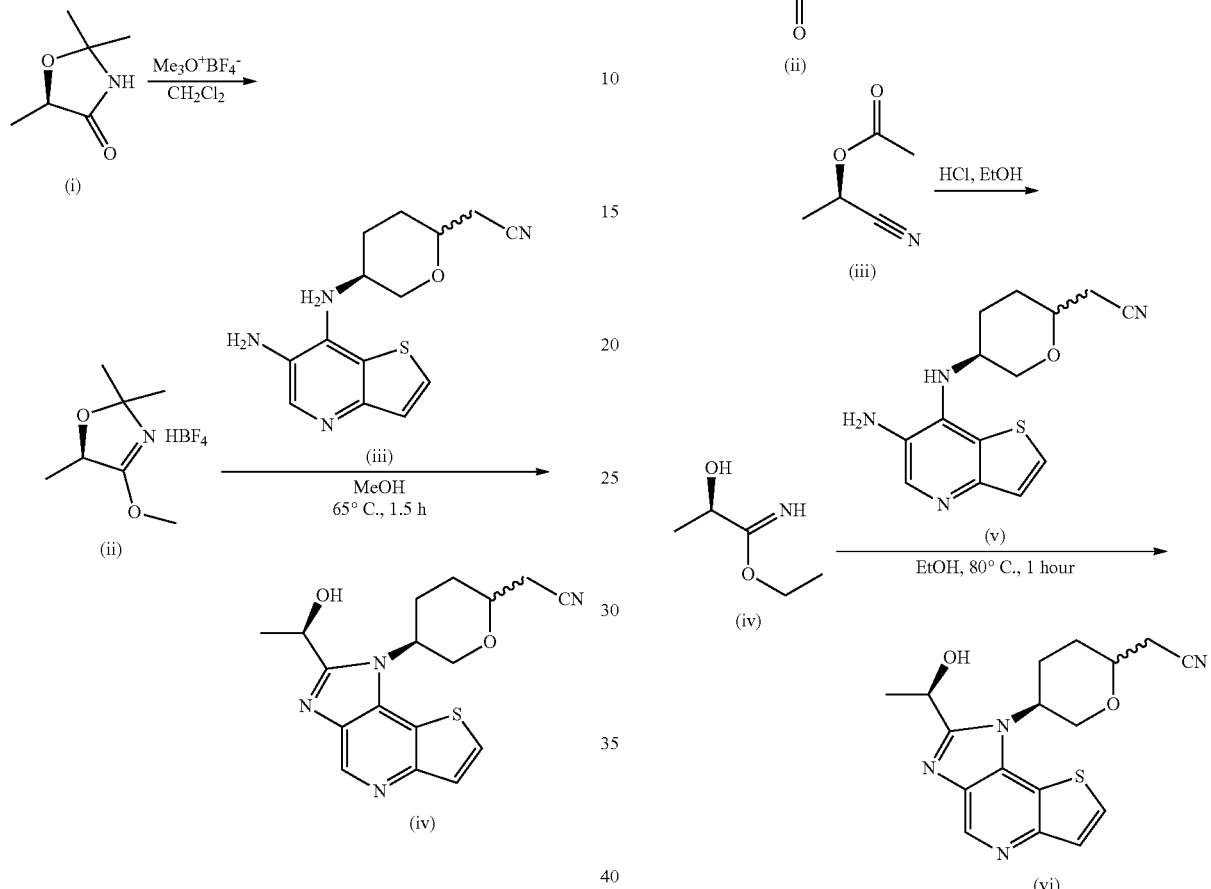

A mixture of the compounds of Formulae Ia and Ib can also be prepared, for example, according to the process shown in Scheme VI. (R)-2-hydroxypropanamide (i) is first protected under standard alcohol protection conditions (e.g., reaction with acetyl chloride) to form (R)-1-amino-1-oxo-propan-2-yl acetate (ii), which is then reacted with cyanuric chloride to form (R)-1-cyanoethyl acetate (iii). Subsequent reaction of (iii) with ethanol in the presence of an acid catalyst (e.g., hydrogen chloride) affords (R)-ethyl 2-hydroxypropanimidate (iv) which is then reacted with a mixture of 2-((2R,5S)-5-(6-aminothieno[3,2-b]pyridin-7-ylamino)tetrahydro-2H-pyran-2-yl)acetonitrile and 2-((2S,5S)-5-(6-aminothieno[3,2-b]pyridin-7-ylamino)tetrahydro-2H-pyran-2-yl)acetonitrile (v) to form a mixture of the compounds of Formulae Ia and Ib (vi).

Scheme VI

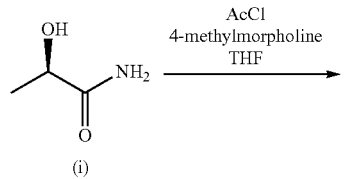

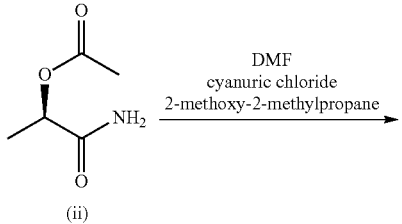

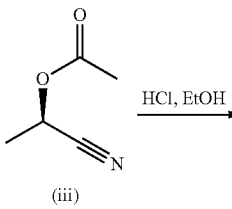

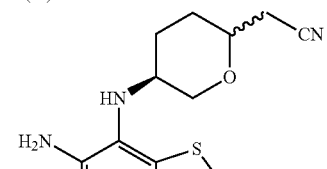

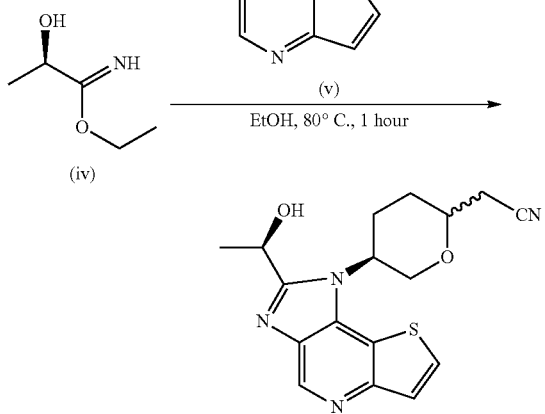

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Open access prep. LC-MS purification of some of the compounds prepared was performed on Waters mass directed fractionation systems. The basic equipment setup, protocols, and control software for the operation of these systems have been described in detail in literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Hague, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity under the following conditions:

Instrument; Agilent 1100 series, LC/MSD, Column: Waters Sunfire™ C$_{18}$ 5 μm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were analyzed using Differential Scanning calorimetry (DSC). Typical DSC conditions are as follows:

TA Instruments Differential Scanning calorimetry, Model Q200 with autosampler. Temperature range: 30-350° C.; Temperature ramp rate: 10° C./min; Tzero aluminum sample pan and lid; nitrogen gas flow at 50 mL/min.

Some of the compounds prepared were analyzed using Thermogravimetric Analysis (TGA). Typical TGA conditions are as follows:

TA Instrument Thermogravimetric Analyzer, Model Q500. Temperature range: 20° C. to 600° C.; Temperature ramp rate: 20° C./min; nitrogen purge flow: 40 mL/min; Balance purge flow: 60 mL/min; Sample purge flow; platinum sample pan.

PerkinElmer Thermogravimetric Analyzer, Model Pyris 1. Temperature range: 25° C. to 300° C.; Temperature ramp rate: 10° C./min; Nitrogen purge gas flow: 60 mL/min; TGA ceramic crucible sample holder.

Some of the compounds prepared were analyzed using X-Ray Powder Diffraction (XRPD). Typical XRPD conditions are as follows:

Bruker D2 PHASER X-Ray Powder Diffractometer instrument; X-ray radiation wavelength: 1.05406 Å CuKAI; X-ray power: 30 KV, 10 mA; Sample powder: dispersed on a zero-background sample holder; General measurement conditions: Start Angle—5 degree; Stop Angle—60 degree; Sampling—0.015 degree; Scan speed—2 degree/min.

Rigaku MiniFlex X-ray Powder Diffractometer; X-ray radiation is from Copper Cu at 1.054056 Å with K$_\beta$ filter; X-ray power: 30 KV, 15 mA; Sample powder: dispersed on a zero-background sample holder. General measurement condition: Start Angle—3 degree; Stop Angle—45 degree; Sampling—0.02 degree; Scan speed—2 degree/min.

Some of the compounds prepared were analyzed using Dynamic Vapor Sorption (DVS). Typical DVS conditions are as follows: SGA-100 Symmetric Vapor Sorption Analyzer from VTI Corporation. The moisture uptake profile was completed in four cycles in 10% relative humidity (RH) increments with the first adsorption from 25% to 95% RH, followed by desorption in 10% increments from 95% to 5% RH. The equilibration criteria were 0.0050 wt % in 5 minutes with a maximum equilibration time of 180 minutes; Data logging interval: 2.00 min or 0.0100 wt %. All adsorption and desorption were performed at room temperature (25° C.). No pre-drying step was applied.

Some of the compounds prepared were analyzed after treatment in a humidity chamber. Typical humidity chamber conditions are as follows:

Temperature: 40° C.; Relative humidity: 75%; Time: 5 days.

Temperature: 30° C.; Relative humidity: 90%; Time: 7 days.

Example 1. 2-((2R,5S)-5-Aminotetrahydro-2H-pyran-2-yl)acetonitrile hydrochloride and 2-((2S,5S)-5-aminotetrahydro-2H-pyran-2-yl)acetonitrile hydrochloride (Procedure 1)

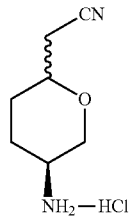

Step 1. (S)-tert-Butyl 1,5-dihydroxypentan-2-ylcarbamate

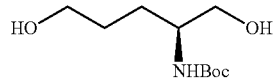 [SMILES: CC(C)(C)OC(=O)N[C@H](CO)CCCO]

In a 5-necked, 5-L round bottom flask equipped with an overhead mechanical stirrer, a thermocouple, a reflux condenser, an addition funnel, and a nitrogen inlet was placed lithium borohydride (29.9 g, 1.37 mol, 2.0 eq.) at room temperature. Tetrahydrofuran (THF, 1.12 L) was charged to the flask while maintaining the internal temperature at below 40° C. The resulting solution was then cooled to 0-5° C. before a solution of (S)-dimethyl 2-(tert-butoxycarbonylamino)pentanedioate (189 g, 0.687 mol) in THF (0.60 L) was added over a period greater than 50 minutes via the addition funnel. The resulting reaction mixture was gradually warmed to room temperature and stirred at room temperature for 17 h and then cooled to 15° C. Methanol (MeOH, 415 mL) was then added dropwise to the reaction mixture over 3 h to quench residual lithium borohydride. During addition of methanol, vigorous gas evolution was observed. The quenched reaction mixture was then concentrated under reduced pressure to remove most of the solvents and the residue was treated with ethyl acetate (EtOAc, 350 mL) and water (300 mL). The resulting suspension was stirred at room temperature for 15 minutes before being filtered through a sintered funnel. The two phases of the filtrate were separated and the aqueous phase was extracted with EtOAc (100 mL). The combined organic phases were washed with brine (150 mL), dried over anhydrous sodium sulfate, and concentrated under reduced pressure to afford crude (S)-tert-butyl 1,5-dihydroxypentan-2-ylcarbamate (135 g, 89.7%) as a white solid, which was used in the subsequent reaction without further purification. $^1$H NMR (400 MHz, DMSO-d$_6$) δ 6.42 (d, J=8.5 Hz, 1H), 4.52 (t, J=5.5 Hz, 1H), 4.33 (t, J=5.1 Hz, 1H), 3.42-3.21 (m, 4H), 3.18 (dt, J=10.5, 6.1 Hz, 1H), 1.54-1.44 (m, 1H), 1.41-1.28 (m, 11H), 1.22-1.16 (m, 1H) ppm.

Step 2. (S)-tert-Butyl 4-(3-hydroxypropyl)-2,2-dimethyloxazolidine-3-carboxylate

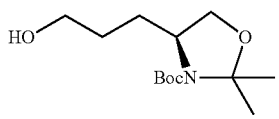 [SMILES: CC(C)(C)OC(=O)N1[C@@H](CCCO)COC1(C)C]

In a 5-necked, 5-L round bottom flask equipped with an overhead mechanical stirrer, a thermocouple, an addition funnel, and a nitrogen inlet was placed (S)-tert-butyl 1,5-dihydroxypentan-2-ylcarbamate (105 g, 0.479 mol) and acetone (4.0 L) at room temperature. The solution was then treated with 2,2-dimethoxypropane (64.8 g, 0.622 mol, 1.3 eq.) and boron trifluoride diethyl etherate ($BF_3$-$Et_2O$, 6.1 mL, 0.048 mol, 0.10 eq.) sequentially at room temperature. The resulting reaction mixture was stirred at room temperature for 18 h before triethylamine (TEA, 40.0 mL, 0.287 mol, 0.60 eq.) was added. The resulting mixture was then concentrated under reduced pressure to remove most of the solvents and the residue was treated with EtOAc (1000 mL) and water (200 mL). The two phases were separated and the organic phase was washed with brine (200 mL), dried over sodium sulfate, and concentrated under reduced pressure. The residue was purified by column chromatography ($SiO_2$, gradient elution with 0 to 50% of ethyl acetate in hexanes) to afford (S)-tert-butyl 4-(3-hydroxypropyl)-2,2-dimethyloxazolidine-3-carboxylate (95.0 g, 76.5%) as a colorless oil. $^1$H NMR (400 MHz, DMSO-$d_6$) δ 4.39 (t, J=5.1 Hz, 1H), 3.85 (dd, J=8.7, 5.7 Hz, 1H), 3.72 (s, 1H), 3.66 (dd, J=8.8, 1.3 Hz, 1H), 3.42-3.32 (m, 2H), 1.61-1.54 (m, 1H), 1.51-1.24 (m, 18H) ppm.

Step 3. (S)-tert-Butyl 2,2-dimethyl-4-(3-oxopropyl)oxazolidine-3-carboxylate

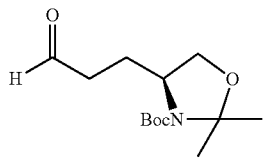 [SMILES: CC(C)(C)OC(=O)N1[C@@H](CCC=O)COC1(C)C]

In a 5-necked 5-L round bottom flask equipped with an overhead mechanical stirrer, a thermocouple, an addition funnel, and a nitrogen inlet was placed (S)-tert-butyl 4-(3-hydroxypropyl)-2,2-dimethyloxazolidine-3-carboxylate (110.0 g, 0.424 mol) and dichloromethane (DCM, 1200 mL) at room temperature. The resulting solution was then treated with 2,2,6,6-tetramethyl-1-piperidinyloxy free radical (TEMPO, 6.6 g, 0.042 mol, 0.10 eq.) and tetra-n-butylammonium chloride (11.8 g, 0.042 mol, 0.10 eq.) at room temperature before an aqueous solution of sodium bicarbonate (174 g, 2.08 mol, 5.0 eq) and an aqueous solution of potassium carbonate (28.7 g, 0.208 mol, 0.50 eq) were sequentially added to the reaction mixture at room temperature. While the resulting mixture was stirred vigorously, N-chlorosuccinimide (69.1 g, 0.518 mol, 1.22 eq.) was added at room temperature. The resulting reaction mixture was then stirred at room temperature for an additional 3 h before being transferred to a separation funnel. The two phases were separated and the aqueous phase was extracted with DCM (250 mL). The combined organic layers were washed with brine (2×300 mL), dried over anhydrous sodium sulfate, concentrated under reduced pressure, and dried under vacuum to afford crude (S)-tert-butyl 2,2-dimethyl-4-(3-oxopropyl)oxazolidine-3-carboxylate (109.1 g, 100%) as a pale orange oil, which was used in the subsequent reaction without further purification. $^1$H NMR (300 MHz, DMSO-$d_6$) δ 9.64 (s, 1H), 4.01-3.60 (m, 3H), 2.39 (dd, J=10.9, 4.0 Hz, 2H), 1.84-1.64 (m, 2H), 1.47-1.38 (m, 15H) ppm.

Step 4. (S)-tert-Butyl 4-(4-cyanobut-3-enyl)-2,2-dimethyloxazolidine-3-carboxylate

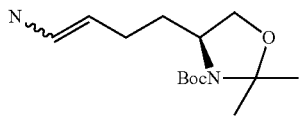 [SMILES: CC(C)(C)OC(=O)N1[C@@H](CCC=CN)COC1(C)C]

In a 3-necked, 3-L round bottom flask equipped with an overhead mechanical stirrer, a thermocouple, and an addition funnel under nitrogen atmosphere was placed potassium tert-butoxide (1 M solution in THF, 1000 mL, 1.00 mol, 1.11 eq.) and tetrahydrofuran (THF, 700 mL) at room temperature. The solution was cooled to 0-5° C. and diethyl cyanomethylphosphonate (177.2 g, 1.00 mol, 1.11 eq.) was added dropwise via the addition funnel while maintaining the internal temperature at below 10° C. The resulting reaction mixture was then stirred at room temperature for 2 h, and labeled as Solution A for the subsequent reaction. In a separate 5-necked, 12-L round bottom flask equipped with an overhead mechanical stirrer, a thermocouple, an addition funnel, and a nitrogen inlet was placed (S)-tert-butyl 2,2-dimethyl-4-(3-oxopropyl)oxazolidine-3-carboxylate (232.0 g, 0.901 mol) and THF (3500 mL) at room temperature. The resulting solution was cooled to 0-5° C., and was labeled as Solution B. Solution A was then added to Solution B dropwise while maintaining the internal temperature at below 5° C. The resulting reaction mixture was gradually warmed to room temperature and stirred at room temperature for 1 h. Water (500 mL) was charged to the reaction mixture and two phases were separated. The aqueous phase was then extracted with EtOAc (2×100 mL). The combined organic phases were washed with brine (2×100 mL), dried over anhydrous magnesium sulfate, and concentrated under reduced pressure. The residue was purified by column chromatography ($SiO_2$, gradient elution with 0 to 30% of ethyl acetate in hexanes) to provide (S)-tert-butyl 4-(4-cyanobut-3-enyl)-2,2-dimethyloxazolidine-3-carboxylate (179.0 g, 70.8%) as a colorless oil. $^1$H NMR (300 MHz, DMSO-$d_6$) δ 6.84 (dt, J=16.4, 6.8 Hz, 0.5H), 6.66 (dt, J=10.9, 7.7 Hz, 0.5H), 5.83-5.51 (m, 1H), 3.92-3.49 (m, 3H), 2.35-2.05 (m, 2H), 1.73-1.52 (m, 2H), 1.45-1.38 (m, 15H).

Step 5. (S)-tert-Butyl 6-cyano-1-hydroxyhex-5-en-2-ylcarbamate

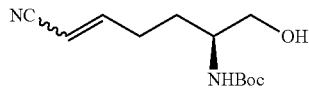 [SMILES: CC(C)(C)OC(=O)N[C@H](CO)CCC=CC#N]

In a 5-necked, 5-L round bottom flask equipped with an overhead mechanical stirrer, a thermocouple, an addition funnel, and a nitrogen inlet was placed (S)-tert-butyl 4-(4-cyanobut-3-enyl)-2,2-dimethyloxazolidine-3-carboxylate (179.0 g, 0.638 mol) and methanol (2000 mL) at room temperature. The resulting colorless solution was cooled to 0-5° C. before being treated with catalytic amount of p-toluenesulfonic acid (PTSA, 12.1 g, 0.064 mol, 0.10 eq.). The resulting reaction mixture was gradually warmed to room temperature and stirred at room temperature for an additional 17 h. An aqueous solution of sodium bicarbonate (100 mL) was then added to the reaction mixture at room temperature and the resulting mixture was concentrated under reduced pressure to about 500 mL. The residue was then extracted with ethyl acetate (2×500 mL). The combined organic phases were washed with brine (2×100 mL), dried over anhydrous magnesium sulfate, concentrated under reduced pressure, and dried under vacuum to afford crude (S)-tert-butyl 6-cyano-1-hydroxyhex-5-en-2-ylcarbamate (144.2 g, 94%) as a light pink oil, which was used in the subsequent reaction without further purification. $^1$H NMR (300 MHz, CDCl$_3$) δ 6.72 (dt, J=16.3, 6.9 Hz, 0.5H), 6.53 (dt, J=10.9, 7.6 Hz, 0.5H), 5.51-5.08 (m, 1H), 4.73 (s, 1H), 3.83-3.34 (m, 3H), 2.49 (dt, J=11.3, 5.9 Hz, 1H), 2.31 (q, J=7.0 Hz, 1H), 1.74-1.57 (m, 3H), 1.44 (s, 9H).

Step 6. (S)-tert-Butyl 6-(cyanomethyl)tetrahydro-2H-pyran-3-ylcarbamate (Mixture of Cis- and Trans-Isomers)

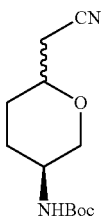 [SMILES: CC(C)(C)OC(=O)N[C@H]1CCC(CC#N)OC1]

In a 5-necked, 5-L round bottom flask equipped with an overhead mechanical stirrer, a thermocouple, an addition funnel, and a nitrogen inlet was placed (S)-tert-butyl 6-cyano-1-hydroxyhex-5-en-2-ylcarbamate (173.0 g, 0.720 mol) and tetrahydrofuran (1700 mL) at room temperature. The solution was cooled to 0-5° C. before a solution of sodium methoxide (0.5 M solution in methanol, 21.30 mL, 0.011 mol, 0.015 eq) in THF (90 mL) was added dropwise via the addition funnel while maintaining the internal temperature at below 5° C. The resulting reaction mixture was stirred at below 5° C. for an additional 1 h before brine (500 mL) and tert-butyl methyl ether (TBME, 400 mL) were added to the reaction mixture sequentially. The two phases were separated and the aqueous phase was extracted with TBME (250 mL). The combined organic phases were washed with brine (250 mL), dried over anhydrous magnesium sulfate, concentrated under reduced pressure, and dried under vacuum to afford crude (S)-tert-butyl 6-(cyanomethyl)tetrahydro-2H-pyran-3-ylcarbamate (173.0 g, 100%) as a viscous solid. The crude product, obtained as a mixture of cis- and trans-isomers, was used in the subsequent reaction without further purification. $^1$H NMR (400 MHz, CDCl$_3$) δ 5.13 (s, 0.5H), 4.25 (s, 0.5H), 4.10 (ddd, J=10.9, 4.7, 2.2 Hz, 0.5H), 3.89 (d, J=12.1 Hz, 0.5H), 3.72 (s, 0.5H), 3.66-3.57 (m, 1.5H), 3.56-3.49 (m, 0.5H), 3.03 (t, J=10.8 Hz, 0.5H), 2.54 (dd, J=6.0, 2.5 Hz, 2H), 2.19-2.08 (m, 0.5H), 2.00 (d, J=13.2 Hz, 0.5H), 1.87 (d, J=13.1 Hz, 0.5H), 1.65-1.62 (m, 2H), 1.44 (d, J=6.5 Hz, 9H), 1.38-1.24 (m, 0.5H).

Step 7. 2-((2R,5S)-5-Aminotetrahydro-2H-pyran-2-yl)acetonitrile hydrochloride and 2-((2S,5S)-5-aminotetrahydro-2H-pyran-2-yl)acetonitrile hydrochloride (Mixture of Trans- and Cis-Isomers)

In a 5-necked, 5-L round bottom flask equipped with an overhead mechanical stirrer, a thermocouple, an addition funnel, and a nitrogen inlet was placed (S)-tert-butyl 6-(cya-nomethyl)tetrahydro-2H-pyran-3-ylcarbamate (a mixture of cis- and trans-isomers, 173.0 g, 0.720 mol) and dichloromethane (1730 mL) at room temperature. The resulting solution was then treated with a solution of 4.0 M hydrogen chloride (HCl) in 1,4-dioxane (720 mL, 2.880 mol, 4.0 eq.) via the addition funnel. The resulting reaction mixture was stirred at room temperature for 2 h before tert-butyl methyl ether (TBME, 1000 mL) was added. The resulting suspension was stirred at room temperature for 30 minutes. The white solids formed were collected by filtration, washed with TBME (280 mL), and dried in a vacuum oven with nitrogen sweeping at 50° C. to afford 2-((2R,5S)-5-aminotetrahydro-2H-pyran-2-yl)acetonitrile hydrochloride and 2-((2S,5S)-5-aminotetrahydro-2H-pyran-2-yl)acetonitrile hydrochloride (114.0 g, 89.6%) as a mixture of trans- and cis-isomers. $^1$H NMR (400 MHz, DMSO-d$_6$) δ 8.31 (s, 3H), 4.03 (ddd, J=10.8, 4.5, 2.2 Hz, 0.5H), 3.92 (d, J=12.6 Hz, 0.5H), 3.71-3.58 (m, 1H), 3.51 (ddp, J=8.8, 4.4, 2.1 Hz, 0.5H), 3.36 (s, 0.5H), 3.25 (s, 0.5H), 3.04 (s, 0.5H), 2.87-2.56 (m, 2H), 2.08 (d, J=12.7 Hz, 0.5H), 1.98-1.72 (m, 1.5H), 1.70-1.46 (m, 1.5H), 1.36 (qd, J=13.2, 3.9 Hz, 0.5H) ppm; $^{13}$C NMR (101 MHz, DMSO-d$_6$) δ 118.48 (118.33), 72.52 (72.07), 67.75 (67.56), 45.53 (44.36), 28.59 (24.33), 26.78 (24.06), 23.42 (23.14) ppm; LCMS calculated for $C_7H_{12}N_2O$: 140.2 (free amine). Found: 141 (M$^+$+H); Salt ratio (HCl to the free amine):1.00.

Example 2. 2-((2R,5S)-5-Aminotetrahydro-2H-pyran-2-yl)acetonitrile hydrochloride and 2-((2S, 5S)-5-aminotetrahydro-2H-pyran-2-yl)acetonitrile hydrochloride (Procedure 2)

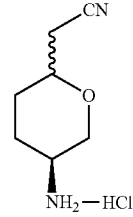

Step 1. methyl (4S)-4-[(tert-butoxycarbonyl)amino]-5-hydroxypentanoate

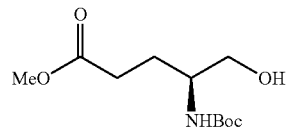 [SMILES: COC(=O)CC[C@@H](CO)NC(=O)OC(C)(C)C]

A solution of (2S)-2-[(tert-butoxycarbonyl)amino]-5-methoxy-5-oxopentanoic acid (40.00 g, 153.1 mmol) in tetrahydrofuran (600 mL) was treated with 4-methylmorpholine (17 g, 168.1 mmol, 1.1 eq.) at room temperature. The resulting mixture was cooled to 0° C. before being treated with ethyl chloroformate (18 g, 165.9 mmol, 1.08 eq.) dropwise. The resulting reaction mixture was stirred at 0° C. for an additional 20 minutes before being filtered through Celite. The Celite bed was washed with THF (50 mL) and the clear filtrate solution was cooled to 0° C. The cooled solution was then treated with solid NaBH$_4$ (3.00 g, 79.3 mmol, 0.52 eq.) followed by a solution of NaBH$_4$ (2.9 g, 76.1 mmol, 0.50 eq.) in diglyme (40 mL). The resulting reaction mixture was stirred at room temperature for 3 h before being treated with an aqueous 1.0 M HCl solution (100 mL). The mixture was then stirred at room temperature for 10 minutes. The inorganic solids were filtered off and rinsed with EtOAc (100 mL). Ethyl acetate (1100 mL) was then added into the filtrate and the combined filtrate solution was concentrated under reduced pressure to remove the solvents (1200 mL). The remaining mixture was then washed with saturated aqueous sodium bicarbonate (50 mL) and water (2×50 mL). The organic phase was then concentrated under reduced pressure to afford crude methyl (4S)-4-[(tert-butoxycarbonyl)amino]-5-hydroxypentanoate (37.9 g), which was used in the subsequent reaction without further purification.

Step 2. (S)-tert-butyl (6-oxotetrahydro-2H-pyran-3-yl)carbamate

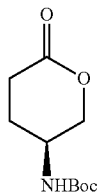 [SMILES: CC(C)(C)OC(=O)N[C@H]1CCC(=O)OC1]

A solution of crude methyl (4S)-4-[(tert-butoxycarbonyl)amino]-5-hydroxypentanoate (37.9 g, 153.1 mmol) in toluene (600 mL) and acetic acid (200 mL) was heated to reflux for 60 minutes. The solvents were then removed by the azeotropic distillation at atmospheric pressure. During the azeotropic distillation, an additional amount of toluene (600 mL) was introduced and a total of 1200 mL of the mixed solvents was removed. The residual mixture was then cooled to room temperature over 3 h and stirred at room temperature for 2 h. The solids were collected by filtration, washed with n-heptane (100 mL), and dried under reduced pressure at below 40° C. to afford the desired tert-butyl [(3S)-6-oxotetrahydro-2H-pyran-3-yl]carbamate (25 g, 75% overall yield for two steps). $^1$H NMR (400 MHz, CDCl$_3$) δ 4.39 (dd, J=11.5, 5.4 Hz, 1H), 4.18 (dd, J=11.4, 4 Hz, 1H), 4.00 (s, 1H), 2.69-2.54 (m, 2H), 2.22 (dq, J=13.2, 6.6 Hz, 1H), 1.86 (dq, J=14.6, 7.3 Hz, 1H), 1.43 (s, 9H); GCMS Calculated for C$_{10}$H$_{17}$NO$_4$: 215.25. Found: 215.1.

Step 3. tert-Butyl [(3S,6Z)-6-(cyanomethylene)tetrahydro-2H-pyran-3-yl]carbamate and tert-butyl [(3S,6E)-6-(cyanomethylene)tetrahydro-2H-pyran-3-yl]carbamate

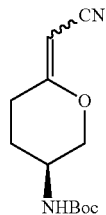

Method A.

A solution of cyanomethyl (trimethyl)phosphonium chloride (8.8 g, 58.06 mmol, 1.25 eq.) in N,N-dimethylacetamide (DMAC, 50 ml) was degassed and cooled to 0° C. The chilled solution was then treated with a solution of 1.0 M lithium hexamethyldisilazide in THF (LHMDS, 53.4 mL, 53.4 mmol, 1.15 eq.) at 0° C. The resulting mixture was stirred at 0° C. for 60 minutes before being treated with a solution of tert-butyl [(3S)-6-oxotetrahydro-2H-pyran-3-yl]carbamate (10 g, 46.46 mmol) in THF (40 mL) at 0° C. The reaction mixture was stirred at 0° C. for 2 h followed by stirring overnight at room temperature. The reaction mixture was then quenched with water (100 mL) and the two phases were separated. The aqueous phase was extracted with tert-butyl methyl ether (TBME, 2×150 mL). The combined organic phase was washed with water (2×150 mL) before being concentrated under reduced pressure to afford the crude desired product (11 g, 99%) as a mixture of tert-butyl [(3S,6Z)-6-(cyanomethylene)tetrahydro-2H-pyran-3-yl]carbamate and tert-butyl [3S,6E)-6-(cyanomethylene)tetrahydro-2H-pyran-3-yl]carbamate, which was used in the subsequent reaction without further purification and separation. Analytical samples of the individual isomers were obtained by silica gel column chromatography (SiO$_2$, gradient elution with 0-30% of t-Butyl methyl ether (MTBE) in heptane).

For (3S,6E)-isomer: $^1$H NMR (400 MHz, CDCl$_3$) δ 4.82 (s, 1H), 4.67 (s, 1H), 4.12 (dd, 1H), 3.93 (m, 1H), 3.81 (dd, 1H), 2.79 (dt, 1H), 2.58 (m, 1H), 2.12 (dt, 1H), 1.69 (dt, 1H), 1.40 (s, 9H); GCMS Calculated for C$_{12}$H$_{18}$N$_2$O$_3$: 238.28. Found: 238.1.

For (3S,6Z)-isomer: $^1$H NMR (400 MHz, CDCl$_3$) δ 4.81 (s, 1H), 4.48 (s, 1H), 4.19 (dt, 1H), 3.95 (m, 2H), 2.48 (m, 2H), 2.09 (m, 1H), 1.58 (m, 1H), 1.40 (s, 9H); GCMS Calculated for C$_{12}$H$_{18}$N$_2$O$_3$: 238.28. Found: 238.1.

Method B.

A mixture of tributyl(cyanomethyl)phosphonium chloride (593 g, 2.14 mol) in THF (5.9 L) was treated with solid potassium tert-butoxide (220 g, 1.97 mol) in portions at 0° C. over 5 minutes. The resulting mixture was gradually warmed to room temperature over 4 h. The resulting ylide solution was then treated with (S)-tert-butyl (6-oxotetrahydro-2H-pyran-3-yl)carbamate (184 g, 0.855 mol) as a solid at room temperature and the resulting reaction mixture was heated at 70° C. and stirred at 70° C. for 16 h. When NMR analysis indicated that the starting material was consumed, the reaction mixture was gradually cooled to room temperature. The resulting slurry was poured into a 50-L separation funnel containing saturated aqueous sodium bicarbonate (5 L) and ice (1000 g). Ethyl acetate (6 L) was added and the mixture was stirred for 10 minutes. The two layers were separated and the aqueous layer was extracted with EtOAc (3 L). The combined organic layers were washed with saturated aqueous sodium chloride (3×4 L), dried over sodium sulfate, and concentrated under reduced pressure. The resulting dark oil was dissolved in DCM (500 mL) and purified by column chromatography (SiO$_2$, gradient elution with 20-40% ethyl acetate in heptanes) to afford the desired product (177 g, 87% yield) as a mixture of tert-butyl [(3S,6Z)-6-(cyanomethylene)tetrahydro-2H-pyran-3-yl]carbamate and tert-butyl [(3S,6E)-6-(cyanomethylene)tetrahydro-2H-pyran-3-yl]carbamate, which was used in the subsequent reaction without further purification and separation. Analytical samples of the two isomers were obtained by silica gel column chromatography (SiO$_2$, gradient elution with 0-30% of t-butyl methyl ether (TBME) in heptane).

For (3S,6E)-isomer: $^1$H NMR (400 MHz, CDCl$_3$) δ 4.82 (s, 1H), 4.67 (s, 1H), 4.12 (dd, 1H), 3.93 (m, 1H), 3.81 (dd, 1H), 2.79 (dt, 1H), 2.58 (m, 1H), 2.12 (dt, 1H), 1.69 (dt, 1H), 1.40 (s, 9H); GCMS Calculated for $C_{12}H_{18}N_2O_3$: 238.28. Found: 238.1.

For (3S,6Z)-isomer: $^1$H NMR (400 MHz, CDCl$_3$) δ 4.81 (s, 1H), 4.48 (s, 1H), 4.19 (dt, 1H), 3.95 (m, 2H), 2.48 (m, 2H), 2.09 (m, 1H), 1.58 (m, 1H), 1.40 (s, 9H); GCMS Calculated for $C_{12}H_{18}N_2O_3$: 238.28. Found: 238.1.

Step 4. tert-Butyl [(3S,6S)-6-(cyanomethyl)tetrahydro-2H-pyran-3-yl]carbamate and tert-butyl [(3S,6R)-6-(cyanomethyl)tetrahydro-2H-pyran-3-yl]carbamate

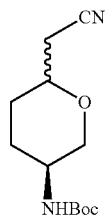

A mixture of tert-butyl [(3S,6Z)-6-(cyanomethylene)tetrahydro-2H-pyran-3-yl]carbamate and tert-butyl [(3S,6E)-6-(cyanomethylene)tetrahydro-2H-pyran-3-yl]carbamate (110 g, 0.462 mol) and palladium on carbon (10 wt % Pd-C, 50% wet, 14 g) in methanol (1.1 L) was hydrogenated at 20 psi until hydrogen uptake ceased (4 to 12 h). The reaction mixture was filtered through Celite (100 g) and the Celite bed was washed with methanol (500 mL). The combined filtrate was concentrated under reduced pressure to afford the crude reduction products as an off-white solid. The crude products were further dried by azeotropic distillation with toluene (2×500 mL) and n-heptane (2×500 mL) under reduced pressure to remove residual methanol and water to afford tert-butyl [3S,6S)-6-(cyanomethyl)tetrahydro-2H-pyran-3-yl]carbamate and tert-butyl [(3S,6R)-6-(cyanomethyl)tetrahydro-2H-pyran-3-yl]carbamate (111 g, nearly quantitative yield) as a mixture of diastereomers, which was used directly in the subsequent reaction without further purification and separation. $^1$H NMR (300 MHz, CDCl$_3$, as a mixture of two diastereomers) δ 5.15 (br s, 1H), 4.29 (br s, 1H), 4.14-4.07 (m, 1H), 3.94-3.87 (m, 1H), 3.77-3.44 (m, 5H), 3.09-3.01 (m, 1H), 2.58-2.49 (m, 4H), 2.18-2.09 (m, 1H), 2.05-1.95 (m, 1H), 1.92-1.81 (m, 1H), 1.76-1.51 (m, 5H), 1.46 (s, 9H), 1.44 (s, 9H); GCMS calculated for $C_{12}H_{20}N_2O_3$: 240.30. Found: 240.1.

Step 5. 2-((2S,5S)-5-Aminotetrahydro-2H-pyran-2-yl)acetonitrile hydrochloride and 2-((2R,5S)-5-aminotetrahydro-2H-pyran-2-yl)acetonitrile hydrochloride A solution of tert-butyl [(3S,6S)-6-(cyanomethyl)tetrahydro-2H-pyran-3-yl]carbamate and tert-butyl [(3S,6R)-6-(cyanomethyl)tetrahydro-2H-pyran-3-yl]carbamate (240 g, 0.999 mol) in dichloromethane (2.44 L) was treated with a solution of 4 M HCl in 1,4-dioxane (1 L, 3.99 mol, 4.0 eq.) dropwise over 30 minutes while keeping the internal temperature at below 25° C. The resulting reaction mixture was stirred at room temperature for 3 h. When $^1$H NMR analysis of the filtered sample indicated that the reaction was complete, tert-butyl methyl ether (TBME, 675 mL) was added to the reaction mixture and the resulting mixture was stirred at room temperature for 30 minutes. The white solids formed were collected by filtration under a blanket of nitrogen, washed with TBME (600 mL), and further dried in a vacuum oven under a blanket of nitrogen for 16 h to afford 2-((2S,5S)-5-aminotetrahydro-2H-pyran-2-yl)acetonitrile hydrochloride and 2-((2R,5S)-5-aminotetrahydro-2H-pyran-2-yl)acetonitrile hydrochloride (151.7 g, 86% yield) as a mixture of cis- and trans-isomers. $^1$H NMR (400 MHz, DMSO-d$_6$) (a mixture of cis- and trans-isomers) δ 8.31 (s, 3H), 4.03 (ddd, J=10.8, 4.5, 2.2 Hz, 0.5H), 3.92 (d, J=12.6 Hz, 0.5H), 3.71-3.58 (m, 1H), 3.51 (ddp, J=8.8, 4.4, 2.1 Hz, 0.5H), 3.36 (s, 0.5H), 3.25 (s, 0.5H), 3.04 (s, 0.5H), 2.87-2.56 (m, 2H), 2.08 (d, J=12.7 Hz, 0.5H), 1.98-1.72 (m, 1.5H), 1.70-1.46 (m, 1.5H), 1.36 (qd, J=13.2, 3.9 Hz, 0.5H) ppm; $^{13}$C NMR (101 MHz, DMSO-d$_6$) δ 118.48 (118.33), 72.52 (72.07), 67.75 (67.56), 45.53 (44.36), 28.59 (24.33), 26.78 (24.06), 23.42 (23.14) ppm; LCMS Calculated for $C_7H_{12}N_2O$: 140.2 (free amine). Found: 141 (M$^+$+H); salt ratio (HCl to the free amine):1.00.

Example 3. 2-((2R,5S)-5-(6-Nitrothieno[3,2-b]pyridin-7-ylamino)tetrahydro-2H-pyran-2-yl)acetonitrile and 2-((2S,5S)-5-(6-nitrothieno[3,2-b]pyridin-7-ylamino)tetrahydro-2H-pyran-2-yl)acetonitrile

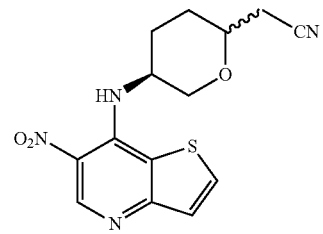 [SMILES: N#CCC1CC[C@H](Nc2c([N+](=O)[O-])cnc3ccsc23)CO1]

A mixture of 2-((2S,5S)-5-aminotetrahydro-2H-pyran-2-yl)acetonitrile hydrochloride and 2-((2R,5S)-5-aminotetrahydro-2H-pyran-2-yl)acetonitrile hydrochloride (2464 g, 13.95 mol, 1.16 eq.), and 7-chloro-6-nitrothieno[3,2-b]pyridine (2581 g, 12.02 mol) in N,N-dimethylformamide (DMF, 12.3 L) was treated with diisopropylethylamine (DIPEA, 4897 g, 46.13 mol, 3.84 eq.) at room temperature. The resulting reaction mixture was heated to 65-75° C. for 2-6 h until HPLC showed the reaction was complete. Water (36.9 L) was added to the reaction mixture at above 55° C. to precipitate the crude desired product and the resulting mixture was gradually cooled to 15-30° C. and stirred at 15-30° C. for 1-2 h. The yellow solids were collected by filtration, washed with water (36.9 L) and n-heptane (30.8 L), and dried in a vacuum oven at 45-50° C. to constant weight to afford the crude desired product (3550 g, 92.8%) as a mixture of 2-((2R,5S)-5-(6-nitrothieno[3,2-b]pyridin-7-ylamino)tetrahydro-2H-pyran-2-yl)acetonitrile and 2-((2S,5S)-5-(6-nitrothieno[3,2-b]pyridin-7-ylamino)tetrahydro-2H-pyran-2-yl)acetonitrile, which was used in the subsequent reaction without further purification and separation. Analytical samples of the cis-isomer and trans-isomer were obtained by column chromatography separation (SiO$_2$, gradient elution with 0-50% of ethyl acetate in heptane).

For (2R,5S)-isomer: $^1$H NMR (400 MHz, DMSO-d$_6$) δ 9.09 (s, 1H), 8.87 (d, J=9.1 Hz, 1H), 8.35 (d, J=5.5 Hz, 1H), 7.53 (d, J=5.5 Hz, 1H), 4.32 (ddq, J=14.4, 10.1, 4.3 Hz, 1H), 4.17 (ddd, J=10.9, 4.5, 2.2 Hz, 1H), 3.66 (ddd, J=9.2, 6.8, 4.5 Hz, 1H), 3.52 (t, J=10.6 Hz, 1H), 2.85 (dd, J=17.0, 4.4 Hz, 1H), 2.76 (dd, J=17.0, 6.8 Hz, 1H), 2.28-2.23 (m, 1H), 191-1.81 (m, 2H), 1.61-1.43 (m, 1H) ppm; $^{13}$C NMR (101 MHz, DMSO-d$_6$) δ 159.30, 147.11, 145.78, 136.17, 125.59, 125.47, 118.47, 116.54, 71.79, 70.18, 50.25, 29.95, 29.18, 23.14 ppm; $C_{14}H_{14}N_4O_3S$ (MW 318.3), LCMS (EI) m/e 319 (M$^+$+H).

For (2S,5S)-isomer: $^1$H NMR (400 MHz, DMSO-d$_6$) δ 9.69 (d, J=8.5 Hz, 1H), 9.14 (s, 1H), 8.37 (d, J=5.5 Hz, 1H), 7.54 (d, J=5.5 Hz, 1H), 4.49 (d, J=8.6 Hz, 1H), 4.03 (d, J=11.9 Hz, 1H), 3.89 (d, J=10.4 Hz, 1H), 3.75 (dd, J=7.1, 3.6 Hz, 1H), 2.84 (dd, J=17.1, 4.3 Hz, 1H), 2.71 (dd, J=17.1, 7.0 Hz, 1H), 2.07-2.04 (m, 2H), 1.75-1.40 (m, 2H) ppm; $^{13}$C NMR (101 MHz, DMSO-d$_6$) δ 159.15, 147.26, 145.49, 136.22, 125.56, 125.28, 118.16, 116.77, 72.53, 70.31, 47.99, 27.84, 25.08, 23.65 ppm; $C_{14}H_{14}N_4O_3S$ (MW 318.3), LCMS (EI) m/e 319 (M$^+$+H).

Example 4. 2-((2R,5S)-5-(6-Aminothieno[3,2-b]pyridin-7-ylamino)tetrahydro-2H-pyran-2-yl)acetonitrile and 2-((2S,5S)-5-(6-aminothieno[3,2-b]pyridin-7-ylamino)tetrahydro-2H-pyran-2-yl)acetonitrile

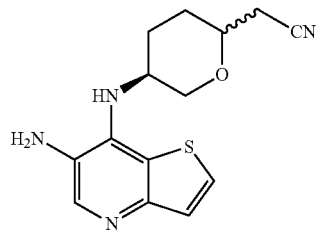 [SMILES: N#CCC1CC[C@H](Nc2c(N)cnc3ccsc23)CO1]

A solution of 2-((2R,5S)-5-(6-nitrothieno[3,2-b]pyridin-7-ylamino)tetrahydro-2H-pyran-2-yl)acetonitrile and 2-((2S,5S)-5-(6-nitrothieno[3,2-b]pyridin-7-ylamino)tetrahydro-2H-pyran-2-yl)acetonitrile (2000 g, 6.28 mol) in 2,2,2-trifluoroethanol (8.1 L) was treated with palladium on carbon (10 wt % Pd-C, 50% wet, 200 g) at room temperature. The resulting reaction mixture was degassed and refilled with nitrogen gas three times followed by hydrogen gas, three times. The hydrogenation reaction was run at 20-35° C. with 50 psi of hydrogen pressure. When HPLC showed the reaction was complete, the pressure was reduced to atmospheric before being degassed and refilled with nitrogen three times. The mixture was then filtered through Celite (667 g) and the Celite bed was rinsed with methanol (8 L). The filtrate was then concentrated under reduced pressure at below 50° C. to afford the desired crude product (2242 g) as a mixture of 2-((2R,5S)-5-(6-aminothieno[3,2-b]pyridin-7-ylamino)tetrahydro-2H-pyran-2-yl)acetonitrile and 2-((2S,5S)-5-(6-aminothieno[3,2-b]pyridin-7-ylamino)tetrahydro-2H-pyran-2-yl)acetonitrile. This mixture, obtained as foam which contained residual solvents was inseparable on a silica gel column, and was used in the subsequent reaction without further purification.

For (2R,5S)-isomer: $^1$H NMR (400 MHz, DMSO-d$_6$) δ 7.93 (s, 1H), 7.55 (d, J=5.6 Hz, 1H), 7.20 (d, J=5.6 Hz, 1H), 4.91 (d, J=9.7 Hz, 1H), 4.82 (s, 2H), 4.06-3.77 (m, 2H), 3.55 (dtt, J=8.7, 4.5, 2.1 Hz, 1H), 3.24 (t, J=10.3 Hz, 1H), 2.92-2.62 (m, 2H), 2.20-1.97 (m, 1H), 1.88-1.70 (m, 1H), 1.66-1.51 (m, 1H), 1.50-1.37 (m, 1H) ppm; $^{13}$C NMR (101 MHz, DMSO-d$_6$) δ 150.28, 136.88, 134.86, 128.10, 124.86, 124.82, 118.55, 117.95, 72.14, 71.70, 49.30, 30.79, 29.74, 23.32 ppm; $C_{14}H_{16}N_4OS$ (MW 288.3), LCMS (EI) m/e 289 (M$^+$+H).

For (2S,5S)-isomer: $^1$H NMR (400 MHz, DMSO-d$_6$) δ 8.01 (s, 1H), 7.59 (d, J=5.5 Hz, 1H), 7.22 (d, J=5.5 Hz, 1H), 5.09 (d, J=9.6 Hz, 1H), 4.76 (s, 2H), 3.99 (d, J=9.6 Hz, 1H), 3.87 (d, J=11.7 Hz, 1H), 3.75 (dd, J=11.7, 2.2 Hz, 1H), 3.66 (dddd, J=10.3, 7.2, 4.4, 2.6 Hz, 1H), 2.85-2.62 (m, 2H), 1.86-1.69 (m, 2H), 1.63 (qd, J=12.7, 12.2, 4.4 Hz, 1H), 1.52-1.44 (m, 1H) ppm; $^{13}$C NMR (101 MHz, DMSO-d$_6$) δ 150.81, 137.91, 135.84, 128.17, 125.36, 124.83, 118.71, 118.61, 72.37, 70.23, 46.81, 27.08, 24.94, 23.44 ppm; $C_{14}H_{16}N_4OS$ (MW 288.3), LCMS (EI) m/e 289 (M$^+$+H).

Example 5. 2-((2R,5S)-5-(2-((R)-1-Hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile

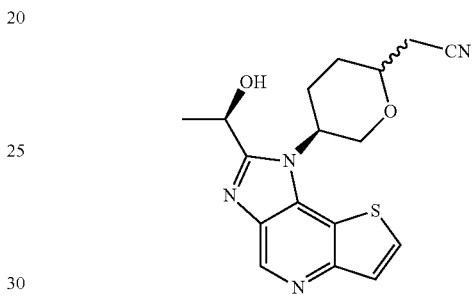

In reactor A, a suspension of (R)-(+)-lactamide (2045 g, 22.96 mol, 3.0 eq.) in THF (10.1 L) was treated with Et$_3$O—BF$_4$ (4405 g, 22.96 mol, 3.0 eq.) at −10 to 0° C. The resulting mixture in reactor A was then stirred at below 10° C. until a clear solution was formed. In reactor B, a mixture of 2-((2R,5S)-5-(6-aminothieno[3,2-b]pyridin-7-ylamino)tetrahydro-2H-pyran-2-yl)acetonitrile and 2-((2S,5S)-5-(6-aminothieno[3,2-b]pyridin-7-ylamino)tetrahydro-2H-pyran-2-yl)acetonitrile (2207 g, 7.65 mol) in ethanol (66.2 L) was heated to reflux to provide a clear solution. The solution in reactor A was then gradually added to the mixture in reactor B while maintaining the mixture in reactor B at reflux. The resulting reaction mixture in reactor B was maintained at reflux until HPLC showed the reaction was complete. The reaction mixture in reactor B was then cooled to 10-30° C. before an aqueous solution of sodium bicarbonate (664 g, 7.4 L) was gradually added. During addition of aqueous sodium bicarbonate to adjust the pH to 8-9, the internal temperature was controlled at below 35° C. The resulting mixture was then stirred at room temperature for an additional 30 minutes before being filtered through Celite (1 kg). After the filtration, the Celite bed was rinsed with ethanol (5.0 L). The combined filtrate was concentrated under reduced pressure at below 60° C. and dichloromethane (17.7 L) was added to dissolve the residue. The resulting DCM solution was then treated with a 1 N aqueous HCl solution (19.0 L) to adjust the pH of the aqueous phase to 1. The mixture was then stirred for 30 minutes at room temperature. The two phases were separated and the DCM phase was discarded. The acidic aqueous phase was then washed with DCM (8.6 L). The two phases were separated and the DCM phase was discarded. The acidic aqueous phase was then treated with ethyl acetate (30.6 L) followed by solid sodium carbonate (540 g). The resulting mixture was stirred at room temperature until the aqueous phase reached a pH of 9-10. n-Heptane (60.0 L) was then added to the mixture, and the resulting mixture was stirred at room temperature for at least 1 h. The solids were collected by filtration and washed with water (8.6 L) and n-heptane (8.6 L) before being dissolved in a mixture of methanol and DCM. The resulting solution of MeOH and DCM was then passed through a silica gel bed and the silica gel bed was washed with a mixture of MeOH and DCM (1 to 9 by volume). The combined solution was concentrated under reduced pressure to afford a first crop of the desired product (1450 g), a mixture 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile, as white foam. The two phases of the filtrate were then separated and the aqueous phase was extracted with DCM (2×25.0 L). The combined organic extracts were concentrated under reduced pressure and the residue was purified by silica gel column chromatography ($SiO_2$, gradient elution with 0.5% to 7.5% MeOH in DCM) to afford a second crop of the desired product (515 g; total 1965 g, 75%), also as a mixture 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile, as white foam. The mixture of two diastereomers was inseparable by silica gel column chromatography, and was used in the subsequent reaction without further separation.

For (2R,5S)-isomer: $^1$H NMR (500 MHz, DMSO-$d_6$) δ 9.00 (s, 1H), 8.03 (d, J=5.5 Hz, 1H), 7.69 (d, J=5.5 Hz, 1H), 5.96 (s, 1H), 5.22 (s, 1H), 5.11 (s, 1H), 4.31 (t, J=11.0 Hz, 1H), 4.22-4.08 (m, 1H), 4.02 (s, 1H), 2.96 (dd, J=17.0, 4.2 Hz, 1H), 2.84 (dd, J=17.0, 6.6 Hz, 1H), 2.65 (qd, J=12.7, 4.3 Hz, 1H), 2.19 (d, J=10.0 Hz, 1H), 2.06 (d, J=13.4 Hz, 1H), 1.72 (dd, J=12.6, 3.7 Hz, 1H), 1.66 (d, J=6.5 Hz, 3H) ppm; $^{13}$C NMR (101 MHz, DMSO-$d_6$) δ 157.95, 152.11, 141.57, 136.18, 135.24, 127.98, 126.79, 119.08, 116.12, 72.42, 68.87, 62.95, 51.67, 30.39, 28.44, 24.09, 22.36 ppm; $C_{17}H_{18}N_4O_2S$ (MW 342.4), LCMS (EI) m/e 343 ($M^+$+H).

For (2S,5S)-isomer: $^1$H NMR (400 MHz, $CD_3CN$) δ 8.93 (s, 1H), 7.80 (d, J=5.5 Hz, 1H), 7.63 (d, J=5.5 Hz, 1H), 5.38 (s, 1H), 5.00 (dq, J=9.4, 4.7 Hz, 1H), 4.43 (dd, J=11.8, 9.3 Hz, 1H), 4.26 (dd, J=8.6, 3.7 Hz, 1H), 4.16 (s, 1H), 4.03-3.89 (m, 1H), 3.17 (dd, J=17.1, 8.6 Hz, 1H), 2.87 (dd, J=17.2, 5.4 Hz, 1H), 2.57 (dtd, J=14.8, 10.8, 4.2 Hz, 1H), 2.20-1.99 (m, 2H), 1.88-1.82 (m, 1H), 1.73 (d, J=6.4 Hz, 3H) ppm; $^{13}$C NMR (101 MHz, $CD_3CN$) δ 158.04, 152.88, 142.12, 136.81, 136.46, 127.44, 127.14, 119.04, 116.97, 70.00, 64.83, 64.03, 54.55, 28.06, 25.73, 22.46, 21.94 ppm; $C_{17}H_{18}N_4O_2S$ (MW 342.4), LCMS (EI) m/e 343 ($M^+$+H).

Example 6. 2-(2R,5S)-5-(2-((R)-1-Hydroxyethyl)-1H-imidazo[4,5-d]thieno[3,2-b]pyridin-1-yl)tetrahydro-2H-pyran-2-yl)acetonitrile monohydrate (Crude Product)

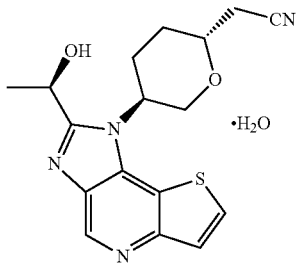

A mixture of 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile (800 g, 2.34 mol) in 2-propanol (IPA, 16 L) was treated with a solution of 1.0 M potassium tert-butoxide in THF (234 mL, 0.234 mol, 0.10 eq.) at room temperature. The resulting reaction mixture was stirred at room temperature for 20 h. When HPLC showed the base-promoted racemization reaction was complete, the reaction mixture was treated with a 0.1 M aqueous HCl solution (approximately 2.4 L) to adjust the pH to 6-7. The mixture was then concentrated under reduced pressure at below 50° C. to partially remove IPA (approximately 9.6 L) and the residue was treated with water (10.5 L) at room temperature. The resulting mixture was then stirred at room temperature for 2 h. The solids were collected by filtration, washed with a mixture of IPA and water (2.4 L, 1 to 2 by volume), and dried under reduced pressure at below 50° C. to constant weight to provide crude 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile monohydrate (657 g, 78%) as a white solid. $^1$H NMR (500 MHz, DMSO-$d_6$) δ 9.00 (s, 1H), 8.03 (d, J=5.5 Hz, 1H), 7.69 (d, J=5.5 Hz, 1H), 5.96 (s, 1H), 5.22 (s, 1H), 5.11 (s, 1H), 4.31 (t, J=11.0 Hz, 1H), 4.22-4.08 (m, 1H), 4.02 (s, 1H), 2.96 (dd, J=17.0, 4.2 Hz, 1H), 2.84 (dd, J=17.0, 6.6 Hz, 1H), 2.65 (qd, J=12.7, 4.3 Hz, 1H), 2.19 (d, J=10.0 Hz, 1H), 2.06 (d, J=13.4 Hz, 1H), 1.72 (dd, J=12.6, 3.7 Hz, 1H), 1.66 (d, J=6.5 Hz, 3H) ppm; $^{13}$C NMR (101 MHz, DMSO-$d_6$) δ 157.95, 152.11, 141.57, 136.18, 135.24, 127.98, 126.79, 119.08, 116.12, 72.42, 68.87, 62.95, 51.67, 30.39, 28.44, 24.09, 22.36 ppm; $C_{17}H_{18}N_4O_2S$ (MW 342.4), LCMS (EI) m/e 343 ($M^+$+H); water content by KF: 5.15%.

Example 7. 2-(2R,5S)-5-(2-((R)-1-Hydroxyethyl)-1H-imidazo[4,5-d]thieno[3,2-b]pyridin-1-yl)tetrahydro-2H-pyran-2-yl)acetonitrile (Anhydrous Crystalline Free Base)

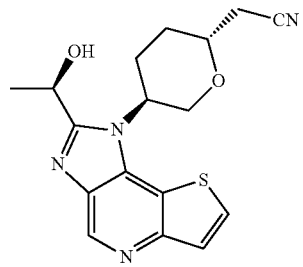 [SMILES: C[C@@H](O)c1nc2cnc3ccsc3c2n1[C@H]1CC[C@H](CC#N)OC1]

A solution of 2-((2R,5S)-5-(2#R)-1-hydroxyethyl)-1H-imidazo[4,5-d]thieno[3,2-b]pyridin-1-yl)tetrahydro-2H-pyran-2-yl)acetonitrile monohydrate (650 g, 1.80 mol) in methanol (7 L) was polish filtered before being concentrated at atmospheric pressure to remove methanol (5 L). The resulting concentrated solution was then treated with ethyl acetate (8.5 L) and the atmospheric distillation was continued to remove solvents (5.3 L). n-Heptane (7.8 L) was then gradually added to the residual mixture at 60-75° C. and the resulting mixture was gradually cooled down to room temperature and stirred at room temperature for at least 1.5 h. The solids were collected by filtration, washed with n-heptane (2.0 L), and dried in vacuum at below 50° C. to constant weight to afford anhydrous crystalline 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile (586 g, 95%) as a white solid. $^1$H NMR (500 MHz, DMSO-$d_6$) δ 9.00 (s, 1H), 8.03 (d, J=5.5 Hz, 1H), 7.69 (d, J=5.5 Hz, 1H), 5.96 (s, 1H), 5.22 (s, 1H), 5.11 (s, 1H), 4.31 (t, J=11.0 Hz, 1H), 4.22-4.08 (m, 1H), 4.02 (s, 1H), 2.96 (dd, J=17.0, 4.2 Hz, 1H), 2.84 (dd, J=17.0, 6.6 Hz, 1H), 2.65 (qd, J=12.7, 4.3 Hz, 1H), 2.19 (d, J=10.0 Hz, 1H), 2.06 (d, J=13.4 Hz, 1H), 1.72 (dd, J=12.6, 3.7 Hz, 1H), 1.66 (d, J=6.5 Hz, 3H) ppm; $^{13}$C NMR (101 MHz, DMSO-$d_6$) δ 157.95, 152.11, 141.57, 136.18, 135.24, 127.98, 126.79, 119.08, 116.12, 72.42, 68.87, 62.95, 51.67, 30.39, 28.44, 24.09, 22.36 ppm; $C_{17}H_{18}N_4O_2S$ (MW 342.4), LCMS (EI) m/e 343 (M$^+$+H).

Example 8. 2-(2R,5S)-5-(2-((R)-1-Hydroxyethyl)-1H-imidazo[4,5-d]thieno[3,2-b]pyridin-1-yl)tetrahydro-2H-pyran-2-yl)acetonitrile Monohydrate

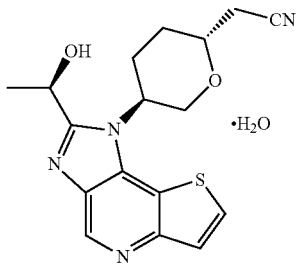

A suspension of anhydrous crystalline 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile (585 g, 1.71 mol) in water (5.9 L) was stirred at room temperature for 2 h. When XRPD confirmed that the conversion of the anhydrous crystalline form to the monohydrate crystalline form was complete, the solids were collected by filtration and washed with water (2.9 L). The wet cake was dried at 20-50° C. either in a vacuum oven or by pulling a vacuum from the filter until the water content analyzed by KF was 5±0.3% to afford crystalline 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile monohydrate (602 g, 98%) as a white solid. $^1$H NMR (500 MHz, DMSO-$d_6$) δ 9.00 (s, 1H), 8.03 (d, J=5.5 Hz, 1H), 7.69 (d, J=5.5 Hz, 1H), 5.96 (s, 1H), 5.22 (s, 1H), 5.11 (s, 1H), 4.31 (t, J=11.0 Hz, 1H), 4.22-4.08 (m, 1H), 4.02 (s, 1H), 2.96 (dd, J=17.0, 4.2 Hz, 1H), 2.84 (dd, J=17.0, 6.6 Hz, 1H), 2.65 (qd, J=12.7, 4.3 Hz, 1H), 2.19 (d, J=10.0 Hz, 1H), 2.06 (d, J=13.4 Hz, 1H), 1.72 (dd, J=12.6, 3.7 Hz, 1H), 1.66 (d, J=6.5 Hz, 3H) ppm; $^{13}$C NMR (101 MHz, DMSO-$d_6$) δ 157.95, 152.11, 141.57, 136.18, 135.24, 127.98, 126.79, 119.08, 116.12, 72.42, 68.87, 62.95, 51.67, 30.39, 28.44, 24.09, 22.36 ppm; LCMS Calculated for: $C_{17}H_{18}N_4O_2S$: 342.4. Found: 343 (M$^+$+H); Water content: 5.15%.

Example 9. 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile (Anhydrous Crystalline Free Base)

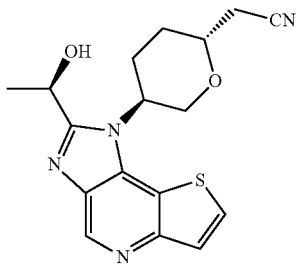 [SMILES: C[C@@H](O)c1nc2cnc3ccsc3c2n1[C@H]1CC[C@H](CC#N)OC1]

A solution of amorphous ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile (84.5 g, 247 mmol) in methanol (MeOH, 800 mL) was polish filtered and transferred into a 5-neck 5 L round bottom flask equipped with a reflux condenser. Additional 200 mL of methanol was used to wash the filter funnel. To the resulted methanol solution, ethyl acetate (2000 mL) was added and the resulting clear solution was heated to 70° C. over 30 minutes. The mixture of methanol and ethyl acetate was then distilled at atmospheric pressure. An additional 2000 mL of ethyl acetate was added when the collected solvent mixture reached 1700 mL and the atmospheric distillation was continued. When the total collected solvent mixture reached 4000 mL (in about 8 h), the remaining solution in the flask became cloudy and solids gradually formed. The atmospheric distillation was continued until the total collected solvent mixture reached 4250 mL, and the remaining solvent mixture, mainly ethyl acetate, in the flask was about 750 mL. n-Heptane (1150 mL) was then added slowly to the flask at approximately 70° C. (EtOAc to n-Heptane approximately at 1 to 1.5), and the resulting mixture was gradually cooled to room temperature. The mixture was agitated at room temperature for an additional 2-3 h to initiate crystallization. The solids were collected by filtration, washed with n-heptane (2×300 mL), and dried at 50° C. in vacuum oven with $N_2$ sweeping to afford ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile (78.1 g, 92.4%) as white anhydrous crystalline powder.

$C_{17}H_{18}N_4O_2S$ (MW 342.42), LCMS (EI) m/e 343 (M$^+$+H); $^1$H NMR (400 MHz, DMSO-$d_6$) δ 9.00 (s, 1H), 8.03 (d, J=5.5 Hz, 1H), 7.69 (d, J=5.5 Hz, 1H), 5.97 (s, 1H), 5.22 (s, 1H), 5.11 (s, 1H), 4.30 (t, J=11.0 Hz, 1H), 4.17 (s, 1H), 4.02 (s, 1H), 2.96 (dd, J=17.0, 4.2 Hz, 1H), 2.86 (dd, J=17.0, 6.6 Hz, 1H), 2.76-2.56 (m, 1H), 2.19 (d, J=10.6 Hz, 1H), 2.06 (d, J=13.2 Hz, 1H), 1.72 (dd, J=12.6, 3.7 Hz, 1H), 1.66 (d, J=6.5 Hz, 3H) ppm; $^{13}$C NMR (100 MHz, DMSO-$d_6$) δ 157.95, 152.11, 141.57, 136.18, 135.24, 127.98, 126.79, 119.08, 116.12, 72.42, 68.87, 62.95, 51.67, 30.39, 28.44, 24.09, 22.36 ppm.; water content by KF: 1.15% by weight. The DSC thermogram shown in FIG. 1 revealed one endothermic event with an onset at 185.05° C., which relates to the compound melting, and the peak at 189.71° C. The endothermic event at about 260° C. associated with the decomposition of the compound. The TGA thermogram shown in FIG. 2 revealed a weight loss of 1.25% up to 200° C. Significant weight loss was observed at temperatures above 200° C. due to decomposition of the compound. The XRPD pattern was determined for the title compound and is shown in FIG. 3. A list of 2-theta peaks is provided in Table 2 below.

TABLE 2

| 2-Theta | d (A) | Net Intensity | Gross Intensity | Relative Intensity (%) |
|---|---|---|---|---|
| 6.608 | 13.3654 | 608 | 931 | 2.7 |
| 8.802 | 10.0379 | 8330 | 8970 | 37.6 |
| 9.699 | 9.1114 | 1560 | 2280 | 7.0 |
| 10.016 | 8.8244 | 2260 | 3010 | 10.2 |
| 10.574 | 8.3595 | 6020 | 6800 | 27.2 |
| 13.207 | 6.6983 | 2970 | 3870 | 13.4 |
| 14.509 | 6.1000 | 1490 | 2560 | 6.7 |
| 15.092 | 5.8659 | 3980 | 5180 | 18.0 |
| 16.329 | 5.4241 | 21900 | 23300 | 98.8 |
| 16.889 | 5.2454 | 1350 | 2870 | 6.1 |
| 17.554 | 5.0482 | 5510 | 7120 | 24.9 |

TABLE 2-continued

| 2-Theta | d (A) | Net Intensity | Gross Intensity | Relative Intensity (%) |
|---|---|---|---|---|
| 18.017 | 4.9194 | 4010 | 5680 | 18.1 |
| 19.081 | 4.6474 | 11000 | 12800 | 49.6 |
| 19.726 | 4.4971 | 3490 | 5320 | 15.8 |
| 21.174 | 4.1927 | 7880 | 9770 | 35.6 |
| 21.648 | 4.1018 | 2740 | 4640 | 12.4 |
| 22.466 | 3.9544 | 1080 | 2980 | 4.9 |
| 23.387 | 3.8007 | 3290 | 5160 | 14.9 |
| 24.037 | 3.6993 | 12100 | 13900 | 54.7 |
| 25.096 | 3.5456 | 626 | 2370 | 2.8 |
| 26.204 | 3.3980 | 5000 | 6720 | 22.6 |
| 26.420 | 3.3708 | 6510 | 8220 | 29.4 |
| 26.858 | 3.3169 | 1190 | 2880 | 5.4 |
| 27.681 | 3.2201 | 1320 | 2970 | 6.0 |
| 27.933 | 3.1916 | 1200 | 2830 | 5.4 |
| 29.318 | 3.0439 | 1060 | 2600 | 4.8 |
| 31.169 | 2.8672 | 1510 | 2870 | 6.8 |
| 31.300 | 2.8555 | 1560 | 2910 | 7.1 |
| 33.466 | 2.6755 | 607 | 1730 | 2.7 |
| 35.550 | 2.5233 | 826 | 1820 | 3.7 |
| 40.831 | 2.2083 | 501 | 1450 | 2.3 |
| 41.961 | 2.1514 | 966 | 1920 | 4.4 |
| 44.759 | 2.0232 | 618 | 1520 | 2.8 |
| 51.694 | 1.7669 | 229 | 1020 | 1.0 |

Example 10. 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile monohydrate

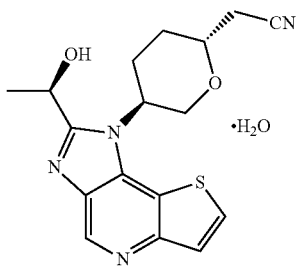

In a 2-L round bottom flask equipped with a reflux condenser, a thermocouple and a magnetic stirring bar, was charged amorphous 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile (93.0 g, 272 mmol) and isopropyl alcohol (IPA, 1116 mL) at room temperature. The resulting suspension was heated to 50-55° C. to obtain a clear solution. The solution was polish filtered through a filter funnel at 50° C. An additional amount of isopropyl alcohol (IPA, 47 mL) was used to wash the filter funnel. To the combined solution was added water (930 mL) over 30 minutes while maintaining the internal temperature at 45-50° C. White precipitate gradually appeared upon the addition of the water. The IPA was removed by rotary evaporation under vacuum with a water bath at 50° C. During the distillation, an additional amount of water (1209 mL) was added to keep the total volume of the mixture at about 1500 mL. After the vacuum distillation, the resulting mixture was gradually cooled to room temperature and agitated at room temperature for 1-2 h. The solids were collected by filtration, washed with water (186 mL), and dried on a filter funnel with a housing vacuum at room temperature for 16 h to afford 2-((2R,5S)-5-(2-((R)-1-hydroxyethyl)-1H-imidazo[4,5-d]thieno[3,2-b]pyridin-1-yl) tetrahydro-2H-pyran-2-yl)acetonitrile monohydrate (91.6 g, 94%) as white crystalline powder. $^1$H NMR (500 MHz, DMSO-$d_6$) δ 9.00 (s, 1H), 8.03 (d, J=5.5 Hz, 1H), 7.69 (d, J=5.5 Hz, 1H), 5.96 (s, 1H), 5.22 (s, 1H), 5.11 (s, 1H), 4.31 (t, J=11.0 Hz, 1H), 4.22-4.08 (m, 1H), 4.02 (s, 1H), 2.96 (dd, J=17.0, 4.2 Hz, 1H), 2.84 (dd, J=17.0, 6.6 Hz, 1H), 2.65 (qd, J=12.7, 4.3 Hz, 1H), 2.19 (d, J=10.0 Hz, 1H), 2.06 (d, J=13.4 Hz, 1H), 1.72 (dd, J=12.6, 3.7 Hz, 1H), 1.66 (d, J=6.5 Hz, 3H) ppm; $^{13}$C NMR (101 MHz, DMSO-$d_6$) δ 157.95, 152.11, 141.57, 136.18, 135.24, 127.98, 126.79, 119.08, 116.12, 72.42, 68.87, 62.95, 51.67, 30.39, 28.44, 24.09, 22.36 ppm; $C_{17}H_{18}N_4O_2S$ (MW 342.42), LCMS (EI) m/e 343 (M$^+$+H). Water content by KF: 5.15% by weight. The melting/decomposition range was determined by DSC and is shown in FIG. 4. The DSC thermogram revealed one dehydration endothermic event with an onset at 69.37° C. and the peak at 106.41° C., followed by the melting with an onset at 131.01° C. and a peak at 139.99° C. The TGA thermogram (FIG. 5) showed a weight loss of 4.9% up to 150° C., which corresponds to the water content of the mono-hydrate. After 200° C. the compound starts to decompose. The XRPD pattern was determined for the title compound and is shown in FIG. 6. A list of 2-theta peaks is provided in Table 3 below.

TABLE 3

| 2-Theta | d (A) | Net Intensity | Gross Intensity | Relative Intensity (%) |
|---|---|---|---|---|
| 8.477 | 10.4224 | 28200 | 28700 | 91.9 |
| 8.678 | 10.1819 | 14500 | 15000 | 47.3 |
| 11.368 | 7.7776 | 2600 | 3320 | 8.5 |
| 13.150 | 6.7274 | 564 | 1320 | 1.8 |
| 13.568 | 6.5211 | 162 | 922 | 0.5 |
| 14.592 | 6.0656 | 23400 | 24300 | 76.1 |
| 15.064 | 5.8765 | 21200 | 22100 | 69.0 |
| 15.789 | 5.6082 | 9180 | 10100 | 29.9 |
| 16.917 | 5.2369 | 6130 | 7140 | 19.9 |
| 17.427 | 5.0846 | 3000 | 4020 | 9.8 |
| 18.599 | 4.7668 | 7670 | 8720 | 25.0 |
| 19.388 | 4.5747 | 20300 | 21400 | 66.2 |
| 20.160 | 4.4011 | 4640 | 5700 | 15.1 |
| 21.091 | 4.2089 | 6690 | 7710 | 21.8 |
| 21.463 | 4.1368 | 839 | 1840 | 2.7 |
| 22.460 | 3.9554 | 3070 | 4150 | 10.0 |
| 22.871 | 3.8853 | 1370 | 2510 | 4.5 |
| 23.366 | 3.8040 | 6710 | 7900 | 21.8 |
| 23.503 | 3.7822 | 8550 | 9750 | 27.8 |
| 24.518 | 3.6279 | 706 | 2000 | 2.3 |
| 25.065 | 3.5499 | 29900 | 31200 | 97.3 |
| 25.674 | 3.4670 | 3830 | 5200 | 12.4 |
| 25.878 | 3.4401 | 11100 | 12500 | 36.2 |
| 26.306 | 3.3857 | 12500 | 13900 | 40.7 |
| 26.547 | 3.3549 | 18100 | 19500 | 58.9 |
| 27.574 | 3.2323 | 6810 | 8210 | 22.2 |
| 28.299 | 3.1511 | 717 | 2100 | 2.3 |
| 28.625 | 3.1160 | 3130 | 4490 | 10.2 |
| 29.200 | 3.0559 | 1670 | 3000 | 5.4 |
| 29.828 | 2.9930 | 1100 | 2370 | 3.6 |
| 30.451 | 2.9332 | 3810 | 5010 | 12.4 |
| 30.715 | 2.9085 | 5430 | 6600 | 17.7 |
| 31.001 | 2.8823 | 1830 | 2960 | 6.0 |
| 31.335 | 2.8524 | 1820 | 2910 | 5.9 |
| 32.496 | 2.7531 | 420 | 1420 | 1.4 |
| 33.388 | 2.6815 | 4050 | 5030 | 13.2 |
| 34.026 | 2.6327 | 1220 | 2180 | 4.0 |
| 34.291 | 2.6130 | 861 | 1800 | 2.8 |
| 35.285 | 2.5416 | 724 | 1630 | 2.4 |
| 35.729 | 2.5111 | 1990 | 2900 | 6.5 |
| 36.639 | 2.4507 | 684 | 1590 | 2.2 |
| 36.931 | 2.4320 | 744 | 1640 | 2.4 |
| 37.470 | 2.3983 | 2760 | 3630 | 9.0 |
| 37.686 | 2.3850 | 1160 | 2020 | 3.8 |
| 39.059 | 2.3043 | 567 | 1430 | 1.8 |
| 39.713 | 2.2678 | 767 | 1680 | 2.5 |

TABLE 3-continued

| 2-Theta | d (A) | Net Intensity | Gross Intensity | Relative Intensity (%) |
|---|---|---|---|---|
| 40.791 | 2.2103 | 908 | 1870 | 3.0 |
| 41.862 | 2.1563 | 2100 | 3070 | 6.8 |
| 42.406 | 2.1298 | 511 | 1470 | 1.7 |
| 43.684 | 2.0704 | 531 | 1430 | 1.7 |
| 44.647 | 2.0280 | 1760 | 2680 | 5.7 |
| 45.207 | 2.0042 | 462 | 1430 | 1.5 |
| 45.857 | 1.9773 | 428 | 1430 | 1.4 |
| 47.419 | 1.9157 | 1510 | 2540 | 4.9 |
| 47.976 | 1.8947 | 1750 | 2780 | 5.7 |
| 48.744 | 1.8667 | 896 | 1890 | 2.9 |
| 49.480 | 1.8406 | 470 | 1420 | 1.5 |
| 51.479 | 1.7737 | 811 | 1630 | 2.6 |
| 52.307 | 1.7476 | 452 | 1270 | 1.5 |
| 53.685 | 1.7060 | 321 | 1130 | 1.0 |

Example 11. Dynamic Vapor Sorption

Figure 9:
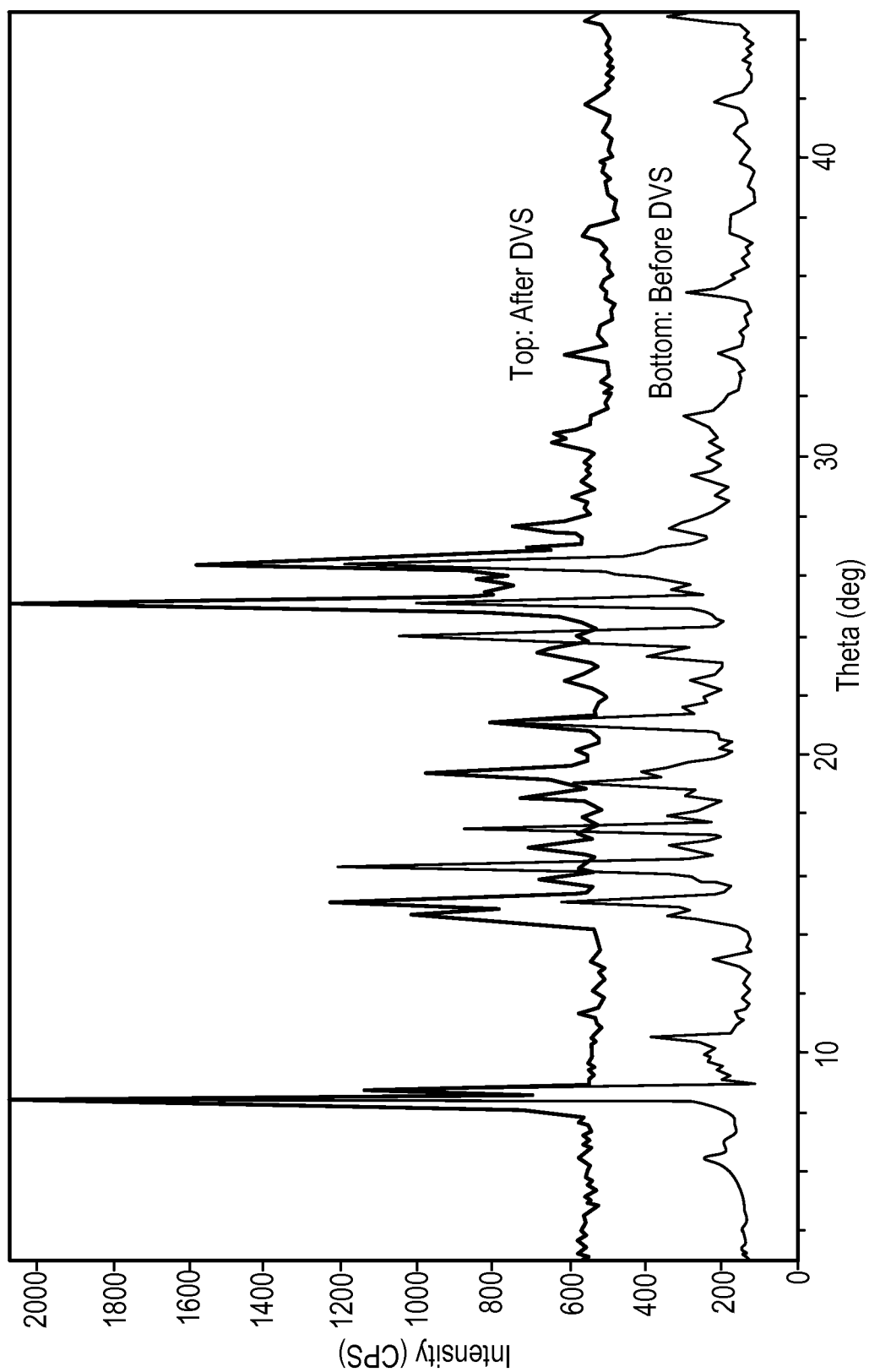
FIG. 9 shows an XRPD pattern overlay of the compound of Example 9 before and after a Dynamic Vapor Sorption (DVS) study.

A Dynamic Vapor Sorption (DVS) study was conducted on the compound of Example 9 to monitor the hydroscopicity, hydrate formation and dehydration, as well as solid form transformation. The moisture uptake profile was completed in four cycles in 10% relative humidity (RH) increments with the first adsorption from 25% to 95% RH, followed by desorption in 10% increments from 95% to 5% RH. The equilibration criteria were as follows: 0.0050 wt % in 5 minutes with a maximum equilibration time of 180 minutes. All adsorption and desorption were performed at room temperature (25° C.). No pre-drying step was applied for the sample. Water absorption of the anhydrous form was slow below 85% RH and fast above 85% RH. Changes in the XRPD patterns before and after DVS suggest solid form change. After DVS cycle 4, the anhydrous form was fully converted to the hydrate form. Under ambient storage conditions, the anhydrous form will slowly absorb water and convert to hydrate form. The dehydration process from the hydrate to the anhydrous form is very slow, even at 5% RH. The hydrate form is physically stable in a wide range of humidity conditions. Vapor sorption/desorption isotherms are shown in FIG. 7 and FIG. 8. An XRPD pattern overlay before and after DVS is shown in FIG. 9.

Example 12. Humidity Chamber Study A

Figure 10:
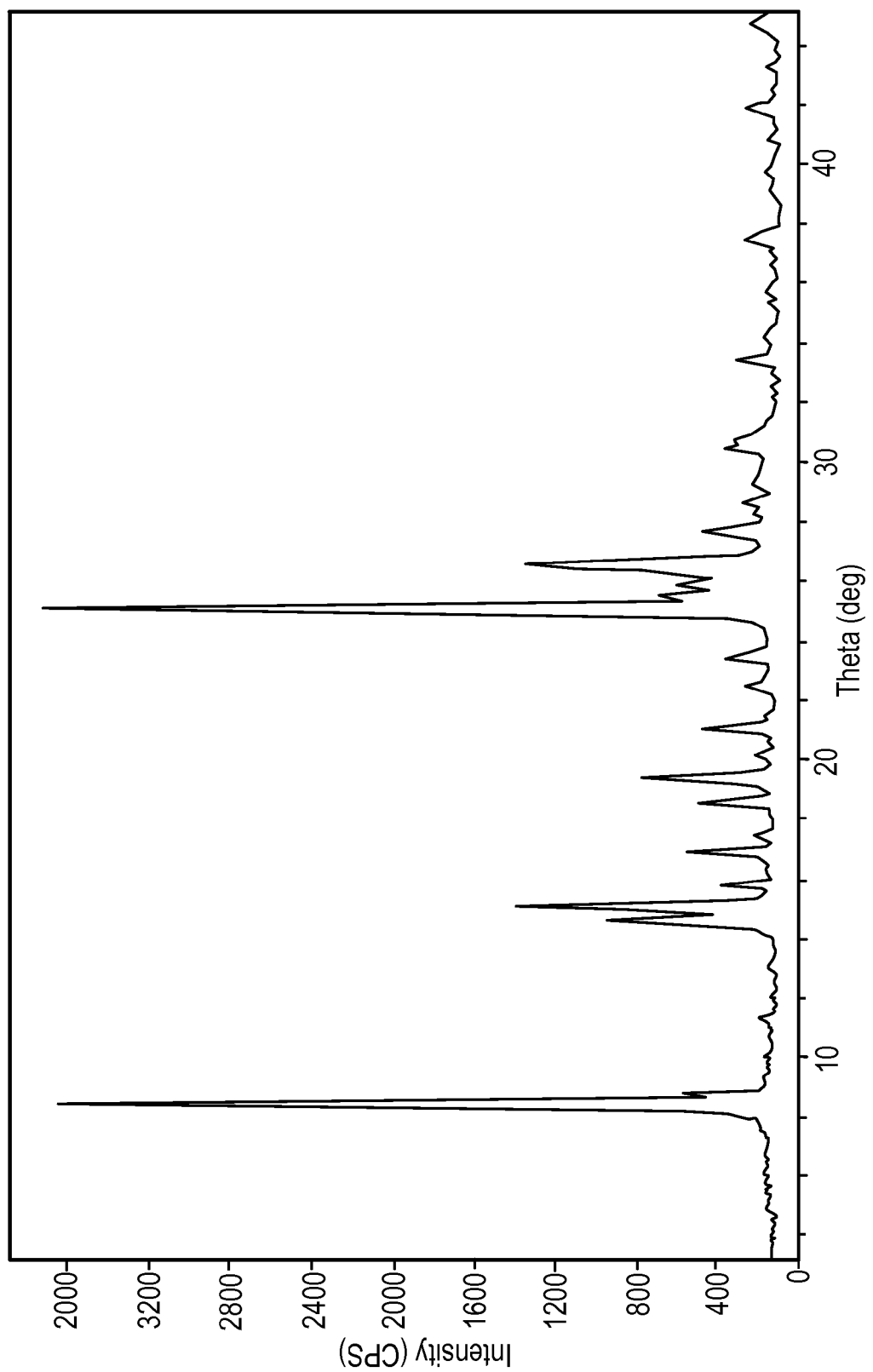
FIG. 10 shows an XRPD pattern characteristic of the compound of Example 9 after 5 days in a humidity chamber set at 75% relative humidity and 40° C.
Figure 11:
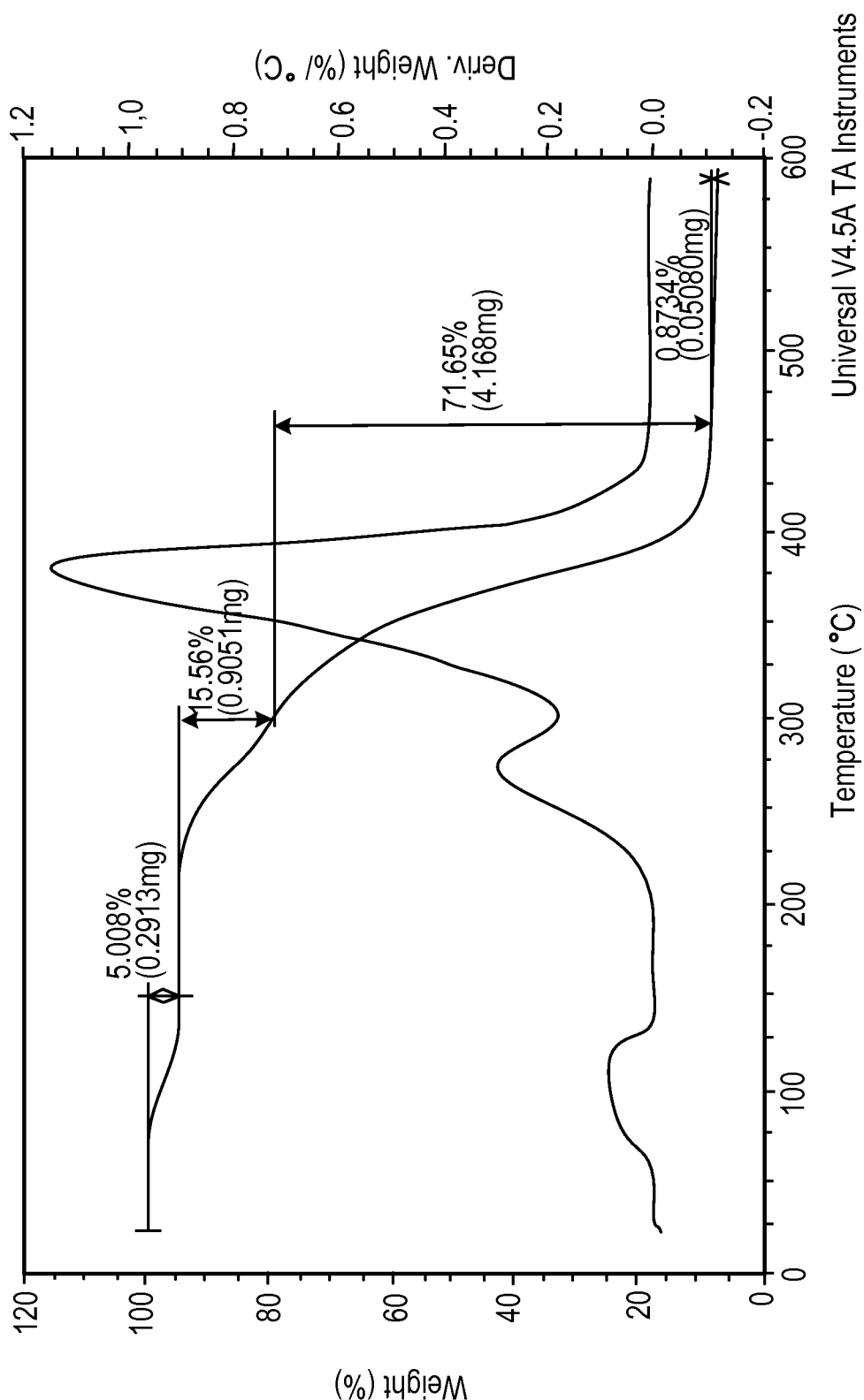
FIG. 11 shows a TGA thermogram characteristic of the compound of Example 9 after 5 days in a humidity chamber set at 75% relative humidity and 40° C.
Figure 12:
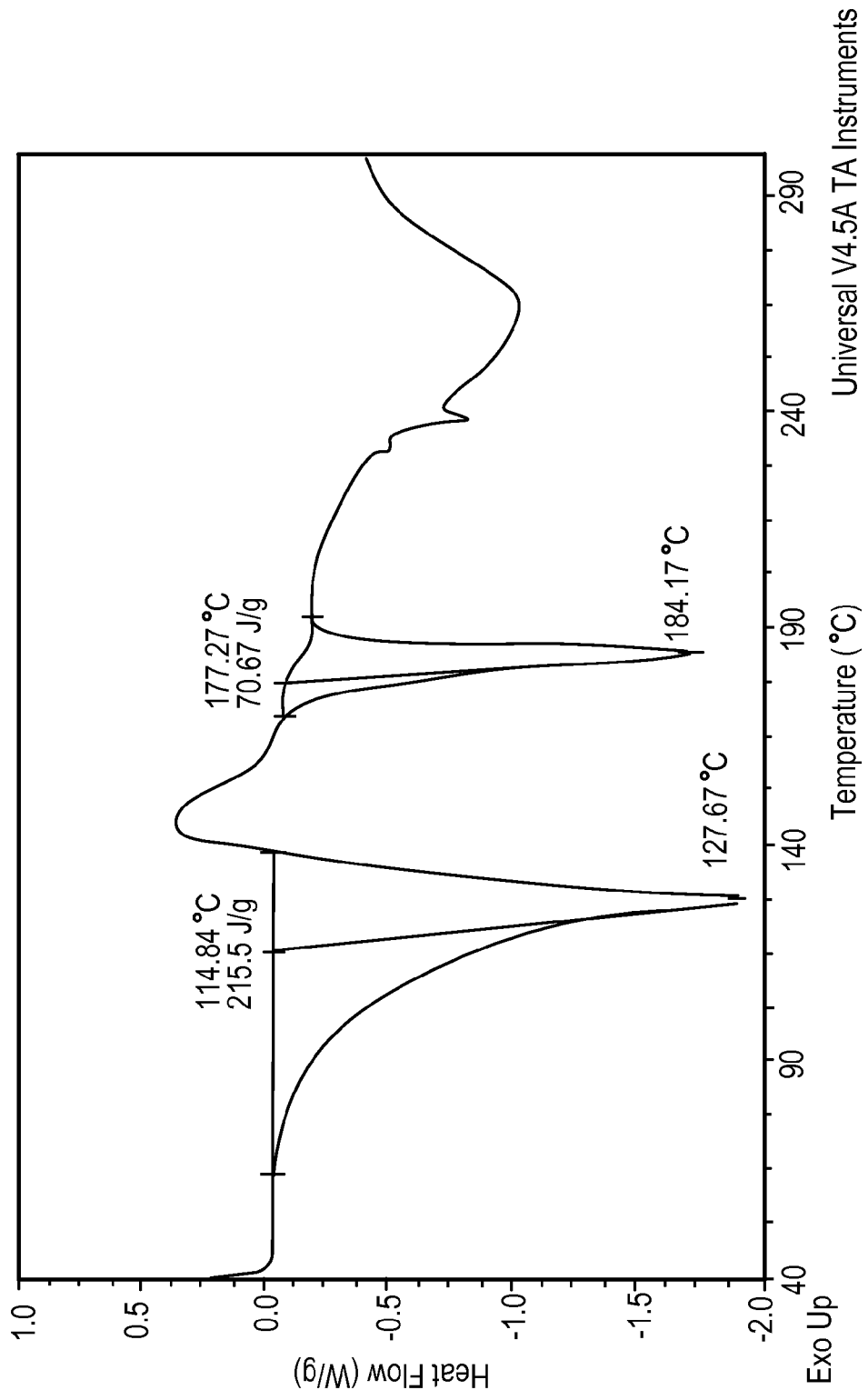
FIG. 12 shows a DSC thermogram of the compound of Example 9 after 5 days in a humidity chamber set at 75% relative humidity and 40° C.

The compound of Example 9 was placed in a humidity chamber set at 40° C. and 75% relative humidity for 5 days. The resulting sample was analyzed by XRPD, TGA, and DSC as shown in FIGS. 10 to 12. Based on XRPD data, the anhydrous crystalline free base was converted to the crystalline hydrate form. The water content by KF was 4.6% and the weight loss observed by TGA was 5.01%.

Example 13. Humidity Chamber Study B

Figure 13:
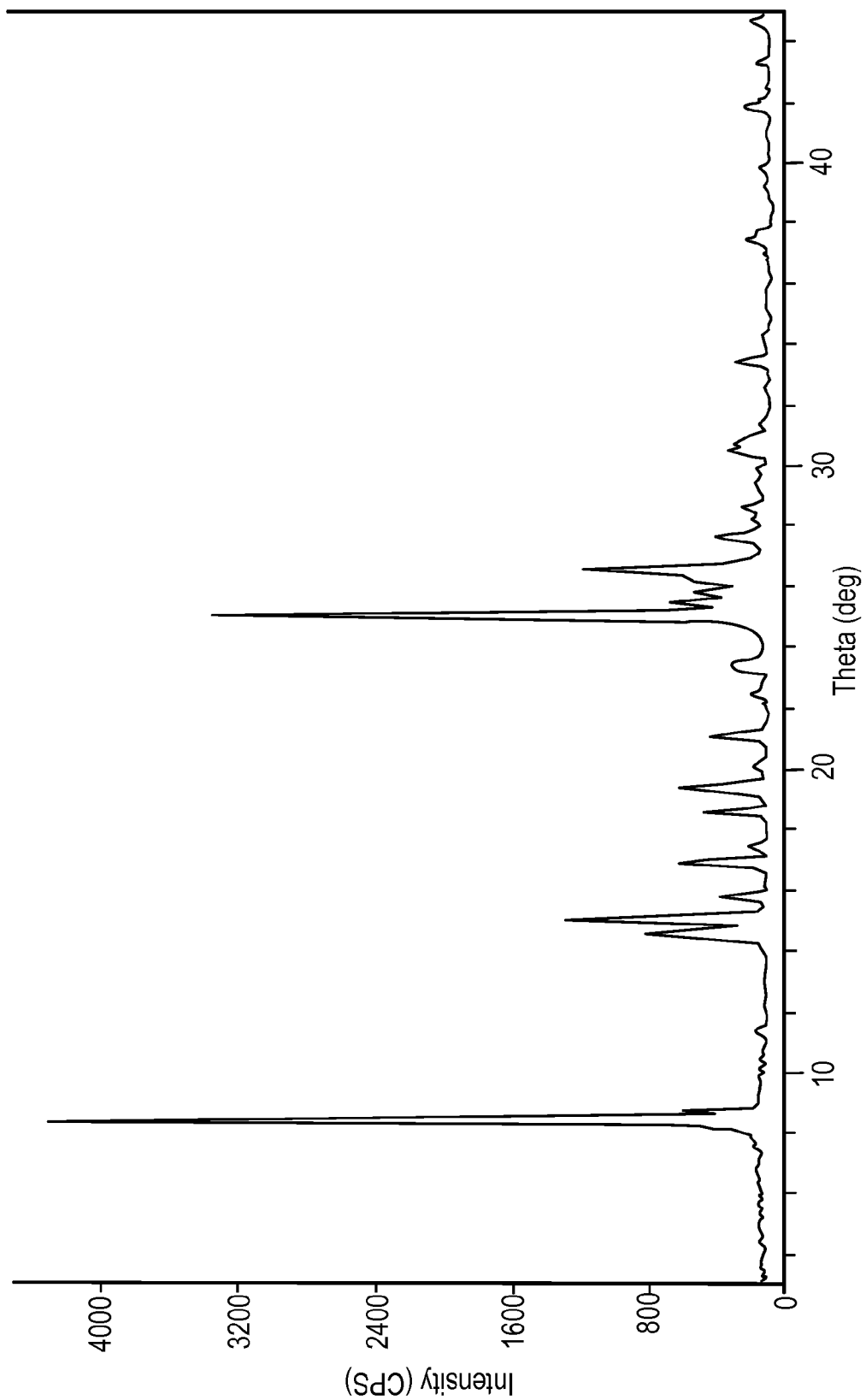
FIG. 13 shows an XRPD pattern characteristic of the compound of Example 9 after 7 days in a humidity chamber set at 90% relative humidity and 30° C.
Figure 14:
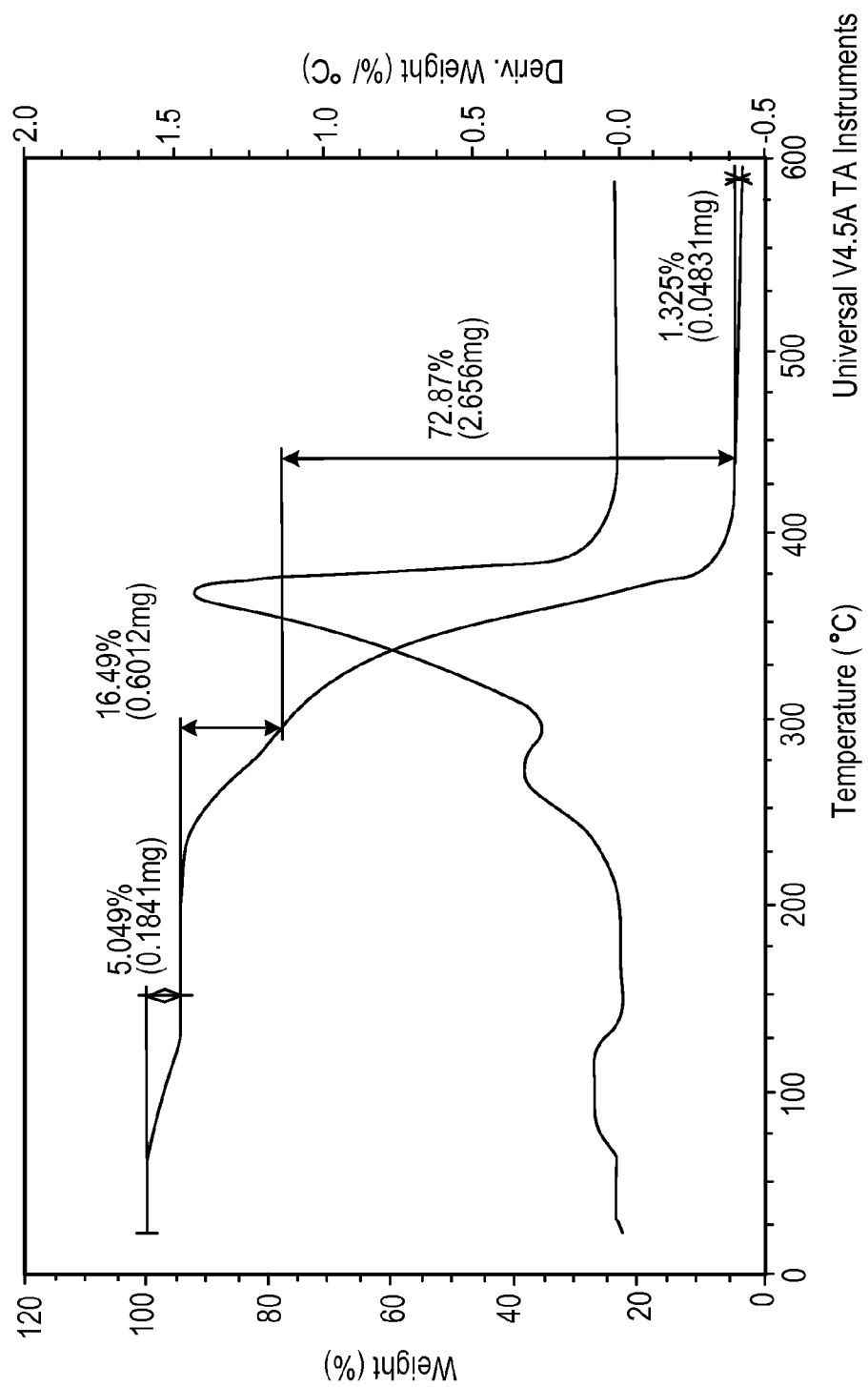
FIG. 14 shows a TGA thermogram of the compound of Example 9 after 7 days in a humidity chamber set at 90% relative humidity and 30° C.
Figure 15:
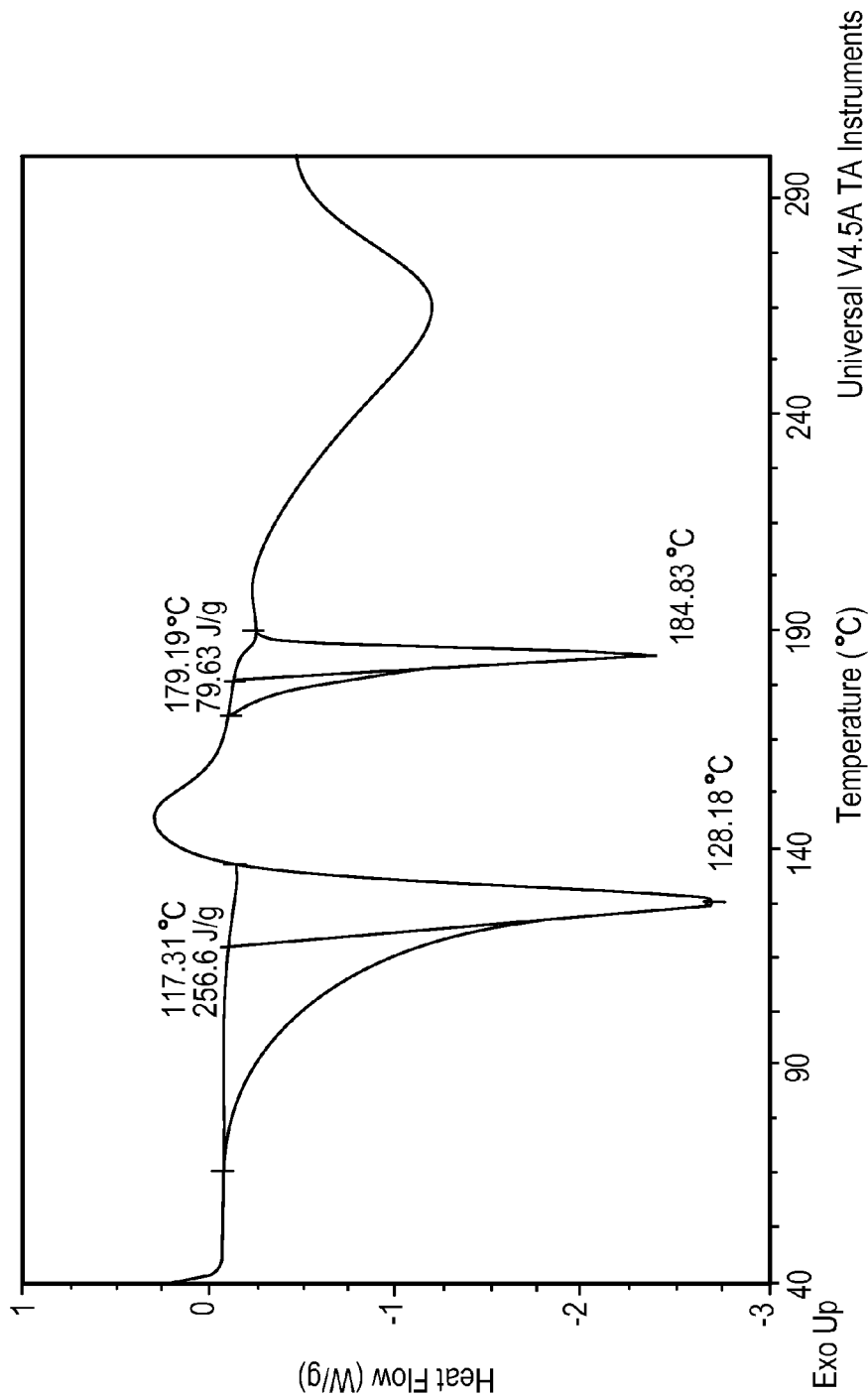
FIG. 15 shows a DSC thermogram of the compound of Example 9 after 7 days in a humidity chamber set at 90% relative humidity and 30° C.

The compound of Example 9 was placed in a humidity chamber set at 30° C. and 90% relative humidity (RH) for 7 days. The resulting sample was analyzed by XRPD, TGA, and DSC as shown in FIGS. 13 to 15. Based on XRPD, the anhydrous crystalline free base was converted to the crystalline hydrate form. The XRPD patterns of the 30° C./90% RH sample corresponded to the hydrate form obtained from an aqueous suspension of the anhydrous crystalline free base drug substance. The water content by KF was 4.72% and the weight loss observed by TGA was 5.05%.

Example 14. (R)-4-methoxy-2,2,5-trimethyl-2,5-dihydrooxazole

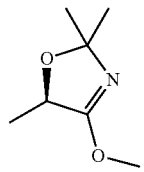

Step 1. (R)-2,2,5-Trimethyloxazolidin-4-one

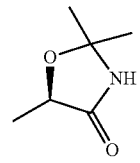

To a solution of (2R)-2-hydroxypropanamide (30 g, 337 mmol) in acetone was added 2,2-dimethoxypropane (51.8 mL, 421 mmol, 1.25 equiv) and boron trifluoride diethyl etherate (BF$_3$-Et$_2$O, 92.13 mL, 16.8 mmol, 0.05 equiv) at room temperature. The resulting reaction mixture was then stirred at room temperature overnight. When TLC indicated the reaction was complete, the solvent was removed under reduced pressure at below 35° C. and the residue was added to methyl t-butyl ether (MTBE, 350 mL). The solution was treated with saturated aqueous sodium bicarbonate (NaHCO$_3$) solution (15 mL), solid sodium bicarbonate (NaHCO$_3$, 4 g), and solid sodium sulfate (Na$_2$SO$_4$, 30 g) and the resulting mixture was stirred at room temperature for 30 minutes. The solids were filtered off and washed with methyl t-butyl ether (MTBE, 50 mL). The two phases of the combined filtrates were separated and the organic phase was washed with water (30 mL) and dried with sodium sulfate (Na$_2$SO$_4$, 20 g). After removal of the drying agent, the filtrate was concentrated under reduced pressure and the solvent was switched into n-hexane to provide desired product. The solids were collected by filtration, washed with n-hexane and dried to give the desired product, (R)-2,2,5-trimethyloxazolidin-4-one, (42 g, 97%) as white crystalline solids. $^1$H NMR (400 MHz, CD$_2$Cl$_2$) δ 7.66 (s, 1H), 4.37 (q, J=6.7 Hz, 1H), 1.47 (s, 3H), 1.44 (s, 3H), 1.36 (d, J=6.7 Hz, 3H) ppm; $^{13}$C NMR (101 MHz, CD$_2$Cl$_2$) δ 175.58 (s), 90.70 (s), 73.76 (s), 29.97 (s), 28.52 (s), 18.60 (s) ppm.

Step 2. (R)-4-Methoxy-2, 2, 5-trimethyl-2,5-dihydrooxazole

To a solution of (R)-2,2,5-trimethyloxazolidin-4-one (20 g, 155 mmol) in dichloromethane (DCM, 200 mL) was added trimethoxonium tetrafluoride (Me$_3$O$^+$BF$_4^-$, 24.1 g, 155 mmol, 1.0 equiv) at room temperature. The resulting reaction mixture was stirred at room temperature for 6 hours. When $^1$H-NMR indicated the reaction was complete, the reaction mixture was added to dichloromethane (DCM, 100 mL) and cooled to 0-5° C. The resulting solution was then treated with a 2M aqueous sodium carbonate solution (Na$_2$CO$_3$, 230 mL) while maintaining the internal temperature at 0-5° C. The two phases were separated and the organic phase was washed with water (2×100 mL), dried over sodium sulfate (Na$_2$SO$_4$, 50 g), and concentrated under reduced pressure to give the crude desired product, (R)-4-methoxy-2,2,5-trimethyl-2,5-dihydrooxazole, (19 g, 87%) as yellow oil, which can be directly used for the subsequent reaction without further purification. The pure desired product (12 g; by 50° C. at 50 mba) was obtained by vacuum distillation as colorless oil. $^1$H NMR (400 MHz, CD$_2$Cl$_2$) δ 4.58 (q, J=6.6 Hz, 1H), 3.80 (s, 3H), 1.41 (s, 3H), 1.35 (s, 3H), 1.29 (d, J=6.6 Hz, 3H) ppm; $^{13}$C NMR (101 MHz, CD$_2$Cl$_2$) δ 169.80 (s), 103.90 (s), 75.08 (s), 56.46 (s), 30.50 (s), 28.69 (s), 20.07 (s) ppm.

Example 15. Alternative preparation of 2-((2R,5S)-5-(2-((R)-1-Hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile

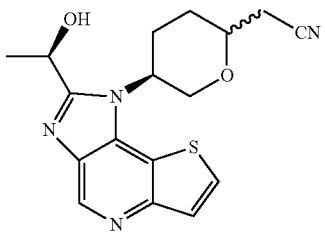 [SMILES: C[C@@H](O)c1nc2cnc3ccsc3c2n1[C@H]1CCC(CC#N)OC1]

To a flask was added (R)-2,2,5-trimethyloxazolidin-4-one (6.7 g, 52 mmol), trimethyloxonium tetrafluoroborate (Me$_3$O$^+$BF$_4^-$, 7.7 g, 52 mmol), and anhydrous dichloromethane (DCM, 50 mL) at room temperature. The resulting mixture was stirred at room temperature for 2 hours. When $^1$H NMR revealed that the formation of (R)-4-methoxy-2,2,5-trimethyl-2,5-dihydrooxazole was complete, the reaction mixture was charged with a mixture of 2-((2R,5S)-5-(6-aminothieno[3,2-b]pyridin-7-ylamino)tetrahydro-2H-pyran-2-yl)acetonitrile and 2-((2S,5S)-5-(6-aminothieno[3,2-b]pyridin-7-ylamino)tetrahydro-2H-pyran-2-yl)acetonitrile (Example 4, 5.0 g, 17.3 mmol) at room temperature. The solvent was then switched into methanol (80 mL) by addition of methanol to the reaction mixture and distillation to remove dichloromethane. The resulting reaction mixture was then heated to 65° C. for 1.5 hours. When HPLC showed the reaction was complete, the solvent was removed under reduced pressure and the residue was treated with dichloromethane (80 mL). The resulting mixture was then treated with saturated aqueous sodium bicarbonate solution (NaHCO$_3$, 10 mL) followed by solid NaHCO$_3$ (11.6 g, 139 mmol) before being stirred at room temperature for 30 min. The mixture was dried over Na$_2$SO$_4$ and the liquid was filtered. The solids were removed by filtration and the two phases of the filtrate were separated. The organic phase was washed with water (2×25 mL), dried over Na$_2$SO$_4$, and concentrated. The residue was then dissolved in 0.1 M aqueous hydrochloric acid (HCl) and the resulting acidic aqueous solution was washed with dichloromethane (2×20 mL). The acidic aqueous solution was then neutralized with NaHCO$_3$ to precipitate the crude desired product. The solids were collected by filtration, washed with water, and dried to give the desired product (5.0 g, 84% yield) as a mixture of 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile.

The mixture of two diastereomers is inseparable by silica gel column chromatography and was used directly in the subsequent reaction (see, e.g., Example 6) without further separation.

For (2R,5S)-isomer: $^1$H NMR (500 MHz, DMSO-d$_6$) δ 9.00 (s, 1H), 8.03 (d, J=5.5 Hz, 1H), 7.69 (d, J=5.5 Hz, 1H), 5.96 (s, 1H), 5.22 (s, 1H), 5.11 (s, 1H), 4.31 (t, J=11.0 Hz, 1H), 4.22-4.08 (m, 1H), 4.02 (s, 1H), 2.96 (dd, J=17.0, 4.2 Hz, 1H), 2.84 (dd, J=17.0, 6.6 Hz, 1H), 2.65 (qd, J=12.7, 4.3 Hz, 1H), 2.19 (d, J=10.0 Hz, 1H), 2.06 (d, J=13.4 Hz, 1H), 1.72 (dd, J=12.6, 3.7 Hz, 1H), 1.66 (d, J=6.5 Hz, 3H) ppm; $^{13}$C NMR (101 MHz, DMSO-d$_6$) δ 157.95, 152.11, 141.57, 136.18, 135.24, 127.98, 126.79, 119.08, 116.12, 72.42, 68.87, 62.95, 51.67, 30.39, 28.44, 24.09, 22.36 ppm; C$_{17}$H$_{18}$N$_4$O$_2$S (MW 342.4), LCMS (EI) m/e 343 (M$^+$+H).

For (2S,5S)-isomer: $^1$H NMR (400 MHz, CD$_3$CN) δ 8.93 (s, 1H), 7.80 (d, J=5.5 Hz, 1H), 7.63 (d, J=5.5 Hz, 1H), 5.38 (s, 1H), 5.00 (dq, J=9.4, 4.7 Hz, 1H), 4.43 (dd, J=11.8, 9.3 Hz, 1H), 4.26 (dd, J=8.6, 3.7 Hz, 1H), 4.16 (s, 1H), 4.03-3.89 (m, 1H), 3.17 (dd, J=17.1, 8.6 Hz, 1H), 2.87 (dd, J=17.2, 5.4 Hz, 1H), 2.57 (dtd, J=14.8, 10.8, 4.2 Hz, 1H), 2.20-1.99 (m, 2H), 1.88-1.82 (m, 1H), 1.73 (d, J=6.4 Hz, 3H) ppm; $^{13}$C NMR (101 MHz, CD$_3$CN) δ 158.04, 152.88, 142.12, 136.81, 136.46, 127.44, 127.14, 119.04, 116.97, 70.00, 64.83, 64.03, 54.55, 28.06, 25.73, 22.46, 21.94 ppm; C$_{17}$H$_{18}$N$_4$O$_2$S (MW 342.4), LCMS (EI) m/e 343 (M$^+$+H).

Example 16. Alternative Preparation of 2-((2R,5S)-5-(2-((R)-1-Hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile

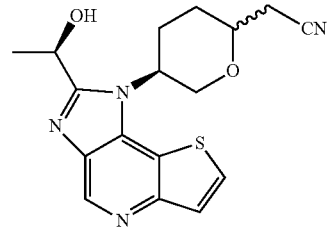 [SMILES: C[C@@H](O)c1nc2cnc3ccsc3c2n1[C@H]1CCC(CC#N)OC1]

Step 1. (R)-1-Amino-1-oxopropan-2-yl acetate

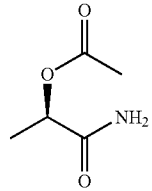

To a 1-L 3-necked round bottom flask equipped with a reflux condenser, a nitrogen inlet, a thermal couple and a magnetic stirring bar under nitrogen was charged (R)-2-hydroxypropanamide (49.95 g, 543.8 mmol) and tetrahydrofuran (THF, 300 mL) at room temperature. The resulting yellow solution was cooled to 0-5° C. by an ice-water bath before acetyl chloride (40.60 mL, 571.0 mmol, 1.05 equiv) was charged while maintaining the internal temperature at below 20° C. After the internal temperature was dropped back to below 5° C., 4-methylmorpholine (59.2 mL, 538.0 mmol, 0.99 equiv) was charged while maintaining the internal temperature to below 10° C. The resulting reaction mixture was then stirred at room temperature for 4 hours before the mixture was filtered to remove the solids. The solids were washed with THF (60 mL) and the filtrate was concentrated under reduced pressure to provide the crude desired product, (R)-1-amino-1-oxopropan-2-yl acetate, (75.0 g, 105.2%) as a white to off-white solid, which was used directly in next reaction without further purification. $^1$H NMR (400 MHz, DMSO-$d_6$) δ 7.42 (s, 1H), 7.14 (s, 1H), 4.84 (q, J=7.6 Hz, 1H), 2.03 (s, 3H), 1.29 (d, J=7.6 Hz, 3H) ppm.

Step 2. (R)-1-Cyanoethyl acetate

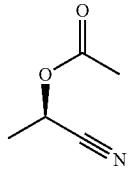

To a 3-L 3-necked round bottom flask equipped with a reflux condenser, a nitrogen inlet, a thermal couple and a magnetic stirring bar under nitrogen was charged crude (R)-1-amino-1-oxopropan-2-yl acetate (70.0 g, 533.8 mmol) and N,N-dimethylformamide (DMF, 280 mL) at room temperature. The resulting light yellow solution was then treated with cyanuric chloride (44.0 g, 240.0 mmol) in 2-methoxy-2-methylpropane (TBME, 600 mL) at room temperature. The reaction mixture was stirred at room temperature for 16 hours. The white solids were filtered and washed with TBME (800 mL). The combined organic filtrates were washed sequentially with saturated aqueous sodium bicarbonate solution (NaHCO$_3$, 200 mL), water (4×200 mL), and brine (100 mL). The resultant organic phase was then dried with anhydrous MgSO$_4$ (15 g) and concentrated under reduced pressure to provide the crude desired product, (R)-1-cyanoethyl acetate, (42.03 g, 69.6%) as a colorless to light yellow oil, which was used directly in the subsequent reaction without further purification. $^1$H NMR (400 MHz, DMSO-$d_6$) δ 5.46 (q, J=7.6 Hz, 1H), 2.09 (s, 3H), 1.53 (d, J=7.6 Hz, 3H) ppm.

Step 3. (R)-ethyl 2-hydroxypropanimidate

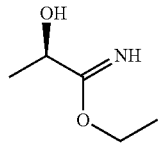

To a 100-mL round bottom flask equipped with a magnetic stirring bar was charged crude (R)-1-cyanoethyl acetate (1.021 g, 8.665 mmol) and ethanol (EtOH, 1.518 mL, 26.0 mmol) at room temperature. The resulting solution was then cooled to −40° C. before being bubbled in hydrogen chloride (HCl) gas for 45 seconds. The reaction mixture was then gradually warmed to room temperature. After 16 hours, the reaction mixture was cooled to 0° C. before tetrahydrofuran (THF, 2.0 mL, 25 mmol) and 4-methylmorpholine (0.865 mL, 7.87 mmol) were sequentially charged. The solids were removed by filtration and the crude desired product, (R)-ethyl 2-hydroxypropanimidate, in the filtrate was used directly in the subsequent reaction without further purification. $^1$H NMR (300 MHz, DMSO-$d_6$) δ 11.14 (s, 1H), 4.52-4.40 (m, 3H), 1.36-1.31 (m, 6H) ppm.

Step 4. 2-((2R,5S)-5-(2-((R)-1-Hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile To a 3-necked 100-mL round bottom flask equipped with a nitrogen inlet, a thermocouple and a magnetic stirring bar under nitrogen was charged a mixture of 2-((2R,5S)-5-(6-aminothieno[3,2-b]pyridin-7-ylamino)tetrahydro-2H-pyran-2-yl)acetonitrile and 2-((2S,5S)-5-(6-aminothieno[3,2-b]pyridin-7-ylamino)tetrahydro-2H-pyran-2-yl)acetonitrile (Example 4, 0.30 g, 1.04 mmol) in ethanol (EtOH, 4.0 mL) at room temperature. The mixture was then heated to 80° C. to provide a clear solution before a solution of the crude (R)-ethyl 2-hydroxypropanimidate in THF generated in previous step was added to the ethanol solution at 80° C. When the reaction was completed after 1 hour as indicated by HPLC, the reaction mixture was cooled to room temperature. The cooled reaction mixture was filtered and the filtrate was concentrated under reduced pressure to afford the crude desired product (0.3 g, 84% yield) as a mixture of 2-((2R,5S)-5-(2-((R)-1-hydroxyethyl)-1H-imidazo[4,5-d]thieno[3,2-b]pyridin-1-yl)tetrahydro-2H-pyran-2-yl)acetonitrile and 2-((2S,5S)-5-(2-((R)-1-hydroxyethyl)-1H-imidazo[4,5-d]thieno[3,2-b]pyridin-1-yl)tetrahydro-2H-pyran-2-yl)acetonitrile, which is inseparable by silica gel column chromatography and was used directly in the subsequent reaction without further separation (see, e.g., Example 6).

For (2R,5S)-isomer: $^1$H NMR (500 MHz, DMSO-$d_6$) δ 9.00 (s, 1H), 8.03 (d, J=5.5 Hz, 1H), 7.69 (d, J=5.5 Hz, 1H), 5.96 (s, 1H), 5.22 (s, 1H), 5.11 (s, 1H), 4.31 (t, J=11.0 Hz, 1H), 4.22-4.08 (m, 1H), 4.02 (s, 1H), 2.96 (dd, J=17.0, 4.2 Hz, 1H), 2.84 (dd, J=17.0, 6.6 Hz, 1H), 2.65 (qd, J=12.7, 4.3 Hz, 1H), 2.19 (d, J=10.0 Hz, 1H), 2.06 (d, J=13.4 Hz, 1H), 1.72 (dd, J=12.6, 3.7 Hz, 1H), 1.66 (d, J=6.5 Hz, 3H) ppm; $^{13}$C NMR (101 MHz, DMSO-$d_6$) δ 157.95, 152.11, 141.57, 136.18, 135.24, 127.98, 126.79, 119.08, 116.12, 72.42, 68.87, 62.95, 51.67, 30.39, 28.44, 24.09, 22.36 ppm; C$_{17}$H$_{18}$N$_4$O$_2$S (MW 342.4), LCMS (EI) m/e 343 (M$^+$+H).

For (2S,5S)-isomer: $^1$H NMR (400 MHz, CD$_3$CN) δ 8.93 (s, 1H), 7.80 (d, J=5.5 Hz, 1H), 7.63 (d, J=5.5 Hz, 1H), 5.38 (s, 1H), 5.00 (dq, J=9.4, 4.7 Hz, 1H), 4.43 (dd, J=11.8, 9.3 Hz, 1H), 4.26 (dd, J=8.6, 3.7 Hz, 1H), 4.16 (s, 1H), 4.03-3.89 (m, 1H), 3.17 (dd, J=17.1, 8.6 Hz, 1H), 2.87 (dd, J=17.2, 5.4 Hz, 1H), 2.57 (dtd, J=14.8, 10.8, 4.2 Hz, 1H), 2.20-1.99 (m, 2H), 1.88-1.82 (m, 1H), 1.73 (d, J=6.4 Hz, 3H) ppm; $^{13}$C NMR (101 MHz, CD$_3$CN) δ 158.04, 152.88, 142.12, 136.81, 136.46, 127.44, 127.14, 119.04, 116.97, 70.00, 64.83, 64.03, 54.55, 28.06, 25.73, 22.46, 21.94 ppm; C$_{17}$H$_{18}$N$_4$O$_2$S (MW 342.4), LCMS (EI) m/e 343 (M$^+$+H).

Example A: In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) were expressed using baculovirus in insect cells and purified. The catalytic activity of JAK1, JAK2 or JAK3 was assayed by measuring the phosphorylation of a biotinylated peptide. The phosphorylated peptide was detected by homogenous time resolved fluorescence (HTRF). $IC_{50}$s of compounds were measured for each kinase in the 40 µL, reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hour and then stopped with 20 µL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a PHERAi star plate reader (BMG, Cary, N.C.). The compound of Formula Ia was tested in the Example A assay at 1 mM ATP and found to have an $IC_{50}$ at JAK1 of ≤100 nM and an $IC_{50}$ at JAK2 of ≤1000 nM with a JAK2/JAK1 ratio>10.

Example B: Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% $CO_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art. To assess compound effects on JAK2, primary cells or cell lines can be stimulated with JAK2-dependent growth factors such as GM-CSF or Tpo, proteins extracted from cells and analyzed by techniques familiar to those schooled in the art including Western blotting or ELISAs using antibodies that can differentiate between phosphorylated and total protein.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. *JBC* 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/mL penicillin, 100 µg/ml streptomycin) at a density of $2 \times 10^6$ cells/ml at 37° C. for up to 2 days. For IL-2 stimulated cell proliferation analysis, T-cells are first treated with Phytohemagglutinin (PHA) at a final concentration of 10 µg/mL for 72 hours. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C: In Vivo Anti-Tumor Efficacy

Compounds herein can be evaluated in human tumor xenograft models in immune compromised mice. For example, a tumorigenic variant of the NA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D: Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E: In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; Methods in Molecular Biology: Vol. 225, Inflammation Protocols., Winyard, P. G. and Willoughby, D. A., Humana Press, 2003.).

Example F: Animal Models for the Treatment of Dry Eye, Uveitis, and Conjunctivitis Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent auto-immune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged occuarly with the same antigen. The EIU model is more acute and involves local or systemic administration of lipopolysaccharide at sublethal doses. Endpoints for both the EIU and EAU models may include fundoscopic exam, histopathology amongst others. These models are reviewed by Smith et al (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G: In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

Example H: 100A9 Transgenic Mouse Model

It was previously shown that S100A9 transgenic mice display bone marrow accumulation of MDSC accompanied by development of progressive multilineage cytopenias and cytological dysplasia similar to MDS. Further, early forced maturation of MDSC by either all-trans-retinoic acid treatment or active immunoreceptor tyrosine-based activation motif-bearing (ITAM-bearing) adapter protein (DAP12) interruption of $CD_{33}$ signaling rescued the hematologic phenotype and mitigated the disease. This system can be useful to test the effects on JAK1 inhibition on MDS-like disease in a preclinical model. *J. Clin. Invest.*, 123(11):4595-4611 (2013), Accordingly, a JAK1 selective inhibitor is dosed by oral gavage. The compound's ability to reduce the cytopenias and cytological dysplasia observed in the S100A9 transgenic mice is monitored.

Various modifications of the invention, in addition to those described herein, will be apparent to those skilled in the art from the foregoing description. Such modifications are also intended to fall within the scope of the appended claims. U.S. Ser. No. 14/068,796, filed Oct. 31, 2013, is incorporated herein by reference in its entirety. Each reference, including all patent, patent applications, and publications, cited in the present application is incorporated herein by reference in its entirety.

What is claimed is:

1. A process of preparing a compound of Formula Ia:

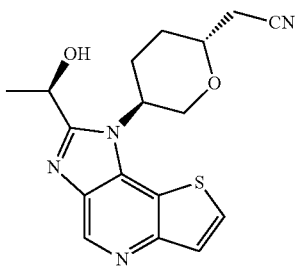

comprising reacting a compound of Formula Ib:

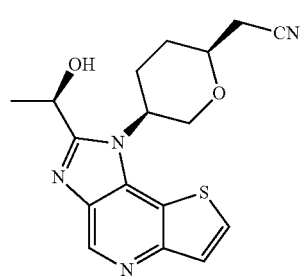

with a strong base in the presence of a solvent component, wherein the compound of Formula Ib is present in a composition comprising the compound of Formula Ib and the compound of Formula Ia prior to said reacting of said compound of Formula Ib with said strong base.

2. The process of claim 1, wherein the strong base is an alkoxide base.

3. The process of claim 1, wherein the strong base is an alkali metal $C_{1-6}$ alkoxide.

4. The process of claim 1, wherein the strong base is potassium tert-butoxide.

5. The process of claim 1, wherein the compound of Formula Ia is prepared as a compound of Formula II:

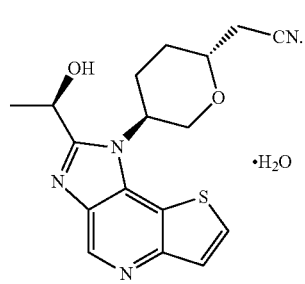

6. The process of claim 1, wherein the solvent component comprises isopropyl alcohol.

7. The process of claim 1, wherein the solvent component comprises isopropyl alcohol and tetrahydrofuran.

8. The process of claim 1, wherein the reacting of the composition with the strong base is conducted at a temperature of about room temperature.

9. The process of claim 1, wherein about 0.05 to about 0.15 equivalents of strong base is used based on 1 equivalent of the compound of Formula Ib.

* * * * *